(12) United States Patent
Sexson et al.

(10) Patent No.: US 10,383,674 B2
(45) Date of Patent: Aug. 20, 2019

(54) TORQUE-LIMITING SCREWDRIVER DEVICES, SYSTEMS, AND METHODS

(71) Applicant: Pro-Dex, Inc., Irvine, CA (US)

(72) Inventors: Benjamin J. Sexson, Laguna Hills, CA (US); Alexander M. Pfotenhauer, Tustin, CA (US)

(73) Assignee: Pro-Dex, Inc., Irvine, CA (US)

( * ) Notice: Subject to any disclaimer, the term of this patent is extended or adjusted under 35 U.S.C. 154(b) by 254 days.

(21) Appl. No.: 15/615,722

(22) Filed: Jun. 6, 2017

(65) Prior Publication Data

US 2017/0348037 A1 Dec. 7, 2017

Related U.S. Application Data

(60) Provisional application No. 62/348,725, filed on Jun. 10, 2016, provisional application No. 62/405,031, (Continued)

(51) Int. Cl.
*A61B 17/88* (2006.01)
*A61B 34/30* (2016.01)
(Continued)

(52) U.S. Cl.
CPC ...... *A61B 17/8875* (2013.01); *A61B 17/1617* (2013.01); *A61B 17/1626* (2013.01);
(Continued)

(58) Field of Classification Search
CPC ............ A61B 17/8875; A61B 2090/03; A61B 2090/031
See application file for complete search history.

(56) References Cited

U.S. PATENT DOCUMENTS 2,414,882 A 1/1947 Longfellow
2,979,089 A 4/1961 Piesker
(Continued)

FOREIGN PATENT DOCUMENTS

DE 19620782 A1 12/1996
JP H06-210575 A 8/1994
(Continued)

OTHER PUBLICATIONS

International Search Report and Written Opinion from corresponding International Application No. PCT/US2017/036216, dated Oct. 10, 2017, 12 pages.
(Continued)

*Primary Examiner* — Christian A Sevilla
(74) *Attorney, Agent, or Firm* — Knobbe, Martens, Olson & Bear, LLP

(57) ABSTRACT

Various torque-limiting screwdriver devices, systems, and methods are disclosed. The screwdriver can include a body, a motor that is configured to rotate a screw engaged with the screwdriver, and a processor configured to control operation of the screwdriver. The screwdriver can have torque-limiting functionality, such as by monitoring the amount of torque applied to the screw and reducing or stopping rotation of the screw when certain torque-limiting criteria are met. In some embodiments, the screwdriver can be switched between manual operation by a user, and automated operation by a motor within the screwdriver. In some embodiments, the screwdriver can be attached to a robotic arm.

15 Claims, 61 Drawing Sheets

Related U.S. Application Data filed on Oct. 6, 2016, provisional application No. 62/346,984, filed on Jun. 7, 2016, provisional application No. 62/405,004, filed on Oct. 6, 2016, provisional application No. 62/467,461, filed on Mar. 6, 2017, provisional application No. 62/480,179, filed on Mar. 31, 2017.

(51) Int. Cl.
*A61B 17/16* (2006.01)
*A61B 90/00* (2016.01)
*A61B 17/00* (2006.01)
*G06F 19/00* (2018.01)
*A61B 17/80* (2006.01)
*A61B 17/86* (2006.01)

(52) U.S. Cl.
CPC .............. *A61B 34/30* (2016.02); *A61B 90/03* (2016.02); *A61B 17/8057* (2013.01); *A61B 17/863* (2013.01); *A61B 2017/00017* (2013.01); *A61B 2017/00398* (2013.01); *A61B 2017/00734* (2013.01); *A61B 2090/031* (2016.02); *A61B 2090/062* (2016.02); *A61B 2090/066* (2016.02); *G06F 19/3481* (2013.01)

(56) References Cited

U.S. PATENT DOCUMENTS

| | | |
|---|---|---|
| 3,120,845 A | 2/1964 | Horner |
| 3,578,872 A | 5/1971 | McBurnie |
| 3,926,264 A | 12/1975 | Bardwell et al. |
| 3,962,910 A | 6/1976 | Spyridakis et al. |
| 3,973,434 A | 8/1976 | Smith |
| 3,974,685 A | 8/1976 | Walker |
| 3,974,883 A | 8/1976 | Sigmund |
| 3,982,419 A | 9/1976 | Boys |
| 4,008,772 A | 2/1977 | Boys |
| 4,008,773 A | 2/1977 | Wallace et al. |
| 4,023,406 A | 5/1977 | Benz, Jr. |
| 4,078,589 A | 3/1978 | Miller |
| 4,081,037 A | 3/1978 | Jonsson |
| 4,095,325 A | 6/1978 | Hashimoto et al. |
| 4,102,182 A | 7/1978 | Brown et al. |
| 4,104,778 A | 8/1978 | Vliet |
| 4,104,780 A | 8/1978 | Sigmund |
| 4,106,176 A | 8/1978 | Rice et al. |
| 4,110,829 A | 8/1978 | Boys |
| 4,163,310 A | 8/1979 | Sigmund |
| 4,179,786 A | 12/1979 | Eshghy |
| 4,233,721 A | 11/1980 | Eshghy |
| 4,244,213 A | 1/1981 | Marcinkiewicz |
| 4,249,117 A | 2/1981 | Leukhardt et al. |
| 4,267,914 A | 5/1981 | Saar |
| 4,273,198 A | 6/1981 | Doniwa |
| 4,292,571 A | 9/1981 | Cuneo |
| 4,344,216 A | 8/1982 | Finkelston |
| 4,359,906 A | 11/1982 | Cordey |
| 4,361,945 A | 12/1982 | Eshghy |
| 4,375,120 A | 3/1983 | Sigmund |
| 4,375,121 A | 3/1983 | Sigmund |
| 4,375,122 A | 3/1983 | Sigmund |
| 4,375,123 A | 3/1983 | Ney |
| 4,426,588 A | 1/1984 | Weilenmann |
| RE31,569 E | 5/1984 | Eshghy |
| 4,450,727 A | 5/1984 | Reinholm et al. |
| 4,562,389 A | 12/1985 | Jundt et al. |
| 4,684,922 A | 8/1987 | Minogue |
| 4,705,038 A | 11/1987 | Sjostrom et al. |
| 4,721,169 A | 1/1988 | Nagasawa et al. |
| 4,830,549 A | 5/1989 | Neumaier et al. |
| 4,894,767 A | 1/1990 | Doniwa |
| 4,908,926 A | 3/1990 | Takeshima et al. |
| 4,995,877 A | 2/1991 | Ams et al. |
| 5,014,793 A | 5/1991 | Germanton |
| 5,038,084 A | 8/1991 | Wing |
| 5,061,885 A | 10/1991 | Fukuhara |
| 5,131,130 A | 7/1992 | Eshghy |
| 5,152,046 A | 10/1992 | Abe |
| 5,154,242 A | 10/1992 | Soshin et al. |
| 5,155,421 A | 10/1992 | Hansson |
| 5,160,978 A | 11/1992 | Faville |
| 5,207,697 A | 5/1993 | Carusillo et al. |
| 5,284,217 A | 2/1994 | Eshghy |
| RE34,556 E | 3/1994 | Sjostrom et al. |
| 5,315,501 A | 5/1994 | Whitehouse |
| 5,337,638 A | 8/1994 | Coss |
| 5,382,251 A | 1/1995 | Hood et al. |
| 5,404,643 A | 4/1995 | Rice |
| 5,410,229 A | 4/1995 | Sebastian et al. |
| 5,440,215 A | 8/1995 | Gilmore |
| 5,496,330 A | 3/1996 | Bates et al. |
| 5,538,423 A | 7/1996 | Coss et al. |
| 5,543,695 A | 8/1996 | Culp et al. |
| 5,563,482 A | 10/1996 | Shaw et al. |
| 5,584,619 A | 10/1996 | Guzzella |
| 5,591,919 A | 1/1997 | Hathaway et al. |
| 5,626,474 A | 1/1997 | Kukla et al. |
| 5,632,759 A | 5/1997 | Rexroth |
| 5,637,968 A | 6/1997 | Kainec et al. |
| 5,689,159 A | 11/1997 | Culp et al. |
| 5,725,533 A | 3/1998 | Carlsson |
| 5,731,673 A | 3/1998 | Gilmore |
| 5,754,019 A | 5/1998 | Walz |
| 5,810,821 A | 9/1998 | Vandewalle |
| 5,868,746 A | 2/1999 | Sarver et al. |
| 5,890,405 A | 4/1999 | Becker |
| 5,898,112 A | 4/1999 | Dawood |
| 5,904,689 A | 5/1999 | Jonjic |
| 5,927,976 A | 7/1999 | Wu |
| 5,980,248 A | 11/1999 | Kusakabe et al. |
| 5,993,454 A | 11/1999 | Longo |
| 6,022,352 A | 2/2000 | Vandewalle |
| 6,110,174 A | 8/2000 | Nichter |
| 6,132,435 A | 10/2000 | Young |
| 6,162,053 A | 12/2000 | Hollander |
| 6,171,312 B1 | 1/2001 | Beaty |
| 6,179,841 B1 | 1/2001 | Jackson |
| 6,197,065 B1 | 3/2001 | Martin et al. |
| 6,211,636 B1 | 4/2001 | Matsubara et al. |
| 6,257,351 B1 | 7/2001 | Ark et al. |
| 6,280,476 B1 | 8/2001 | Metzger et al. |
| RE37,358 E | 9/2001 | Del Rio et al. |
| 6,329,778 B1 | 12/2001 | Culp et al. |
| 6,378,623 B2 | 4/2002 | Kawarai |
| 6,402,757 B1 | 6/2002 | Moore, III et al. |
| 6,471,707 B1 | 10/2002 | Miller et al. |
| 6,479,958 B1 | 11/2002 | Thompson et al. |
| 6,500,208 B1 | 12/2002 | Metzger et al. |
| 6,508,841 B2 | 1/2003 | Martin et al. |
| 6,516,896 B1 | 2/2003 | Bookshar et al. |
| 6,537,274 B1 | 3/2003 | Katz |
| 6,547,565 B1 | 4/2003 | Dawood et al. |
| 6,569,186 B1 | 5/2003 | Winters et al. |
| 6,607,385 B1 | 8/2003 | Sevcik et al. |
| 6,616,446 B1 | 9/2003 | Schmid |
| 6,629,778 B1 | 10/2003 | Enderle et al. |
| 6,656,184 B1 | 12/2003 | White et al. |
| 6,676,665 B2 | 1/2004 | Foley et al. |
| 6,680,595 B2 | 1/2004 | Ito |
| 6,700,341 B2 | 3/2004 | Schaer et al. |
| 6,712,855 B2 | 3/2004 | Martin et al. |
| 6,723,099 B1 | 4/2004 | Goshert |
| 6,780,175 B1 | 8/2004 | Sachdeva et al. |
| 6,916,340 B2 | 7/2005 | Metzger et al. |
| 6,923,813 B2 | 8/2005 | Phillips et al. |
| 6,954,682 B2 | 10/2005 | Makimae et al. |
| 6,981,976 B1 | 1/2006 | Schoenefeld |
| 7,062,979 B2 | 6/2006 | Day et al. |
| 7,091,683 B1 | 8/2006 | Smith et al. |
| 7,141,073 B2 | 11/2006 | May et al. |
| 7,234,536 B2 | 6/2007 | Scholl et al. |
| 7,235,940 B2 | 6/2007 | Bosch et al. |

(56) References Cited

U.S. PATENT DOCUMENTS

| | | |
|---|---|---|
| 7,250,055 B1 | 7/2007 | Vanderwalle |
| 7,255,703 B2 | 8/2007 | Mujwid et al. |
| 7,306,607 B2 | 12/2007 | Metzger |
| 7,331,406 B2 | 2/2008 | Wottreng, Jr. et al. |
| 7,335,207 B1 | 2/2008 | Smith |
| 7,338,286 B2 | 3/2008 | Porter et al. |
| 7,344,376 B2 | 3/2008 | Beaty et al. |
| 7,398,700 B2 | 7/2008 | Makimae et al. |
| 7,400,106 B2 | 7/2008 | DeCicco et al. |
| 7,431,682 B2 | 10/2008 | Zeiler et al. |
| 7,435,085 B2 | 10/2008 | Gugel et al. |
| 7,481,832 B1 | 1/2009 | Meridew et al. |
| 7,484,959 B2 | 2/2009 | Porter et al. |
| 7,488,323 B2 | 2/2009 | Bacastow et al. |
| 7,507,231 B2 | 3/2009 | Schmieding et al. |
| 7,604,636 B1 | 10/2009 | Walters et al. |
| 7,713,285 B2 | 5/2010 | Stone et al. |
| 7,722,678 B2 | 5/2010 | Brown et al. |
| 7,727,282 B2 | 6/2010 | Slone et al. |
| 7,740,425 B2 | 6/2010 | Zeiler et al. |
| 7,770,658 B2 | 8/2010 | Ito et al. |
| 7,823,465 B2 | 11/2010 | Makimae et al. |
| 7,839,112 B2 | 11/2010 | Wei |
| 7,849,766 B2 | 12/2010 | Sharifi-Mehr et al. |
| 7,850,452 B2 | 12/2010 | Suttin et al. |
| 7,881,806 B2 | 2/2011 | Horrigan et al. |
| 7,887,559 B2 | 2/2011 | Deng et al. |
| 7,896,923 B2 | 3/2011 | Blackwell et al. |
| 7,936,140 B2 | 5/2011 | Wei |
| 7,955,334 B2 | 6/2011 | Steiner et al. |
| 8,012,215 B2 | 9/2011 | Metzger et al. |
| 8,025,106 B2 | 9/2011 | Schmidt |
| 8,028,608 B2 | 10/2011 | Sixto, Jr. et al. |
| 8,035,487 B2 | 10/2011 | Malackowski |
| 8,038,702 B2 | 10/2011 | Yuan et al. |
| 8,048,115 B2 | 11/2011 | Winslow et al. |
| 8,057,538 B2 | 11/2011 | Bergin et al. |
| 8,074,334 B2 | 12/2011 | Tharp et al. |
| 8,083,596 B1 | 12/2011 | Silver et al. |
| 8,087,935 B2 | 1/2012 | Beaty et al. |
| 8,103,358 B2 | 1/2012 | Sommer et al. |
| 8,136,431 B2 | 3/2012 | Wengreen |
| 8,147,498 B2 | 4/2012 | Schlueter et al. |
| 8,161,613 B2 | 4/2012 | Schuele et al. |
| 8,172,004 B2 | 5/2012 | Ho |
| 8,182,539 B2 | 5/2012 | Tyber et al. |
| 8,276,487 B2 | 10/2012 | Wengreen et al. |
| 8,286,723 B2 | 10/2012 | Puzio et al. |
| 8,322,456 B2 | 12/2012 | Pozgay et al. |
| 8,347,768 B2 | 1/2013 | Witte |
| 8,372,085 B2 | 2/2013 | Prager et al. |
| 8,425,521 B2 | 4/2013 | Cremer et al. |
| 8,463,421 B2 | 6/2013 | Brett et al. |
| 8,485,075 B1 | 7/2013 | Gauthier et al. |
| 8,523,845 B2 | 9/2013 | Ippisch |
| 8,529,567 B2 | 9/2013 | Garcia et al. |
| 9,265,551 B2 | 2/2016 | Kust et al. |
| 9,585,677 B2 | 3/2017 | Garcia et al. |
| 10,206,731 B2 | 2/2019 | Kust et al. |
| 2002/0146663 A1 | 10/2002 | Nakanishi et al. |
| 2003/0093103 A1 | 5/2003 | Malackowski et al. |
| 2003/0121685 A1 | 7/2003 | Yamamoto |
| 2003/0173096 A1 | 9/2003 | Setton et al. |
| 2005/0096684 A1 | 5/2005 | Farrow et al. |
| 2005/0131415 A1* | 6/2005 | Hearn .............. A61B 17/1626 606/80 |
| 2005/0205274 A1 | 9/2005 | Bogue |
| 2005/0268750 A1 | 12/2005 | Bruce et al. |
| 2006/0117911 A1 | 6/2006 | Raines, Jr. et al. |
| 2006/0234617 A1 | 10/2006 | Francis et al. |
| 2007/0060933 A1 | 3/2007 | Sankaran et al. |
| 2007/0141110 A1 | 6/2007 | Stone et al. |
| 2007/0179476 A1 | 8/2007 | Shelton et al. |
| 2007/0191915 A1 | 8/2007 | Strother et al. |
| 2008/0004646 A1 | 1/2008 | To et al. |
| 2008/0016990 A1* | 1/2008 | Rinner .............. A61B 17/8875 81/467 |
| 2008/0060487 A1 | 3/2008 | Schell |
| 2008/0133020 A1 | 6/2008 | Blackwell et al. |
| 2008/0153062 A1 | 6/2008 | Beaty et al. |
| 2008/0215060 A1 | 9/2008 | Garcia et al. |
| 2008/0221564 A1 | 9/2008 | Rouiller et al. |
| 2008/0286722 A1 | 11/2008 | Berckmans, III et al. |
| 2009/0014192 A1 | 1/2009 | Ito et al. |
| 2009/0260485 A1 | 10/2009 | Hohmann et al. |
| 2010/0116519 A1 | 5/2010 | Gareis |
| 2010/0204685 A1 | 8/2010 | Ippisch |
| 2010/0222812 A1 | 9/2010 | Stone et al. |
| 2010/0318093 A1 | 12/2010 | Ippisch |
| 2011/0000688 A1 | 1/2011 | Iwata |
| 2011/0190907 A1 | 8/2011 | Porter et al. |
| 2011/0245833 A1 | 10/2011 | Anderson |
| 2011/0288549 A1 | 11/2011 | Steiner et al. |
| 2011/0301611 A1 | 12/2011 | Garcia et al. |
| 2011/0306008 A1 | 12/2011 | Suttin et al. |
| 2011/0306009 A1 | 12/2011 | Suttin et al. |
| 2012/0046665 A1 | 2/2012 | Kim |
| 2012/0067139 A1 | 3/2012 | Pernestal |
| 2012/0116494 A1 | 5/2012 | Leynov et al. |
| 2012/0184958 A1 | 7/2012 | Knuchel et al. |
| 2012/0255756 A1 | 10/2012 | Aoki |
| 2013/0014368 A1 | 1/2013 | Woods et al. |
| 2013/0025892 A1 | 1/2013 | Mashiko et al. |
| 2013/0098646 A1 | 4/2013 | Funabashi et al. |
| 2013/0105189 A1 | 5/2013 | Murthy et al. |
| 2013/0116519 A1 | 5/2013 | Wood |
| 2013/0118323 A1 | 5/2013 | Witte |
| 2013/0165930 A1 | 6/2013 | Lehmann et al. |
| 2013/0193891 A1 | 8/2013 | Wood et al. |
| 2013/0269961 A1 | 10/2013 | Lim et al. |
| 2013/0319190 A1* | 12/2013 | Nino .............. B25B 23/141 81/475 |
| 2013/0327552 A1 | 12/2013 | Lovelass et al. |
| 2013/0331895 A1 | 12/2013 | Garcia et al. |
| 2013/0331994 A1 | 12/2013 | Ng et al. |
| 2013/0341058 A1 | 12/2013 | Roehm |
| 2014/0048298 A1 | 2/2014 | Fuchs |
| 2015/0182285 A1 | 7/2015 | Yen et al. |
| 2015/0201918 A1* | 7/2015 | Kumar .............. A61B 17/1622 606/104 |
| 2016/0256213 A1 | 9/2016 | Kust et al. |

FOREIGN PATENT DOCUMENTS

| | | |
|---|---|---|
| JP | H07-124827 A | 5/1995 |
| JP | 2002-283248 | 10/2002 |
| JP | 2005-523174 A | 8/2005 |
| JP | 2012-200807 A | 10/2012 |
| WO | WO 03/090974 A1 | 11/2003 |
| WO | WO 2004/110293 A1 | 12/2004 |
| WO | WO 2008/105057 A1 | 9/2008 |
| WO | WO 2008/128523 A2 | 10/2008 |
| WO | WO 2011/133160 A1 | 10/2011 |
| WO | WO 2015/009850 A1 | 1/2015 |
| WO | WO 2017/214194 A1 | 12/2017 |

OTHER PUBLICATIONS

Brockwell, P., Excerpt from Introduction to Time Series and Forecasting, 2d Ed., 2002.

Brown, R.G., Excerpt from Smoothing, Forecasting and Prediction of Discrete Time Series, 1963.

Gill, P.J., The Yielding of Fastenings During Tightening, The Japan Research Institute, vol. 7, No. 12., 1976.

Hatcher, "Evaluation of the iQTM Intelligent System for Rapid Screw Insertion," undated but believed to be publicly available at least as early as Dec. 2012 (e.g., via http://pharma-gate.net/wpcontent/uploads/ 2012/12/1.pdf).

Hsu, et al., A Modular Mechatronic System for Automatic Bone Drilling, Biomedical Engineering Applications, Basis, & Communications, vol. 13, No. 4, Aug. 2001.

(56) References Cited

OTHER PUBLICATIONS

Sears/Zemansky/Young, Excerpt from "University Physics," 1986.
Smith, S., Excerpt from "The Scientist and Engineer's Guide to Digital Signal Processing," 2d Ed. 1999.
Wadsworth, H., Excerpt from Handbook of Statistical Methods for Engineers and Scientists, 2d Ed., 1990.

* cited by examiner

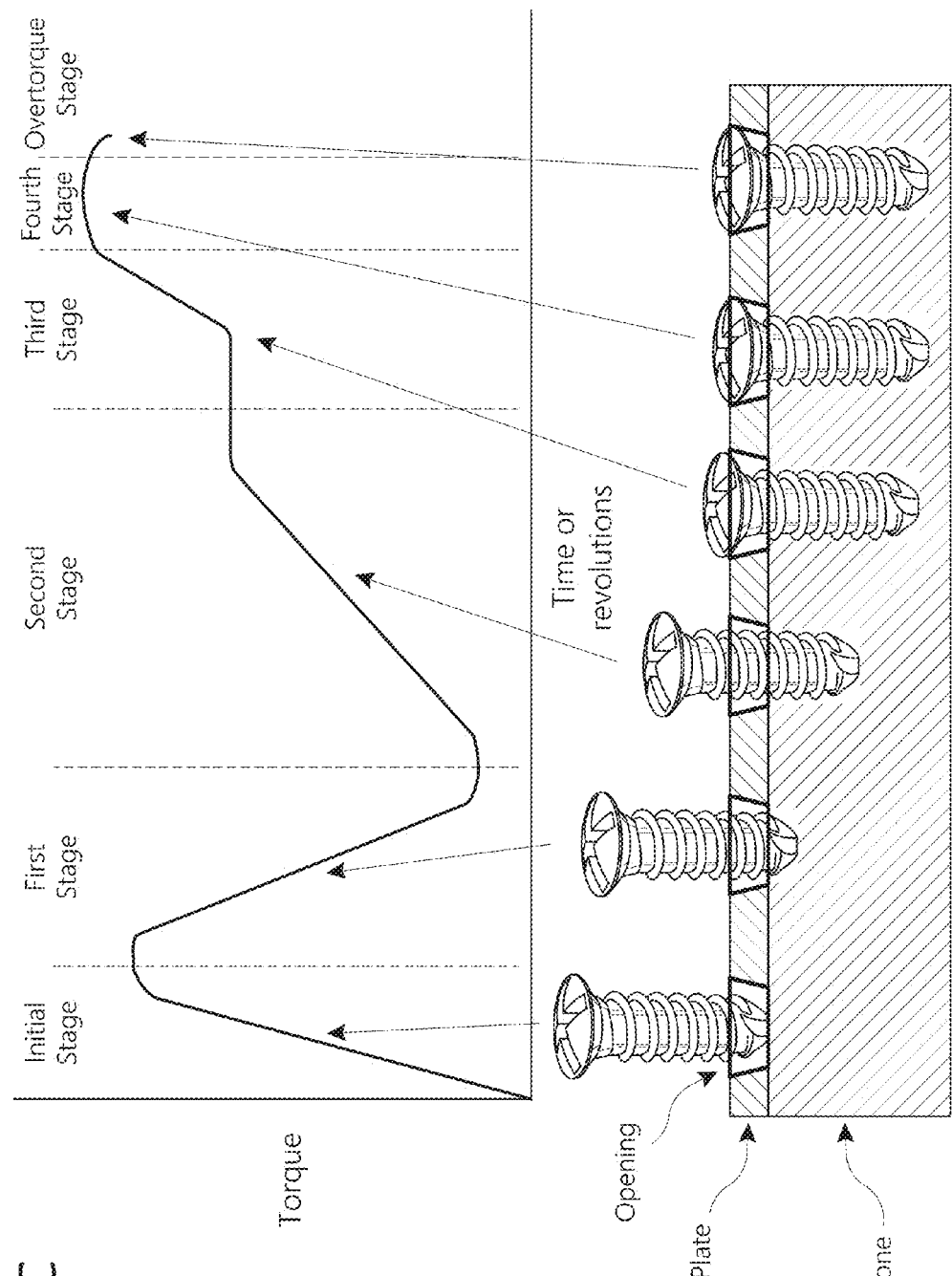

Misplaced Screw Causing Nerve Root Injury

Correctly Placed Lumbar Pedicle Screw

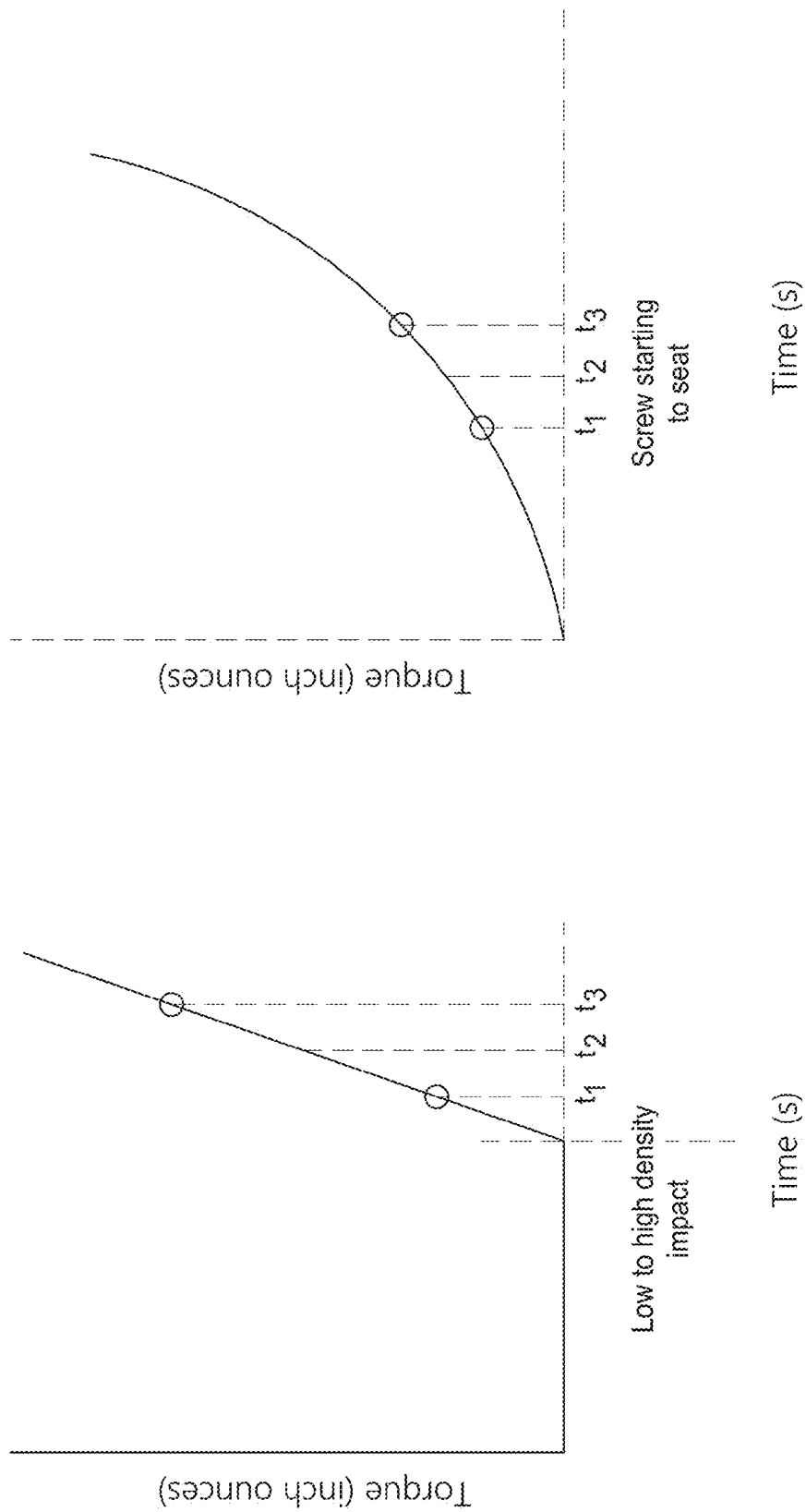

TORQUE-LIMITING SCREWDRIVER DEVICES, SYSTEMS, AND METHODS

CROSS REFERENCE

This application claims from the benefit of U.S. Application No. 62/348,725, filed Jun. 10, 2016, U.S. Application No. 62/405,031, filed Oct. 6, 2016, U.S. Application No. 62/346,984, filed Jun. 7, 2016, U.S. Application No. 62/405,004, filed Oct. 6, 2016, U.S. Application No. 62/467,461, filed Mar. 6, 2017, and U.S. Application No. 62/480,179, filed Mar. 31, 2017. The entirety of each of the aforementioned applications is incorporated by reference herein.

BACKGROUND

Field

This disclosure generally relates to torque-limiting screwdriver devices, systems, and methods, such to torque-limiting screwdrivers for use in orthopedic surgeries.

Certain Related Art

Certain surgical procedures include inserting one or more screws into a bone to retain a structure, such as a plate. During insertion, the screw is threaded into a bone and penetrates into the bone. With continued rotation, the screw seats on the plate, such as by a head of the screw contacting the plate. Still further rotation of the screw secures the screw against the plate and/or further into the bone. Too much rotation of the screw may cause the screw to strip in the bone, thereby reducing the securement of the screw and the plate.

SUMMARY OF CERTAIN FEATURES

It can be beneficial to avoid, or at least inhibit, stripping of the surgical screw in the bone. This can be accomplished with a screwdriver that monitors the torque applied to the screw and stops or reduces the rotation of the screw when certain torque criteria are satisfied. For example, the criteria can include the amount of torque being applied, how the torque is changing over time (e.g., whether the torque is consistently or inconsistently increasing or decreasing), and whether a threshold has been met. The threshold can aid in determining whether the torque being sensed is indicative of the screw being secured against the plate or something else, such as a transitory spike in the torque caused by a localized region of harder bone or otherwise.

Moreover, it can be beneficial to reduce the rotating speed of the screw after certain conditions are satisfied. This can reduce the angular momentum of the screw and/or components of the screwdriver, and thus can reduce the likelihood of unintentional rotation caused by such momentum, even after active driving of the screw has ceased, which can increase the chance of the screw stripping in the bone. Furthermore, reducing the rotational speed of the screw can increase the amount of time available for sensing operations to occur per rotation of the screw. This can facilitate more precise and accurate monitoring of the rotational position of the screw and/or the torque being applied to the screw.

Furthermore, it can be beneficial to provide a screw driving tool with a reduced weight and/or with an improved "feel" for the user. Inserting a screw into a bone can require significant torque. Because of such torque requirements, certain conventional power-operated screw driving tools are generally quite heavy (often greater than 3.5 lbs) and/or may lack sufficient "feel" for a user (e.g., a surgeon) to be comfortable using them to insert screws in certain procedures, such as during certain spinal procedures. Some indications are that the average rate of misplaced spinal pedicle screws is around 20% when using conventional techniques. Some indications are that up to 25% of patients have "at-risk" screws (screws that are adjacent to blood vessels, pleura, esophagus, diaphragm, trachea, etc.).

Various screwdrivers and associated systems and methods are disclosed that address one or more of the concerns discussed above, or other concerns. The screwdriver can include a body and a motor. The motor can be operably connected to a drive head at a distal end of the screwdriver such that the motor can turn the drive head. The drive head can receive a bit (e.g., a crosshead bit, flathead bit, star bit (e.g., Torx), socket bit, or otherwise) that can be interfaced with a screw having a head with a corresponding shape. In some embodiments, the bit comprises a drill bit. The screw and/or drill bit can be positioned at a desired insertion location on a substrate (e.g., a bone) and the motor can be operated to drive the screw and/or drill the drill bit into the substrate. Various embodiments of the screwdriver can limit and/or control torque applied to the screw and/or bit. Certain embodiments reduce the speed of the screw and/or bit during the insertion process. Various embodiments provide one or more of the advantages described above, or none of them.

Embodiments of the screwdrivers, systems, and methods can be used for many different procedures, such as reconstructive, craniomaxillofacial, thoracic, spinal, fracture repair, and extremity surgical approaches, and can incorporate different screws, such as spinal fixation set screws, spinal pedicle screws, extremities fixation screws, and craniofacial modular fixation (CMF) screws. Embodiments can be used to create rigid screw plate constructs and mitigate the risk of screw back out. This can be advantageous for use with CMF plates. Further, in the reconstructive process, embodiments can be used for joint replacements (such as for patients suffering from arthritis), reconstructive orthopedics can restore the function of joints by replacing them. This can include knee, hip, and shoulder surgeries, though other surgeries can be used as well. Fracture repair can be used with respect to bones experiencing trauma, such as large bones like the femur. Further, extremities can be reconstructive, which can include joints such as ankles, writs, hands, fingers, feet, and toes. Each of the determined torque values can vary depending on the particular application, such as those discussed above. Embodiments can be used in the orthopedic realm and outside the orthopedic realm.

Some embodiments are configured to identify differentiations in torque characteristics. For example, the screwdriver can be used to differentiate between passing through skin, the vasculature (e.g., fluid), and into an organ. In some embodiments, the screwdriver can differentiate different bodily tissue so that the user will know where they are operating. In certain embodiments, the screwdriver is configured to reduce or avoid breaching of the spinal column, such as by a drill bit and/or a screw.

In some embodiments, a powered device (such as a screwdriver) can be capable of reading current and voltage and a controller (either inside the device or outside the device) can be configured to implement torque-limiting functionality. In some embodiments, the device can be programmed to use current, voltage and/or torque values to identify the substrate of the screw tip and manage drive velocity accordingly. In some embodiments, the device can be programmed to use current, voltage and/or torque values to identify changes in screw path such as more or less dense materials. In some embodiments, the device can be programmed to use current, voltage and/or torque values to measure screw penetration depth. In some embodiments, the device can identify cortical and cancellous bone using discrete current, voltage and/or torque values and can use the values to interpret the current substrate of the screw tip and control the powered device accordingly (for example, stop it if a higher density tissue type is detected).

Disclosed herein are embodiments of a method for controlling a surgical torque-limiting screwdriver comprising rotating a screw with the surgical torque-limiting screwdriver, thereby driving the screw into bone, measuring a plurality of torque values during said rotating, determining, based at least partly on said measuring, when an inflection point in a torque curve representative of said rotating has been reached or exceeded, and in response to determining that said inflection point has been reached or exceeded, activating a torque-limiting function.

In some embodiments, said determining comprises determining when one of the plurality of torque values is greater than or equal to a threshold value. In some embodiments, said activating comprises activating the torque-limiting function after a time interval elapses from the time that the one of the plurality of torque values is measured.

In some embodiments, the method can further comprise determining a first average from the plurality of torque values, determining a second average from the plurality of torque values, and comparing the first average to the second average, wherein determining when an inflection point in a torque curve representative of said rotating has been reached or exceeded comprises determining when the first average is greater than the second average.

In some embodiments, said determining comprises determining when a torque value from the plurality is less than an earlier torque value in the plurality. In some embodiments, said determining comprises determining when a first torque value from the plurality is greater than N subsequent torque values from the plurality. In some embodiments, N is in the range of 2 to 10 values.

In some embodiments, the method can further comprise measuring a decrease in torque, and computing a percentage decrease from said decrease in torque when said decrease in torque is greater than or equal to a threshold decrease, wherein determining when an inflection point in a torque curve representative of said rotating has been reached or exceeded comprises determining when said percentage decrease is less than or equal to a percentage threshold. In some embodiments, the percentage threshold is in the range of about 5% to about 15%.

In some embodiments, the method can further comprise previously mapping said screw to determine one or more insertion measurements, and comparing one or more said determined values in claims 1 to 9 to one or more of said insertion measurements.

Disclosed herein are embodiments of a torque limiting screwdriver comprising a body comprising a handle, a motor positioned in the body, a drive head positioned at a distal end of the screwdriver, the drive head configured to receive a bit that engages a screw and to be rotated by the motor so as to enable the screwdriver to drive the screw into a bone, a battery positioned in the handle, an electronic circuit board positioned in the handle, wherein the screwdriver is configured to monitor the current draw of the motor to detect the torque applied to the screw and, and limit the amount of torque applied to the screw in response to a torque limiting condition being satisfied.

Disclosed herein are embodiments of a hybrid orthopedic screwdriver, the screwdriver comprising a handle configured to be held by a user, a motor located at least partially within the handle, a drive head located on a distal end of the screwdriver and in communication with the motor, the drive head configured to rotate, and an actuator configured to switch the screwdriver from a manual mode to a powered mode, wherein, in the manual mode, only a user's manual rotational motion of the handle is used to rotate the drive head, and wherein, in the powered mode, the motor is used to rotate the drive head, wherein a default mode for the hybrid orthopedic screwdriver is the manual mode.

In some embodiments, the screwdriver only maintains powered mode while the actuator is actuated. In some embodiments, the actuator is a button or a switch.

In some embodiments, the hybrid orthopedic screwdriver can further comprise a mode actuator configured to switch the screwdriver from a drill mode to a screw mode, wherein the motor operates at a different rate between the drill mode and the screw mode. In some embodiments, when in drill mode the default mode is the powered mode.

In some embodiments, the hybrid orthopedic screwdriver can further comprise a plurality of buttons configured to turn the screwdriver on and off, to provide a rotational direction to the screwdriver when in powered mode, and to provide a rotational speed to the drive head when in powered mode. In some embodiments, the hybrid orthopedic screwdriver can further comprise a torque limiter configured to stop the motor when a specific torque is achieved in the powered mode. In some embodiments, the drive head is configured to determine the type of screw in contact with the drive head. In some embodiments, the hybrid orthopedic screwdriver can further comprise an integrated battery pack.

The handle can have various forms. For example, in some embodiments, the handle comprises a pistol grip, J-hook grip, closed ring grip, ball handle grip, t-handle grip, or otherwise. In some embodiments, the actuator actuates a ratchet mechanism for changing between the manual mode and the powered mode. In some embodiments, when the screwdriver is driving a screw, the screwdriver is configured to identify a change in the type of tissue that the screw is being driven into. In some embodiments, the screwdriver is configured to identify the change in the type of tissue based on a measured torque value, a voltage value, or a current value. In some embodiments, the drive head is configured to automatically turn off upon a sudden increase or decrease in torque.

Also disclosed herein are embodiments of a system for inserting a screw into a patient's bone, the system comprising a hybrid orthopedic screwdriver, the screwdriver comprising a handle configured to be held by a user, a motor located at least partially within the handle, a drive head located on a distal end of the screwdriver and in communication with the motor, the drive head configured to rotate, and an actuator configured to switch the screwdriver from a manual mode where only a user's manual rotational motion of the handle is used to rotate the drive head to a powered mode where the motor is used to rotate the drive head, wherein a default mode for the hybrid orthopedic screwdriver is the manual mode, and a screw having distal markings near a distal tip of the screw to indicate when the manual mode is to be used and proximal markings proximal to the distal markings to indicate when the powered mode is to be used.

In some embodiments, the drive head is configured to read the screw type when the screw is inserted into the drive head.

In some embodiments, the distal markings and proximal markings are different colors.

Disclosed herein are embodiments of a hybrid screwdriver, the hybrid screwdriver comprising a handle configured to be held by a user, a motor located at least partially within the handle, and a drive head located on a distal end of the screwdriver and in communication with the motor, the drive head configured to rotate, wherein the drive head is configured to operate in manual operation or powered operation, and wherein the hybrid screwdriver is configured to analyze torque of the drive head to provide feedback to the user.

In some embodiments, the feedback is turning off the motor. In some embodiments, the feedback is a visual or auditory cue for the user. In some embodiments, the torque is a first derivative or a second derivative of a torque profile. In some embodiments, the hybrid screwdriver is configured to provide information on tissue that the drive head is operating into to the user. In some embodiments, the information is a type of tissue.

Disclosed herein are embodiments of a powered device comprising a handle configured to be held by a user, a motor, and a drive head located on a distal end of the screwdriver and in communication with the motor, the drive head configured to rotate, wherein the powered device is configured to measure current and/or voltage used in operation of the drive head, and wherein the powered device is configured to differentiate between a first tissue type and a second tissue type, and implement torque-limiting functionality.

Disclosed herein are embodiments of a powered device comprising a handle, a motor, and a controller configured to receive inputs indicative of torque, voltage, and/or current measurements operating the motor, wherein the controller uses the measurements to adjust operating speeds and/or functionalities of the motor. In some embodiments, the measurements include changes in torque, voltage, and/or current.

Also disclosed herein are embodiments of a powered device comprising a sensor capable of reading current and voltage, and a controller configured to implement torque-limiting functionality. In some embodiments, the device is configured to use current, voltage and torque values to identify the substrate of the screw tip and manage drive velocity accordingly. In some embodiments, the device is configured to use current, voltage and torque values to identify changes in screw path such as more or less dense materials. In some embodiments, the device is configured to use current, voltage and torque values to measure screw penetration depth. In some embodiments, the device is configured to identify cortical and cancellous bone using discrete current, voltage, or torque values, use the values to identify the type of substrate that the screw tip is being driven into, and take action in response to a change in the type of substrate. In some embodiments, the device is configured to detect when a screw tip or screw body has impacted cortical bone, and in response, signal the motor to stop driving. In some embodiments, the device is configured to identify transition zones between materials with variable densities using discrete current, voltage, or torque values.

In some embodiments, the device is configured to identify and characterize material types based on expected current, voltage or torque feedback preprogrammed to the controller. In some embodiments, the device is configured to identify when a screw has initially started driving based on current, voltage or torque readings. In some embodiments, the device is configured to identify when a screw is seating based on current, voltage, or torque readings. In some embodiments, the device is configured to distinguish between a screw seating, a screw impacting a substrate of a higher or lower density, or a screw initiating its driving based on programming of the controller. In some embodiments, the device is configured to identify the substrate the screw tip is currently penetrating based on the readings of current and voltage and information programmed into the controller. In some embodiments, the device is configured to compare voltage, current or torque readings while the screw is driving with preprogrammed expected values to identify the type of material the screw is currently in.

Disclosed herein are embodiments of an electric screwdriver comprising a drive head configured to drive a screw, and a motor configured to drive the drive head, a controller configured to control operation of the motor, the controller being configured to determine, based on torque measurements taken at a plurality of different times, whether the screw is being seated in cancellous bone or is impacting cortical bone, wherein, in response to determining that screw is impacting cortical bone, the controller stops the motor's driving of the drive head, and wherein, in response to determining that screw is being seated in cancellous bone, the screwdriver continues driving the screw until a torque-limiting criteria has been achieved.

In some embodiments, the torque measurements for the screw being seated in cancellous bone are generally non-linear. In some embodiments, the torque measurements for the screw impacting cortical bone are generally linear. In some embodiments, determining whether the screw is being seated in cancellous bone or is impacting cortical bone is determined with the equation $(t_2-t_1)/t_1>Y$, where X comprises consecutive increasing torque values, Y is a percentage value, and $t_1$ and $t_2$ comprise torque values at two different times. In some embodiments, the electric screwdriver can further comprise a depth gauge.

Disclosed herein are embodiments of a hybrid screwdriver system, the hybrid screwdriver system comprising a handle configured to be attached to a robotic arm, a motor located at least partially within the handle, and a drive head located on a distal end of the screwdriver and in communication with the motor, the drive head configured to rotate, wherein the drive head is configured to operate in manual operation or powered operation, and wherein the hybrid screwdriver is configured to analyze torque of the drive head to provide feedback to the robotic arm.

In some embodiments, the handle is removably attached to the robotic arm. In some embodiments, the robotic arm is configured to move the hybrid screwdriver without user input. In some embodiments, the robotic arm is configured to stop motion after the hybrid screwdriver reaches a specified torque threshold.

Disclosed herein are embodiments of a hybrid screwdriver system, the hybrid screwdriver system comprising a robotic arm, a motor, and a drive head connected to the robotic arm and in communication with the motor, the drive head configured to rotate, wherein the drive head is configured to operate in manual operation or powered operation, and wherein the robotic arm is configured to analyze torque of the drive head.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

The preceding summary is meant to be a high-level summary of certain features within the scope of this disclosure. The summary, the following detailed description, and the associated drawings do not limit or define the scope of protection. The scope of protection is defined by the claims. No feature is critical or indispensable.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

FIG. 8C illustrates the relationship of the stages of FIG. 8A to the plot of FIG. 8B.

FIGS. 54A-B illustrate beginning portions of example torque curves of a screw encountering hard bone (54A) and of a screw seating in softer bone (54B), with the Y-axis (torque) not shown.

DETAILED DESCRIPTION OF CERTAIN EMBODIMENTS

Various features and advantages of the disclosed technology will become more fully apparent from the following description of the several specific embodiments illustrated in the figures. These embodiments are intended to illustrate the principles of this disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein.

Overview of the Screwdriver

Various embodiments of torque-limiting devices (e.g., screwdrivers), systems, and methods are disclosed. For purposes of presentation, the devices are called "screwdrivers," however various embodiments are configured for use with items other than screws. For example, several embodiments are configured to drive drill bits, such as to drill the drill bit into a bone. As more fully described below, the devices, systems, and methods can determine when to stop a screw being driven into various types of bone so as to avoid stripping the screw in the bone or inserting into the incorrect location. Some embodiments can provide certain benefits of powered surgical screwdrivers, as well as certain benefits of manual screwdrivers. By having the manual setting, the screwdrivers disclosed herein can provide an enhanced feel for surgeons so that they feel comfortable and in control of the operation. In some embodiments, the manual mode can aid a surgeon in placing (e.g., starting) a screw, thus reducing misplacement of screws, improving patient health, and minimizing risk. By having the powered mode for further insertion of the screws, overall surgery times can be reduced, along with surgeon arm fatigue as there would be a reduction of physical labor.

In some embodiments, the torque-limiting screwdrivers can be configured for use in a plurality of settings, such as a powered setting and a manual setting, and thus can be considered "hybrid" screwdrivers. The screwdrivers can be configured to enable a user to easily and conveniently switch between the settings. Certain embodiments can be particularly useful in orthopedic surgery procedures, such as in the insertion of screws into spinal bones. The screwdrivers can be used for other surgical purposes as well, and the particular purpose does not limit the disclosure.

Certain embodiments of the disclosed screwdrivers can be used, for example, as a powered surgical device in an on-plane form factor, a powered surgical device in an on-plane form factor for spinal applications, a powered surgical device in an on-plane form factor for extremities, and/or a powered surgical device in an on-plane form factor for large bone. The screwdrivers can be used for other procedures as well, and the particular procedure is not limiting. In some embodiments, the screwdriver can be operated remotely, for example, through the use of robotics.

Figure 1:
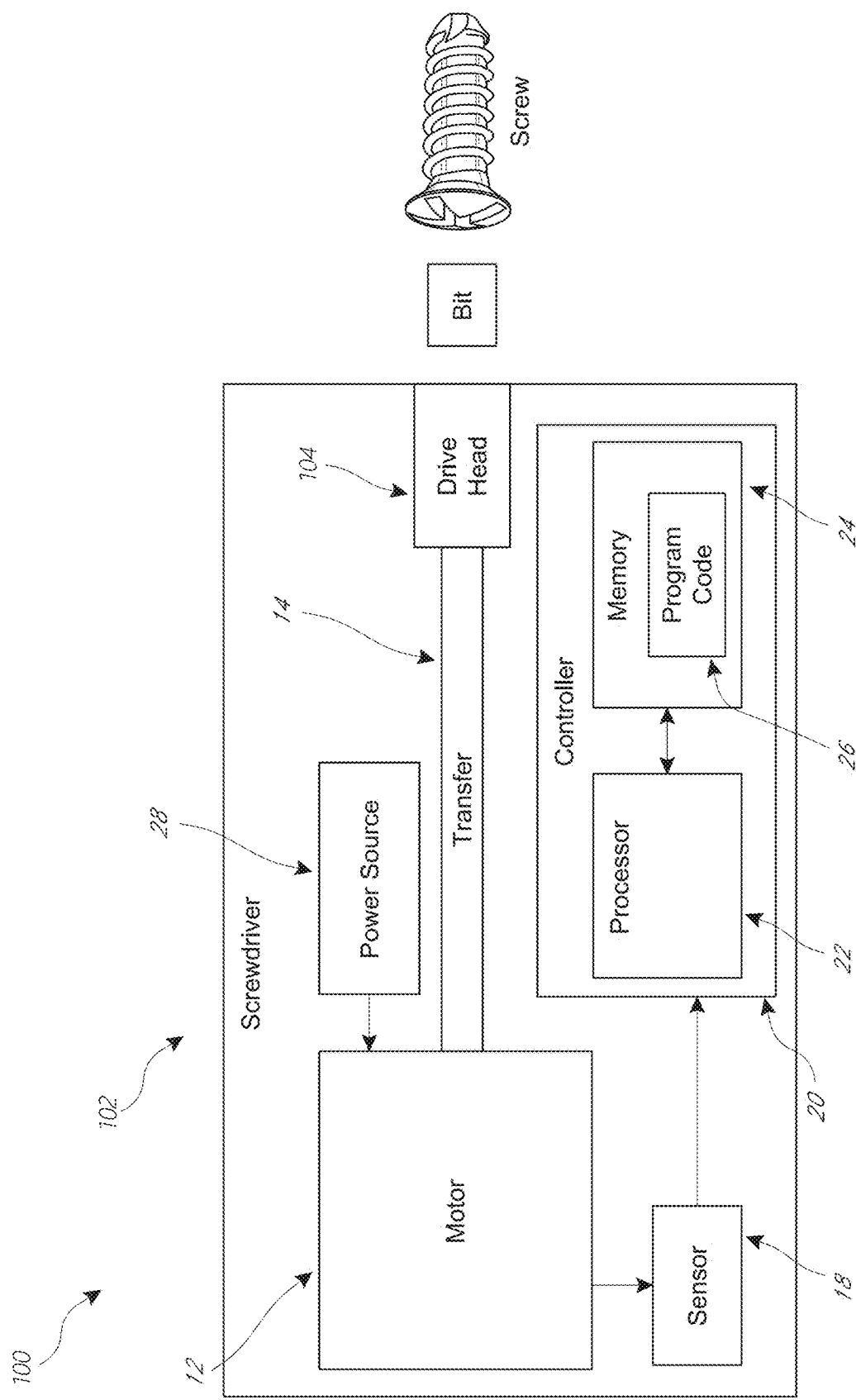
FIG. 1 schematically illustrates an example embodiment of a screwdriver.

As shown in FIG. 1, a torque-limiting screwdriver 100 includes a body 102 (also called a housing, handle, or casing) that supports a motor 12. A transfer assembly 14 (e.g., one or more shafts, gears, etc.) operably connects the motor 12 to a drive head 104 at a distal end of the screwdriver 100 such that the motor 12 can turn the drive head 104. The drive head 104 can receive a bit, such as a crosshead bit, flathead bit, star bit (e.g., Torx), socket bit (e.g., hex), or otherwise. The bit in turn can be interfaced with a screw, such as an orthopedic screw, having a head with a corresponding shape. Thus, the screw can be positioned at a desired insertion location on a substrate (e.g., a bone) and the motor 12 can be operated to drive the screw into the substrate.

In some variants, the motor 12 is powered by a power source, such as a source of AC or DC electrical power. In some embodiments, the motor 12 is powered by an on-board power source, such as a battery, capacitor, or otherwise. In some embodiments, the motor 12 is configured to receive power from an external source, such as from a console, wall socket, or other external power source. In some embodiments, the motor 12 is a brushless DC motor. In some embodiments, the motor 12 is a three-phase electric motor. The motor 12 can include one or more hall sensors, which can send signals to the controller 20 to enable the controller 20 to determine the number of revolutions of the motor 12. In certain variants, the controller 20 determines the number of revolutions of the screw from the number of revolutions of the motor 12.

The screwdriver 100 can monitor and/or limit the torque that the screwdriver 100 is applying to the screw during the insertion process. For example, as described in more detail below, the screwdriver 100 can include a sensor 18 that senses the current supplied to the motor 12. The sensor 18 can send such data to a controller 20, which can include a processor 22 coupled with a memory 24, along with other electronic components. Because, in some implementations, the current supplied to the motor 12 can be proportional to the torque applied to the screw, the controller 20 can dynamically determine the amount of torque being applied to the screw. In certain variants, the controller 20 is configured to determine or receive data signals indicative of one or more of the following data features: current supplied to the motor 12, number of revolutions of the screw and/or motor, distance traveled by the screw (e.g., into the bone), speed of the motor 12, or otherwise.

As described in more detail below, various embodiments of the screwdriver 100 can include an algorithm adapted to limit and/or control the torque applied to the screw. This can enable the screwdriver 100 to be used with different screw sizes and different bone densities. The algorithm can be included in the memory 24 as program code 26 to be implemented on a computer-readable non-transitory medium. The processor 22 can execute the program code 26 to perform various operations, such as determining a torque limit, instructing the motor to cease operation, instructing a power source 28 to reduce and/or stop providing power to the motor 12, or other operations. The processor 22 and/or program code 26 can control and/or implement any of the features described in this disclosure, such as any of the torque-limiting features. Some implementations are configured to stop the rotation of the screw by shutting-off (e.g., substantially or totally) the power to the motor 12. Certain implementations include a brake to actively decelerate the motor or components. For example, some implementations include a friction or electromagnetic brake.

In various embodiments, the screwdriver 100 can include one or more computers or computing devices that implement the various functions described herein under the control of program modules stored on one or more non-transitory computer storage devices (e.g., hard disk drives, solid state memory devices, etc.). Each such computer or computing device typically includes a hardware processor and a memory. Where the screwdriver 100 includes multiple computing devices, these devices may, but need not, be co-located. In some cases the screwdriver 100 may be controlled by cloud-based or shared computing resources, which can be allocated dynamically. The processes and algorithms described herein may be implemented partially or wholly in application-specific circuitry, such as Application Specific Integrated Circuits and Programmable Gate Array devices. The results of the disclosed processes and process steps may be stored, persistently or otherwise, in any type of non-transitory computer storage such as, e.g., volatile or non-volatile storage.

Figure 2A:
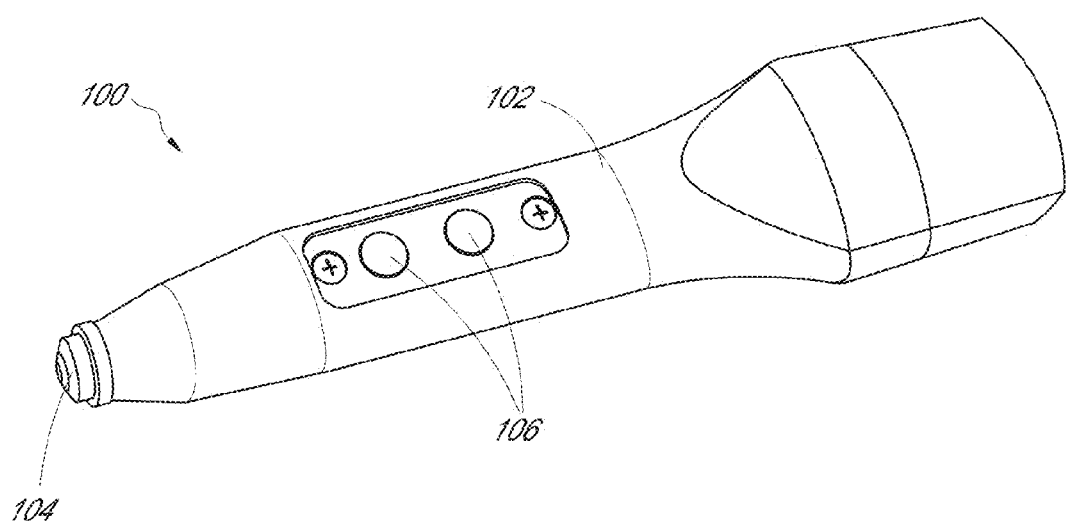
FIG. 2A illustrates a perspective view of the screwdriver of FIG. 1.

FIG. 2A further illustrates the screwdriver 100. As shown, the body 102 of the screwdriver 100 can include an input device 106, such as buttons, switches, or otherwise. Through the input device 106, a user can control aspects of the operation of the screwdriver 100, such as the controller 20. For example, the user can instruct the screwdriver 100 regarding rotational direction (e.g., forward or reverse), speed, and/or otherwise. The input device 106 may power the screwdriver 100 on or off, or maintain the screwdriver 100 in standby mode. In some embodiments, the screwdriver 100 may have variable speed options as well as forward and reverse capabilities.

Figure 2B:
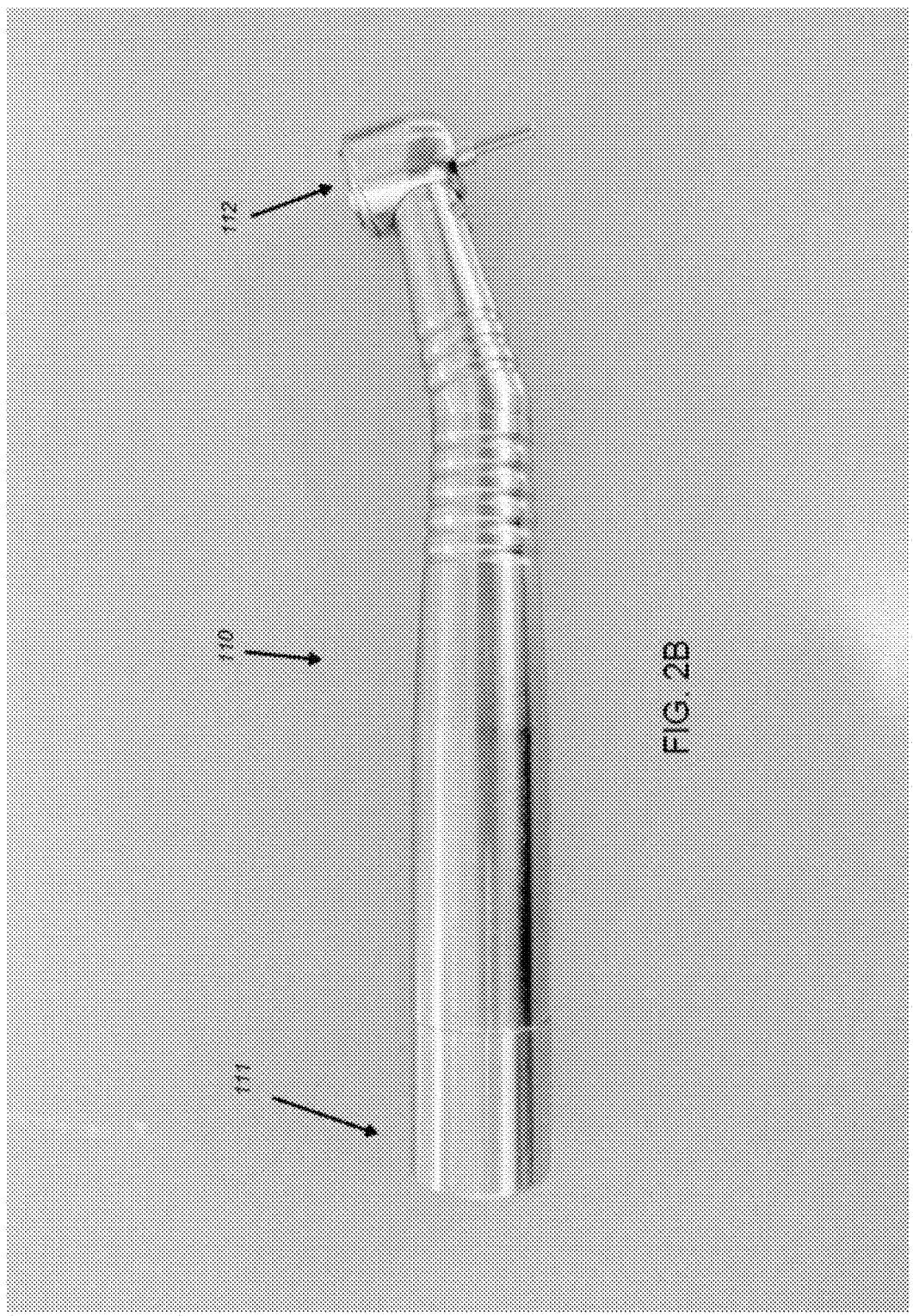
FIG. 2B illustrates an attachment that can be used with the screwdriver of FIG. 1.

In some embodiments, different attachments can be removably attached to the screwdriver 100, such as at a collet of the screwdriver 100. An example of an attachment 110 is shown in FIG. 2B. The attachment 110 can allow a user to access harder to reach areas, e.g., as shown, the attachment can include an offset of about: 40°, 50°, 60°, 70°, 80°, 90°, 100°, 110°, 120°, or other values. The attachment 110 can change the rotational plane of the screwdriver 100. Further, the attachment 110 may be an extension for further reaching positions. The attachment 110 can be selectively connected to and/or removed from the screwdriver 100, such as by connecting or disconnecting from a collet of the screwdriver 100. As illustrated, the attachment 110 can comprise a low-profile and/or elongate configuration and can extend the reach of activity. This can be beneficial in certain types of procedures, such as certain thoracic procedures involving a posterior approach to access anterior ribs. In some embodiments, the attachment 110 comprises an extension adaptor with a first end 111 and a second end 112. The first end 111 can be configured to mate with the drive head 104 of the screwdriver 100. The second end 112 can include a drill bit and/or can be configured to mate with a drill bit and/or can be configured to mate with a screw. The attachment 110 can include a power transmission assembly (e.g. a drive shaft) that operably connects the drive head 104 of the screwdriver 100 to the second end 112 of the attachment 110. For example, the power transmission assembly can convey rotational motion from the drive head 104 to the second end 112 of the attachment 110. In various embodiments, the attachment 110 is configured to enable drilling and/or screw insertion into a target site (e.g., a bone) that is spaced a substantial distance apart from the body 102 of the screwdriver 100 (e.g., at least about: 10 mm, 25 mm, 50 mm, 75 mm, 100 mm, 150 mm, 200 mm, 250 mm, 300 mm, distances between the aforementioned distances, or other distances). In some embodiments, the attachment 110 has a reflective and/or mirror-like surface, which can be added, attached, or integrated into the attachment 110 to enhance visibility of the target site. The attachment 110 can be articulating or fixed with respect to the body 102 of the screwdriver 100. The attachment 110 can be configured for use with the screwdriver 100, which can include torque-limiting functionality. In some embodiments, the attachment 110 is configured for use with a driver device that does not include torque-limiting functionality.

In some embodiments, the screwdriver 100 can include a mode switch (or similar mechanism) that can allow the user to toggle between modes, such as the powered and manual modes discussed below. In some embodiments, the mode switch can change the parameters of the screwdriver 100 based on a specific screw type. In some embodiments, the mode switch can allow the screwdriver 100 to recognize the presence of different adapters or attachments.

In some embodiments, the body 102 may provide a user with visual output on certain parameters of the screwdriver 100, such as, power status, mode, speed, or otherwise. Some embodiments are configured to provide trajectory orientation, such as through the use of MIMS (Medical Information Management System), MEMS (Micro-Electromechanical Systems), gyroscopic, or other technology that can cue a user about the orientation of the screwdriver. In some embodiments, the screwdriver 100 is configured to indicate (e.g., to a user) deviations from a "zeroed" orientation, such as the angular deviation from a horizontal or vertical position. In some embodiments, the body 102 can include an LED or LCD display to provide information, to the user. In some embodiments, the screwdriver 100 can connect to an outside display, such as a monitor, such as through a wireless network, to provide a visual output to the outside display. In some embodiments, haptic cues (e.g., small vibrations) can provide information to the user. In some embodiments, electromagnetic field (EMF) or Hall Effect sensors can be incorporated into embodiments of the screwdriver 100.

Various shapes of the screwdriver 100 are contemplated. For example, some embodiments are on plane, which can enhance feel. In this disclosure, the term "on plane" describes a device with a generally linear arrangement. This is in contrast to "off plane" devices, which generally have an L-shaped arrangement, such as a pistol grip. In some embodiments, the screwdriver 100 has an on plane configuration in which the tip is generally in line with the user's hand, such as the tip and the handle being generally collinear. In some variants, the screwdriver 100 has an off plane configuration, such as having a pistol grip.

An on plane configuration can have a number of advantages. For example, an on plane configuration can allow a user to apply force through the screwdriver to the screw along a linear axis, rather than, for example, through a curve or elbow. In some implementations, an on plane design reduces or eliminates a moment of force that can be associated with certain pistol grip designs, such as due to force being applied to the handle of the pistol grip device and then being transferred through the barrel of the pistol grip device. Reducing or eliminating the moment can increase control of the screw and/or decrease user fatigue (e.g., by reducing exertion needed to counteract the moment). Some embodiments with an on plane configuration can avoid or reduce slippage of the screw relative to the substrate, or at least increase the chance that such slippage will occur generally in a desired direction. For example, the on plane arrangement can locate the fingers closer to the bit than a pistol grip design, which can enable the user to better detect when slippage is occurring, or is about to occur, and to take action in response.

In some embodiments, an on plane configuration allows a user to use larger muscles (e.g., muscles of the upper arm) compared to pistol grip devices (e.g., which may require usage of wrist muscles or other smaller muscles). The engagement of the larger muscles can provide greater strength and/or control. In some embodiments, there may be no cantilever or no pistol grip.

The on plane arrangement can provide an improved weight distribution, such as by removing weight from a cantilever from the handle. In some arrangements, an on plane configuration can enhance the sensitivity with which a user can discern characteristics of the screw and/or the substrate. For example, while large muscles can control the initial driving, the fingers, located closer to the tip than if an off plane arrangement, can be used for final manipulations. Thus, the user can use their fingers for fine-tuning, which can provide more dexterity when handling the screwdriver. Further, the on plane arrangement can dampen vibrations as the screwdriver is being held by the larger arm muscles. Moreover, by stabilizing with the large arm muscles and using the wrists/fingers to manipulate, there can be less migration of the screwdriver, especially caused by unwanted jolts, as compared to an off plane arrangement, which uses a larger moment arm and thus is more susceptible to jerks/movements.

In some embodiments, the sleek form factor of the device can reduce packaging sizes, thus resulting in cost savings. Certain embodiments can ease the transition from manual screwdrivers to powered screwdrivers, can increase visibility of the tip and tissues into which the driving is occurring, and/or can reduce weight of the screwdriver which can mitigate user fatigue.

In some embodiments, the screwdriver 100 can be partially or fully cannulated and/or configured to be cannulated. This can allow the threading of a guidewire and/or k-wire (or other wire, the type of which is not limiting) through the screwdriver 100. Further, the cannulation can allow for suction to be used in conjunction with the screwdriver 100. The cannula can extend through the entirety of the screwdriver 100 (e.g., from back to front), or can include an aperture on a side of the body 102 that can lead to a tip (or near a tip) of the screwdriver 100. The cannula can general extend along (or be parallel with) a longitudinal axis of the screwdriver 100.

Further, in some embodiments, the motor itself within the screwdriver 100 can be cannulated as well. Thus, a cannula can extend through at least a portion of the motor of the screwdriver 100. The motor can be partially or fully cannulated and/or configured to be cannulated. The cannula can extend through the entirety of the motor (e.g., from back to front), or can include an aperture on a side of the body 102 that can lead to a tip (or near a tip) of the screwdriver 100. In some embodiments, the cannula can generally extend along (or be parallel with) a longitudinal axis of the motor in the screwdriver 100. The cannulated motor can be used for a number of different applications including, for example, using a cannulated motor in a powered surgical device, using a cannulated motor in an on-plane powered surgical device, using a cannulated motor in an on-plane powered surgical device for spinal applications, using a cannulated motor in an on-plane powered surgical device for extremities, and/or using a cannulated motor in an on-plane powered surgical device for large bone applications. However, the cannulated motor can be used for other procedures as well, and the particular procedure is not limiting.

In some embodiments, the body 102 can include different shaped handles (or grips). The different handles can be used to replace a portion of the body 102, and thus can be integrally formed with the body 102 in some embodiments. In some embodiments, different handles can be detachable from a proximal end of the body 102, thus allowing a user to choose which particular handle suits the needs of a particular use (e.g., surgery). In some embodiments, the handles can be switched out during surgery by the surgeon. For example, the handles can have an attachment mechanism to the body 102, such as through male/female threading, snaps, fasteners, or other non-limiting removable attachment devices.

Figure 3:
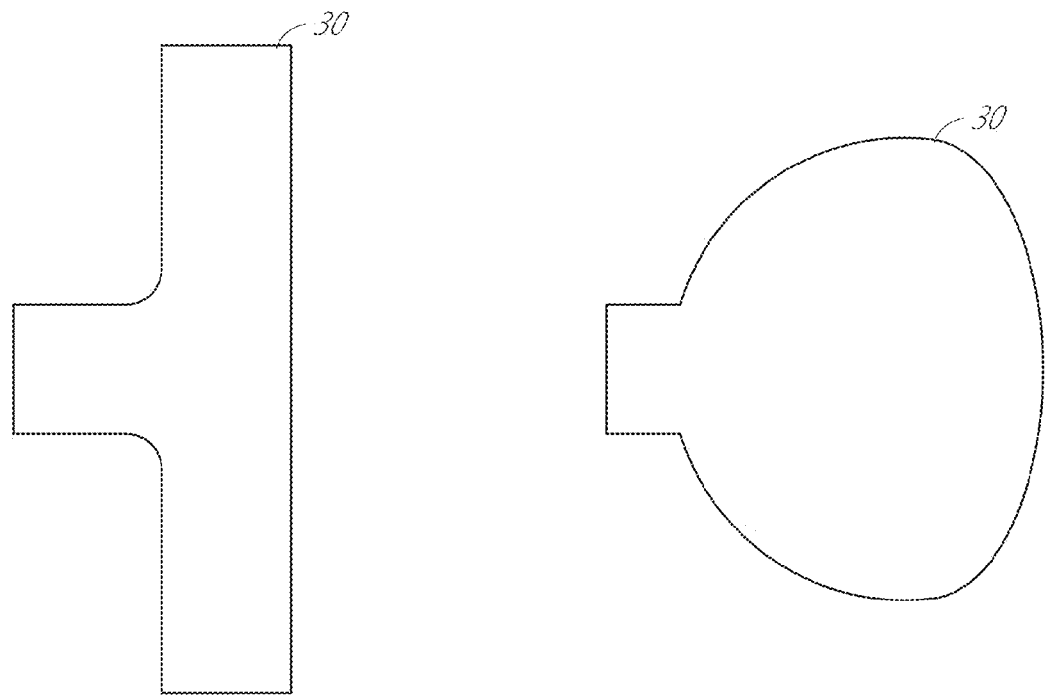
FIG. 3 illustrates example end views of handle shapes for embodiments of a screwdriver.
Figure 4:
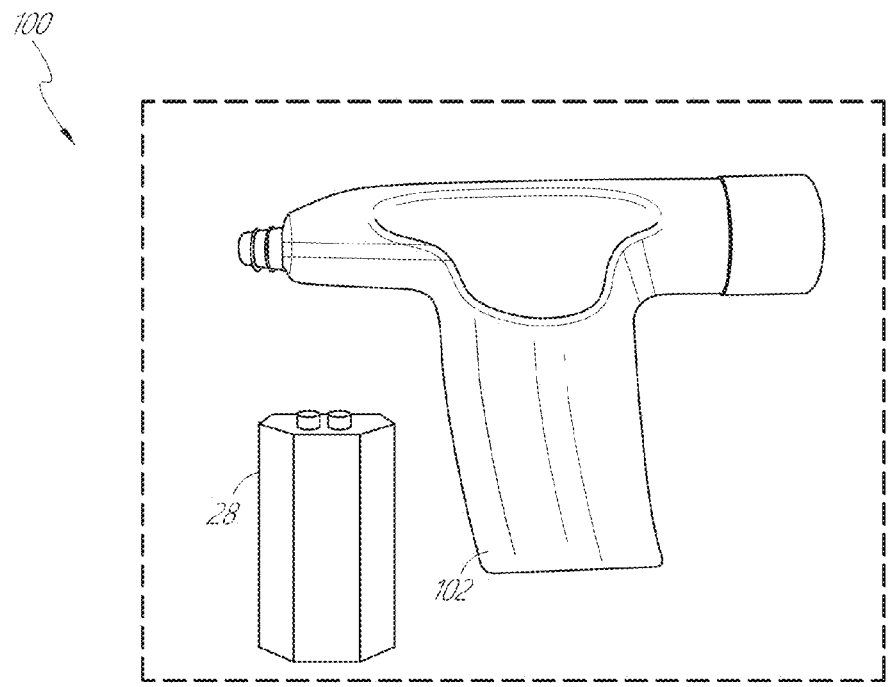
FIGS. 4-7 illustrate examples of a screwdriver comprising a body with a handle that includes a power source, such as a battery.

The handles can be made from a number of different materials, such as metal, plastic, or rubber, and can come in a variety of different shapes. Handles can further include gripping features such as bumps or divots that make it easier for a user to control the handle. FIG. 3 illustrates example cross-sectional shapes of handles 30 that can be used with the screwdriver as disclosed herein. As show, these handles 30 can have a generally "T" shape (FIG. 3 left) or generally circular or ball shape (FIG. 3 right). While these two particular handles 30 are illustrated, other handles can be used as well, such as generally "J" shaped, pistol grip, or closed ring handles, or otherwise. The particular handle shapes and dimensions of FIG. 3 are not limiting.

FIGS. 4-7 illustrate an example of the screwdriver 100. The screwdriver 100 has a body 102 with a handle that can be grasped by a user. In the embodiment illustrated, the handle has a pistol grip configuration. In some implementations, the screwdriver 100 is approximately 7 inches long. The screwdriver 100 can have a power source, such as a battery 28. The power source 28 can fit in the body 102, such as in the handle.

Figure 5:
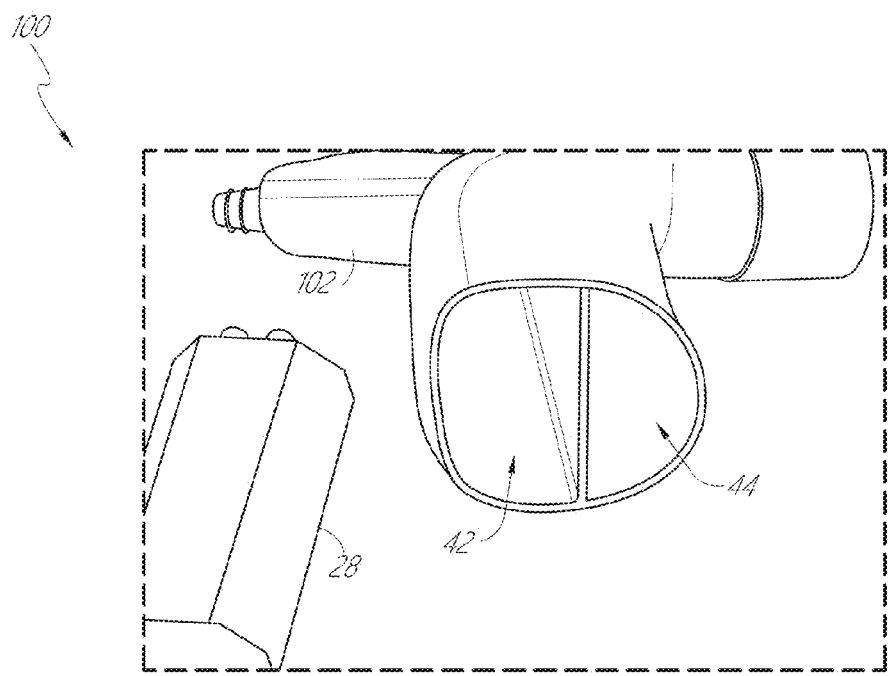

FIG. 5 shows the bottom opening of the body 102. The body 102 can have multiple cavities, such as a first cavity 42 that is designed to hold the battery 28 and a second cavity 44 that is designed to hold electronics, such as circuit boards. After the circuit boards are installed, a cover plate can be affixed to seal the second cavity 44 from moisture intrusion. Having the boards and battery both inserted into the handle allows the length and profile of the screwdriver 100 to be reduced.

Figure 6:
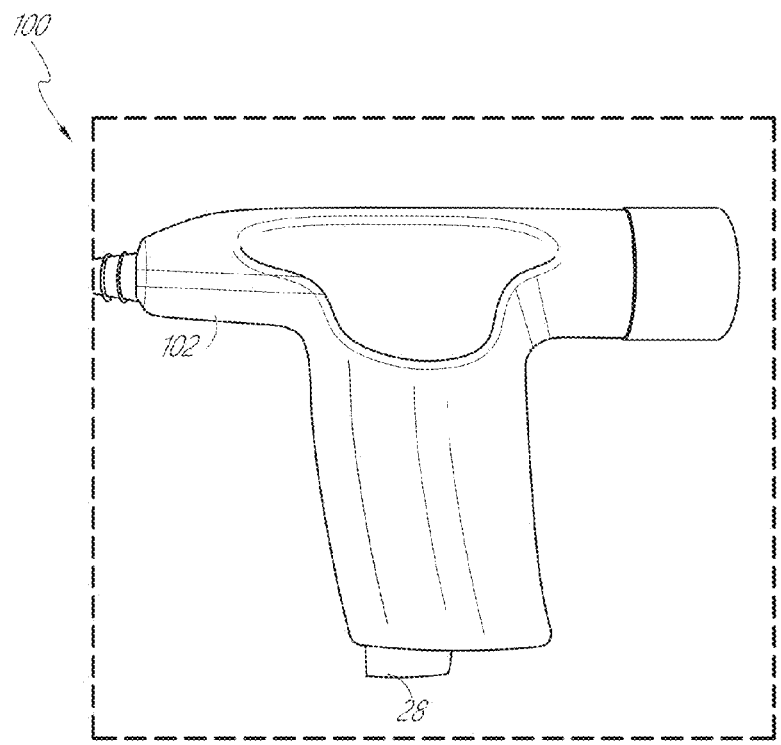
Figure 7:
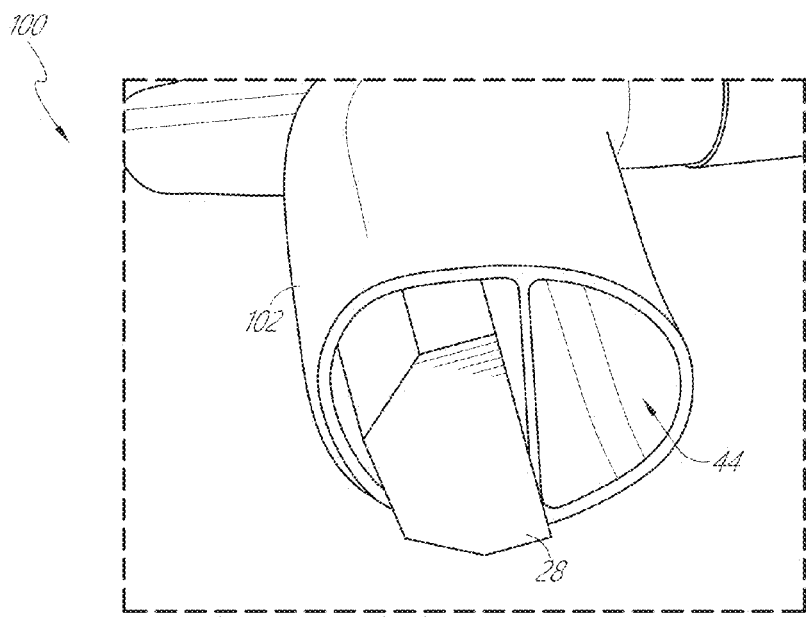

FIG. 6 shows the battery 28 placed in the handle of the body 102 of the screwdriver 100. In some implementations, the battery 28 is fully enclosed in the body 102. A fully enclosed battery 28 can ensure that the battery 28 is not exposed to bio-material during operation. In some embodiments, the battery 28 is contained and/or sealed with a door. FIG. 7 shows the battery 28 inside the handle. The screwdriver design could include a mechanism that covers the battery 28 from the bottom and forces it up into the handle. This feature will ensure that the battery 28 engages the power contacts with the screwdriver 100 during use. In some embodiments, this mechanism may be hinged on one side to function like a trap door. In other embodiments, this mechanism may be pinned at one corner to rotate over or away from the cavity to allow the battery 28 to be inserted.

Various embodiments of the screwdriver 100 have a variety of operational characteristics. For example, some embodiments provide a maximum rotational speed (at no load) of at least about: 3,000 rpm, 4,000 rpm, 5,000 rpm, 6,000 rpm, 10,000 rpm, values between the aforementioned values, or other values. As noted above, some embodiments slow the rotation of the screw after a slowdown point has been reached. Certain such embodiments have a slowed speed (at no load) of less than or equal to about: 500 rpm, 600 rpm, 700 rpm, 800 rpm, 900 rpm, 1,000 rpm, 1,100 rpm, 1,200 rpm, values between the aforementioned values, or other values. Certain implementations of the screwdriver 100 can provide a torque on the screw of at least about: 25 in-ozs, 30 in-ozs, 35 in-ozs, 40 in-ozs, 45 in-ozs, values between the aforementioned values, or other values. Some embodiments of the screwdriver 100 can provide a torque on the screw of at least: 25 N-cm, 30 N-cm, 35 N-cm, 40 N-cm, 45 N-cm, values between the aforementioned values, or other values.

Various embodiments of the screwdriver 100 include a forward input that a user can engage to instruct the screwdriver 100 to turn the screw in a forward direction, such as in the direction to insert the screw into the bone. For example, the forward input can be a switch, button, dial, trigger, slider, touchpad, or the like. Certain embodiments have multiple input members, such as a fast forward switch (e.g., the motor will spin at about 4100 RPM at no-load) and a slow forward switch (e.g., motor will spin at 500 RPM at no-load). Some implementations have a reversing input, which can instruct the screwdriver 10 to turn the screw in a reverse direction, such as in the direction to remove the screw from the bone. The reversing input can be similar to the forward input, such as the options described above. In some embodiments, engaging the reversing input causes the motor to spin at about 500 RPM at no-load. In certain implementations, the final rotational speed of the screw is about 500 RPM. In some embodiments, the forward input and the override input are the same component.

In various embodiments, the screwdriver 100 includes components configured to adjust the torque data, such as by filtering the torque data, decreasing noise in a signal from a sensor 18 (e.g., a motor current sensor), or otherwise. For example, the screwdriver 100 can include one or more low-pass filters. The filters can be implemented in hardware and/or software. For example, in some embodiments, the filters comprise resistance capacitor circuitry. Certain embodiments include a software filter configured to filter out certain frequencies and/or levels of torque data. In various embodiments, the filtering components can facilitate a smoother torque curve. In some variants, the filtering components can reduce errors in the torque-limiting functionality that may otherwise be caused by noise and/or outlier measurements. In some embodiments, conversion of current, voltage, power, etc. to torque values (such as nm, inch ounces, etc.) can be performed with a look up table or a mathematical equation.

In some embodiments, the screwdriver can incorporate additional features that can identify and differentiate the starting torque for an already seated screw from that of a screw that has just started, such as through a higher initial torque value, which can prevent the device from continuing to drive and potentially strip an already seated screw. This can be especially advantageous once a screw is already seated and attempts to further screw after the screwdriver (such as the driver software) has been reset. In some embodiments, a system comprising the torque-limiting screwdrivers discussed herein and an extension adaptor can be configured to removably attach to the screwdriver, the extension adaptor configured to enable insertion of the screw into a bone that is spaced at least 30 mm apart from the body of the screwdriver.

Further disclosure regarding certain features related to torque-limiting screwdrivers can be found in U.S. Pat. No. 9,265,551, filed on Jul. 16, 2014, which is hereby incorporated by reference in its entirety. For example, certain torque-limiting functionality is disclosed in the '551 Patent and can be used in conjunction with the screwdrivers disclosed herein.

Overview of the Screw Insertion Process

Figure 8A:
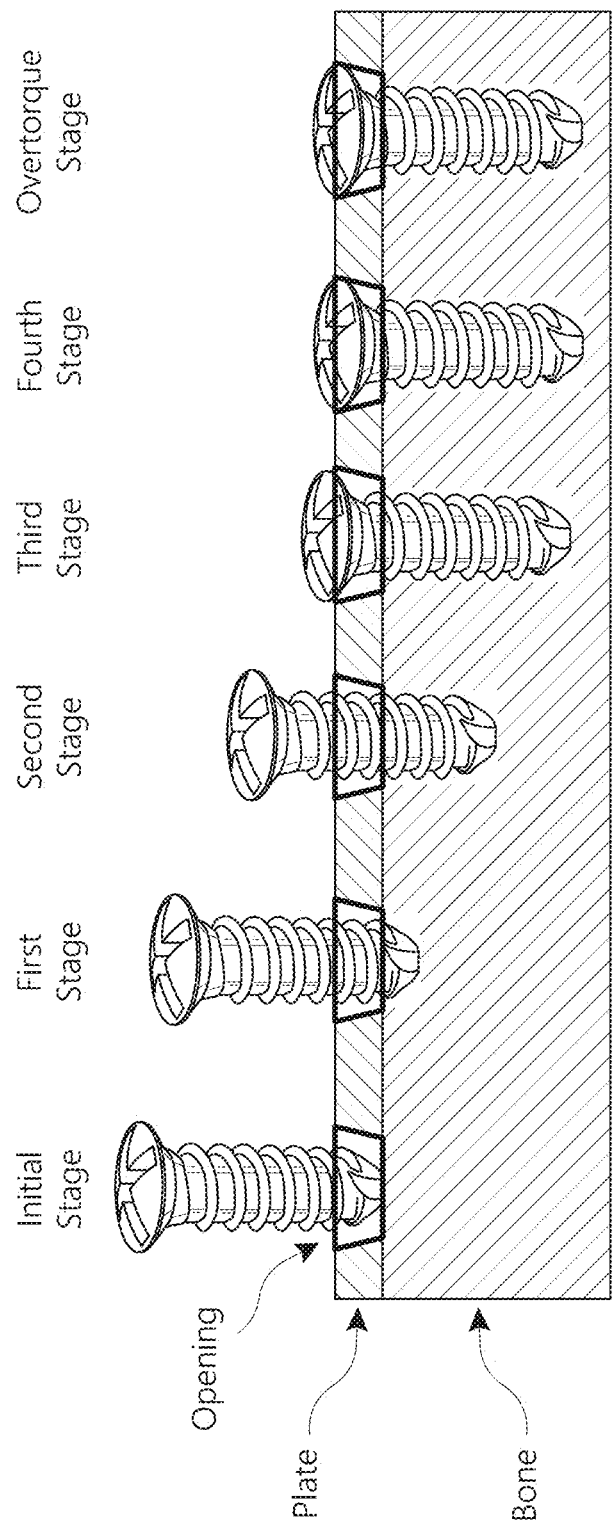
FIG. 8A schematically illustrates various stages in the process of inserting a screw into a bone.
Figure 8B:
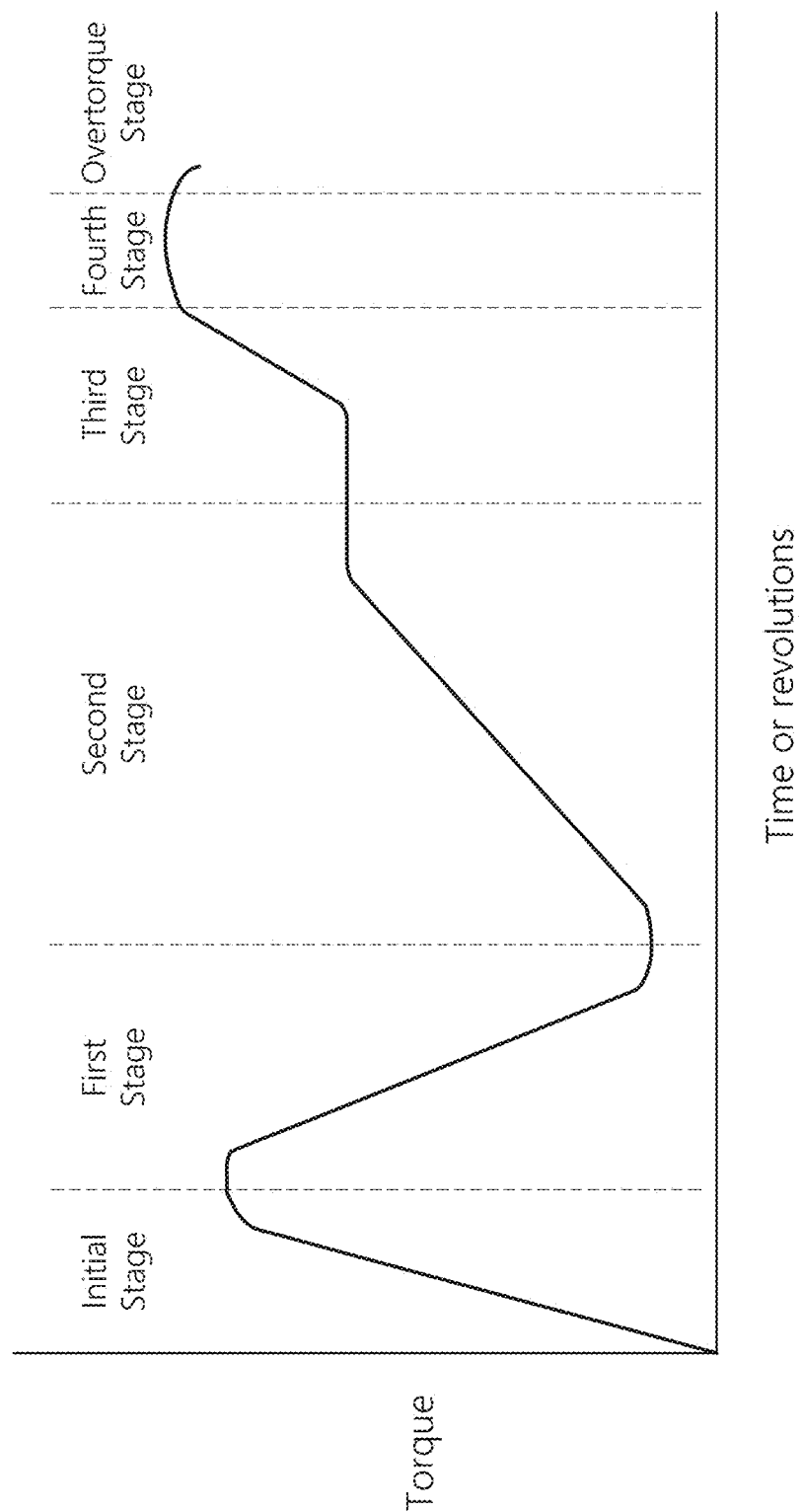
FIG. 8B illustrates an example plot of torque as a function of time or revolutions during insertion of a screw into a bone.

The process of inserting a screw into a bone to secure a plate against the bone includes several steps. As shown in FIG. 8A, in an initial stage, the screw is positioned through an opening in the plate and adjacent to the bone at the desired insertion location. Also, the screw can be coupled with the screwdriver 100 discussed above, which can begin rotating the screw relative to the bone. As the screw rotates, it begins to cut into the bone, which provides space for the screw's body to be inserted. For screws that are self-tapping, the screw can begin to push material outwardly, thereby creating a path into the bone. To facilitate this process, the user can apply some axial force to the screw, such as via the screwdriver 100. As illustrated in FIG. 8B, during the initial stage, the torque gradient can exhibit a steep upward (e.g., positive) slope and the rotational speed of the screw is reduced (e.g., compared to the speed at no load). FIG. 8C illustrates the relationship of FIGS. 8A and 8B.

After the initial stage concludes, a first insertion stage begins. In the first stage, the screw body moves axially into the bone via the path created in the initial stage. As shown in FIG. 8B, during the first stage, the torque gradient can have a downward (e.g., negative) slope and the rotational speed of the screw can increase compared to the later part of the initial stage.

In the second stage, the screw continues advancing into the bone following the path created by the entry threads. Typically, the screw advances substantially the entire or the entire thread length of the body of the screw (less the axial thickness of the plate) into the bone. In some implementations, the torque vs. time (or torque vs. revolutions of the screw) curve will have a positive torque gradient as the screw advances the length of the thread.

The third stage begins when the screw head initially seats against the plate. As illustrated, the screw typically has a head that is larger in diameter than at least a portion of the opening in the plate. Thus, during the third stage, the head can contact the plate and inhibit or prevent the screw from passing further through the plate. This can result in an initial sharp increase of the torque curve. As shown in FIG. 8B, during the third stage, the torque gradient can be upward (e.g., positive). For example, the slope can be less than the slope of the initial stage but greater than the slope of the second stage. In certain implementations, the later part of the third stage, the torque gradient exhibits a flattening (e.g., reaches a plateau) and/or includes a crest, such as a localized maximum torque that is less than the torque at an inflection point during a fourth stage, which is discussed below. In certain variants, the rotational speed of the screw during the third stage is less than the speed during the second stage.

In the fourth stage, the screw is fully seated on the plate, thereby fixedly securing the screw, bone, and plate. This can include the head of the screw being partly or completely received into the opening of the plate and inhibited or prevented from further axial movement into the bone by the plate. As illustrated in FIG. 8B, during the fourth stage, the torque can continue increasing, though at a rate that is less than the rate of the third stage. For example, the slope of the curve in the fourth stage can be less than the slope in the third stage (e.g., at the end of the third stage). The torque can reach a peak during the fourth stage, after which the torque begins decreasing. In some implementations, the rotational speed of the screw in the fourth stage is less than the rotational speed of the screw in the initial, first, second, and third stages.

In an overtorque stage, which can occur after the fourth stage, an additional amount of torque can be applied to the screw to further tighten the screw in the bone. This can slightly overtorque the screw in the bone (e.g., violate a yield strength of the screw and/or the bone). Too much overtorque is undesirable as it can cause the screw to strip. But a relatively small amount can be beneficial, because it can result in slight deformation of the screw and/or the bone, which can aid in maintaining the screw in its position, and thus inhibit or prevent the plate from moving relative to the bone. In various implementations, the overtorqueing is accomplished by rotating the screw a final amount. For example, the screw can be rotated about: one rotation, ½ of a rotation, ¼ of a rotation, ⅛ of a rotation, values in between, or otherwise. In some embodiments, the amount that the screw is overtorqued is at least 1 Newton centimeter (N-cm) and/or less than or equal to about 5 N-cm (or between about 1 N-cm and 5 N-cm).

Certain aspects of the stages of the insertion process are summarized below in Table A:

TABLE A

| Stage | Torque | Torque Gradient | Speed | Observations |
| --- | --- | --- | --- | --- |
| Initial Stage: Screw driving initiation and bone engagement | Initially no load and no torque | Steeply positive | High | Increasing values. Large noise to signal ratio |
| First Stage: Screw advancement starts | Initially high | Negative | High | Decrease or leveling off values |
| Second Stage: Screw inside bone and continue advancing | Initially low | Positive | Reducing | Smooth continuous increasing values |

TABLE A-continued

| Stage | Torque | Torque Gradient | Speed | Observations |
|---|---|---|---|---|
| Third Stage: Screw seated on plate | Middle | Flat to positive | Mid | Small plateau or distinct increase of values |
| Fourth Stage: Screw compressing plate against bone | High | Level and/or negative | Low | Cresting, plateau of values |
| Overtorque Stage: Screw seated on plate and additional torque applied | High to Middle | Negative | Low | Decreasing values |

Typically, to remove the screw from the bone, and to free the plate, the screwdriver 100 can be interfaced with the head of the screw and the rotation of the screw reversed. Because the screw is not cutting into the bone and is not being tightened against the bone or plate, the torque on the screw during a removal operation is normally less than during the insertion process described above.

Torque During the Screw Insertion Process

The torque used to insert the screw in a given bone can vary significantly. One factor that affects the amount of torque required to insert the screw into a bone is the density of the bone, which can change based on age, gender, disease, and other factors. Typically, the denser the bone, the greater the force required to insert the screw. Additionally, the density of the bone can change depending on the location of the screw. Another factor that affects the amount of torque required to insert the screw into a bone is the specifics of the screw, such as the diameter, length, thread type (e.g., shape and/or number of threads per inch), material, coefficient of friction with the bone, and other features. Generally, the longer the screw (e.g., an axial length of at least about: 3 mm, 4 mm, 5 mm, or otherwise), the more torque required to insert the screw to a fully installed position.

Figure 9:
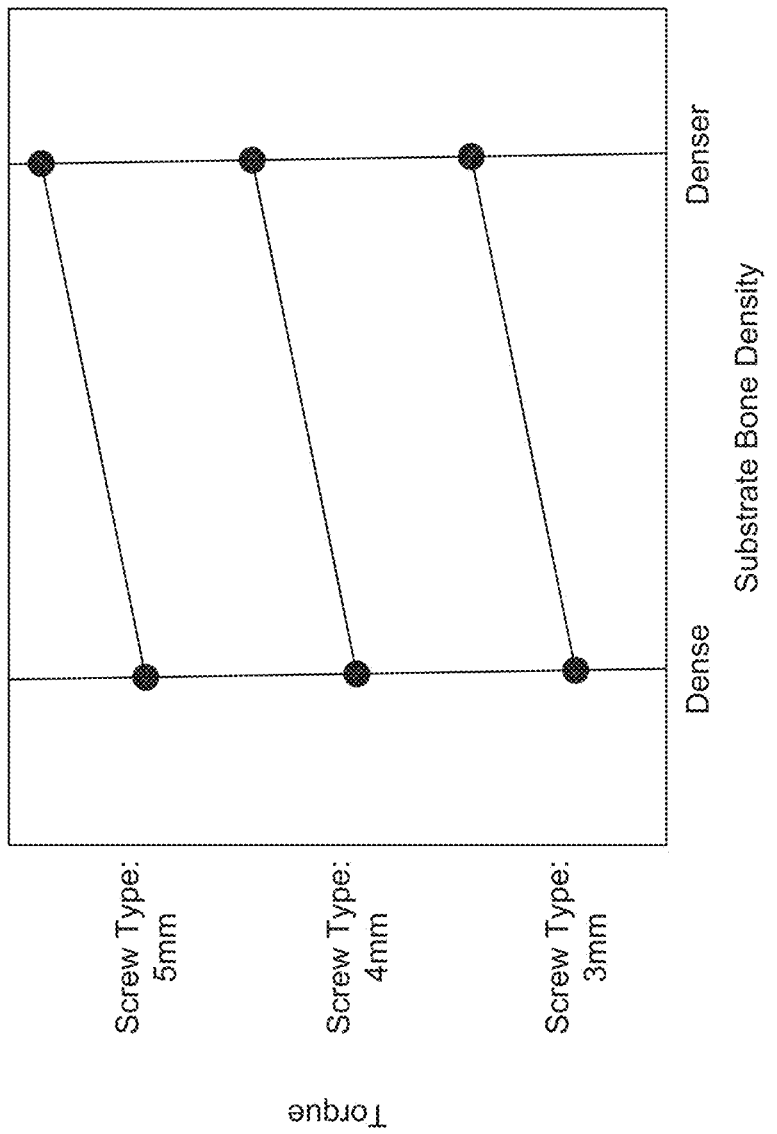
FIG. 9 illustrates a plot of example torques on 3 mm, 4 mm, and 5 mm screw types as a function of bone density.

FIG. 9 shows illustrative example torques on 3 mm, 4 mm, and 5 mm screw types as a function of bone density. As shown, there can be different torque requirements based on the size and type of the screw and the bone density substrate against which the screw is inserted. This can cause issues in using a fixed torque limit. For example, if the torque limit is fixed based on a dense bone substrate and the smaller (e.g., 3 mm) screw, then a larger (e.g., 5 mm) screw inserted on a denser bone substrate may not seat completely. On the other hand, if the torque limit is fixed based on a larger (e.g., 5 mm) screw and denser substrate, the smaller (e.g., 3 mm) screw on a less dense substrate may strip during insertion.

Certain screwdrivers include a fixed torque value for a specific screw type. For example, for a 3 mm screw, the screwdriver 100 can include a torque limit set at a value that is specific to that type of screw and to the particular type of bone the screw is to be inserted into. For a screwdriver 100 configured to receive and drive three types of screws (e.g., 3 mm, 4 mm, and 5 mm), the screwdriver 100 would include three torque limit values. The values can be determined by experimentation for each screw type with each substrate.

Variable Torque-Limiting Embodiments

Various embodiments of the screwdriver 100 use an algorithm to dynamically determine the torque limit and/or when to stop rotation of the screw. This can allow the screwdriver to account for insertion variables (e.g., the density of the bone and the screw specifics) so as to correctly seat the screw, while also inhibiting or preventing the screw from stripping or damaging the bone of the patient. In several embodiments, the insertion variables do not need to be input into the screwdriver. Rather, certain embodiments of the screwdriver 100 can determine when the screw is properly installed and/or can avoid stripping of the screw based on the torque required to turn the screw in relation to other parameters, such as the time that the screwdriver 100 has been rotating the screw and the amount of torque that has already been applied to the screw.

Several torque-limiting methods, algorithms, and components are described below. Any method, algorithm, or component disclosed anywhere in this specification can be used in conjunction with any other method, algorithm, or component disclosed anywhere in this specification, or can be used separately.

Differential Torque Comparisons

Figure 10:
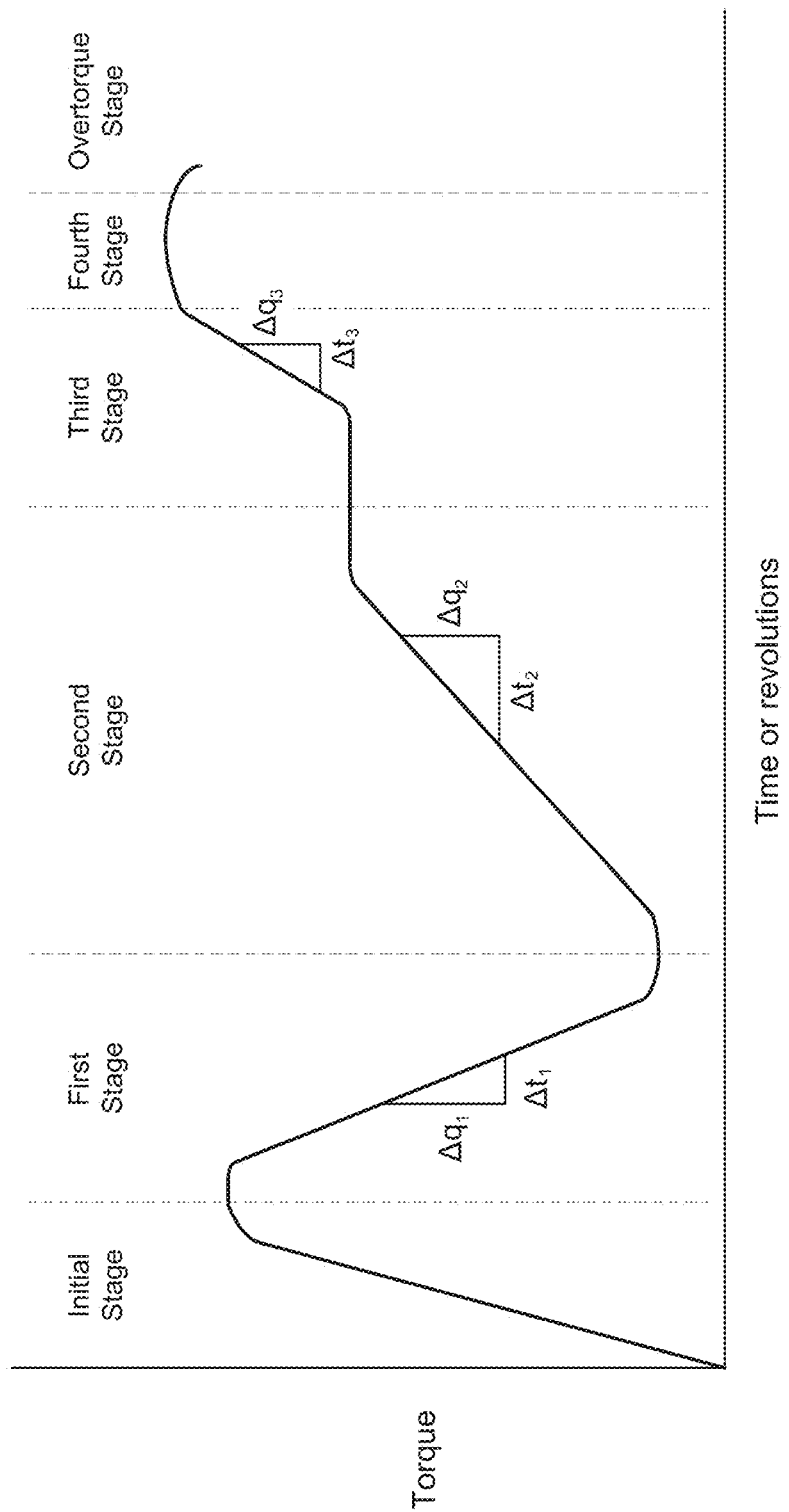
FIG. 10 illustrates a torque plot with comparative torque regions.

In some embodiments, an algorithm can be used that compares how the torque has changed during certain portions of the insertion operation. To facilitate this comparison, the controller 20 can calculate discreet changes in the torque during the course of insertion of the screw (e.g., torque as a function of time). For example, as shown in FIG. 10, the controller 20 can determine Δq values and Δt values throughout some or all of the insertion of the screw, where Δq is the change in torque and Δt is the change in time, depth, or revolution of the screw. Certain embodiments use a relationship of the Δq values and Δt values during the insertion stages of the screw. For example, some implementations engage a torque-limiting feature (e.g., stop the motor) when the following comparison is met:

$$\frac{\Delta q3}{\Delta t3} > \frac{\Delta q2}{\Delta t2} > \frac{\Delta q1}{\Delta t1}$$

Such an algorithm can enable the screwdriver 100 to limit the torque while also accounting for certain aspects of the insertion process. For example, this algorithm can include and/or consider that the torque starts at low level and speed starts at a high level. Certain embodiments of the algorithm include and/or consider that, when the screw is being threaded into the bone, the torque may increase and the reduction in speed may decrease. Some variants of the algorithm include and/or consider that, when the screw seats on the plate, the torque may increase and the speed may decrease. Various embodiments of the algorithm are configured to inhibit or avoid the failure mode of stripping of the screw.

In certain embodiments, a measured amount of torque (or current drawn by the motor, or other methods of determining rotation/torque discussed herein) is sampled, such as about every: 10 milliseconds (ms), 20 ms, or other time values. The torque and time data can be stored in the memory. This can facilitate monitoring the change in the torque relative to time (e.g., a first derivative of the torque). As noted above, the torque can be directly proportional to the motor power required to insert the screw. In several embodiments, the torque at a given time is determined by the controller 20, which receives a signal from the sensor 18 indicative of the current drawn by the motor 12.

Consecutive Torque Values, Thresholds, and Slowdowns

In some embodiments, the methods and algorithms activate (e.g., engage) torque-limiting functionality when a number of values meet a condition. For example, as discussed in more detail below, the screwdriver 100 can monitor the torque for a number (e.g., two, three, four, five) of consecutive decrementing values and can reduce and/or stop rotation of the screw (e.g., by reducing or stopping power to the motor 12) in response to such a condition being met.

Figure 11:
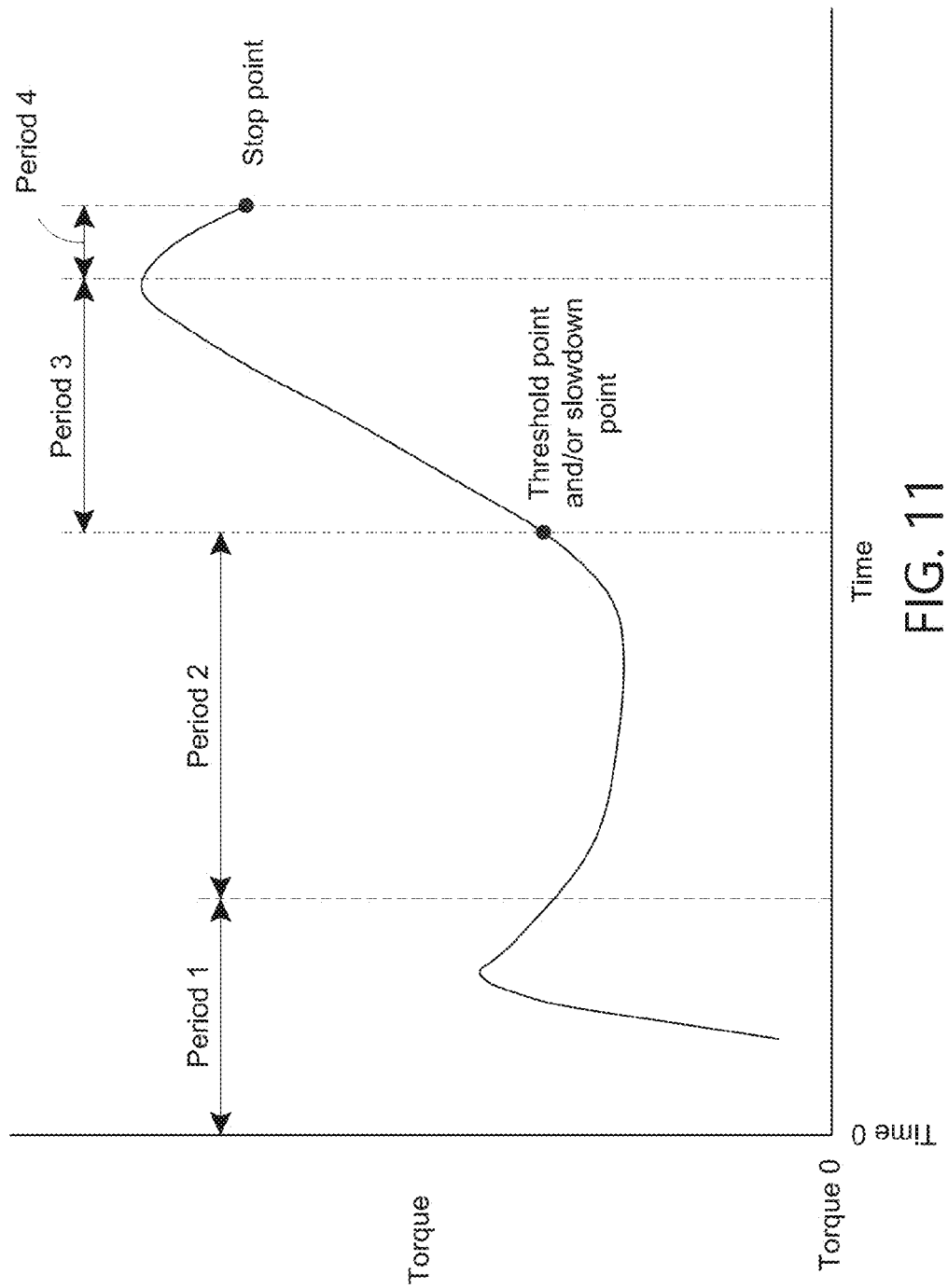
FIG. 11 illustrates a torque plot with threshold and slow-down points.

FIG. 11 shows an illustrative torque versus time curve. As shown, the torque curve can be divided into several periods, such as Period 1, Period 2, Period 3 and Period 4. In some embodiments, Period 1 (e.g., the initial stage as discussed above) includes the initial engagement and entry of the screw into a substrate, such as a bone. During this period, the amount of torque can increase rapidly. Period 1 may also include an increased level of noise and/or unpredictable or unreliable torque data. As such, in some embodiments, the torque data measured during Period 1 is not used to control operation of the driver. Rather, the torque data during Period 1 is ignored or recorded only. Period 1 is thus referred to as a "deadband." In some embodiments, the deadband extends for at least about 50 ms and/or less than or equal to about 200 ms after Time 0 (e.g. the beginning of the screw insertion process at which the screw begins penetrating into the bone). In certain embodiments, the deadband has a duration of less than or equal to about 100 ms (or less than or equal to about 100 ms).

Period 2 occurs at the conclusion of Period 1. During Period 2 (e.g., the second stage as discussed above), the screw is in the process of threading into the substrate and may experience less torque than the initial torque experienced during Period 1. In some variants, the torque data of Period 2 is not used for torque-limiting purposes but is recorded or logged.

In Period 3 (e.g., similar to the third stage and about the first half of the fourth stage discussed above), the torque on the screw can increase. This is because, for example, the screw engages a plate, and begins tightening the plate against the bone. In some embodiments, a threshold point (e.g., threshold condition) is reached during insertion of the screw, such as at or near the beginning of Period 3. In some embodiments, the screwdriver 100 renders torque-limiting functionality activatable in response to reaching the threshold point. For example, if a torque-limiting condition is experienced prior to reaching the threshold point, the torque-limiting functionality is not activated. In comparison, after the threshold point has been reached, if a torque-limiting condition occurs, then the torque-limiting functionality can be activated. This can avoid erroneous and/or transitory torque values activating the torque-limiting functionality, which could result in premature stopping of the screwdriver 100 and/or incomplete insertion of the screw. In certain implementations, the threshold point can act as a gate, whereby the torque-limiting functionality can be engaged only at or after the torque applied to the screw reaching the threshold point.

In some embodiments, the threshold point is a function of torque and/or current. For example, threshold point can be a torque value of at least about: 5 N-cm, 7 N-cm, 10 N-cm, 12 N-cm, 15 N-cm, 17 N-cm, 20 N-cm, 25 N-cm, values between the aforementioned values, or other values. In certain variants, the threshold point occurs at a torque of greater than or equal to about 5 N-cm and/or less than or equal to about 15 N-cm (or between about 5 N-cm and about 15 N-cm). In some embodiments, in response to the torque applied to the screw meeting, or exceeding, the torque value of the threshold point, then the torque-limiting functionality is able to be engaged. As noted above, the torque can be determined from the current drawn by the motor 12. In some embodiments, the threshold point is met or exceeded when the electrical current drawn by the motor 12 is at least about: 0.25 A, 0.50 A, 0.75 A, 1 A, 1.25 A, 1.5 A, 1.75 A, 2 A, 2.5 A, 3 A, values between the aforementioned values, or other values. In certain implementations that include a polyphase motor (e.g., a 3-phase motor), the average total forward current of the phases is used in determining the current. Some implementations use a direct-quadrature-zero transformation or Park's Transformation in determining the current.

In some embodiments, the threshold point is a function of time. For example, in certain variants, the threshold point can occur a certain amount of time from Time 0. In some embodiments, the threshold point occurs at least 300 ms (or at least about 300 ms) and/or less than or equal to 500 ms (or less than or equal to about 500 ms) from Time 0. In certain variants, the threshold point occurs at greater than or equal to about 200 ms (or greater than or equal to about 200 ms) after Time 0.

With continued reference to FIG. 11, the screwdriver 100 can include a slowdown point (e.g., a slowdown condition). In some embodiments, the screwdriver 100 changes the speed at which it rotates the screw in response to the slowdown point being, or having been, reached. For example, prior to reaching the slowdown point, the screwdriver 100 may operate at first speed (e.g., greater than or equal to about 3600 rpm) and after reaching the slowdown point, the screwdriver 100 can operate at a second rotational speed (e.g., less than or equal to about 900 rpm). In some embodiments, the slowdown results in a delay of the full insertion of the screw of at least about: 0.10 second, 0.25 second, 0.50 second, 0.75 second, 1 second, 1.5 seconds, values between the aforementioned values, or other values. Certain implementations of the screwdriver 100 can increase the total time it takes to insert the screw, such as by at least the aforementioned time values. Other implementations of the screwdriver 100 do not increase the total insertion time. For example, some variants increase the insertion speed (and reduce the insertion time) before the slowdown point a sufficient amount to counteract the reduction in speed (and increase in insertion time) after the slowdown point.

Reducing the insertion speed (e.g., rotational speed) of the screw can be beneficial. For example, this can reduce the rate at which the torque increases during insertion of the screw. In some embodiments, reducing the insertion speed improves monitoring and/or resolution of the torque applied to the screw by the screwdriver 100 during the screw insertion process (e.g., during Period 3 and/or Period 4), such as by providing additional time for the processor 22 and/or sensor 18 (e.g., current sensor) to monitor the amount of torque on the screw and/or to determine whether the torque-limiting functionality should be activated or to display the torque to a user. For example, a reduction in the speed from about 3600 rpm to about 900 rpm can increase the duration of Period 3 and/or Period 4 by a factor of about 4. In some embodiments, the slowdown results in an increase in resolution of the monitored torque (e.g., of the motor's current draw detected by the sensor 18) of at least about: 2, 3, 4, 5, 6, values between the aforementioned values, or other values.

In some implementations, the reduction in rotational speed can provide a more accurate and/or precise rotation of the screw relative to the substrate. For example, a reduction in the rotational speed of the motor, drive train and/or screw can reduce the momentum of those components. In some embodiments, this can reduce the likelihood of error, such as error caused by unintended rotation from that momentum. In some embodiments, the slowdown results in the rotational momentum of the screw being reduced at least about: 50%, 100%, 200%, 300%, 400%, 500%, values between the aforementioned values, or other values.

In certain variants, the reduction in speed of the screw can provide an indication to a user, such as a surgeon. For example, the reduction can provide a signal that a certain amount of torque has been reached, that the threshold point has been or is about to be reached (e.g., within less than or equal to about 0.75 second), that the torque-limiting point is about to be reached (e.g., within less than or equal to about 1 second), and/or that the screwdriver 100 is about to stop driving the screw. In some embodiments, the slowdown is accompanied by an indicator, such as the activation of a light (e.g., an LED), an audible sound, or other sensory indicator.

In some embodiments, the slowdown point is a function of torque and/or current. For example, slowdown point can be a torque value of at least about: 5 N-cm, 7 N-cm, 10 N-cm, 12 N-cm, 15 N-cm, 17 N-cm, 20 N-cm, 25 N-cm, values between the aforementioned values, or other values. In certain implementations, the slowdown point occurs at a torque of greater than or equal to 5 N-cm and/or less than or equal to 15 N-cm (or between about 5 N-cm and about 15 N-cm). In some embodiments, the screwdriver 100 engages the speed-reduction functionality in response to the torque on the screw meeting, or exceeding, the torque value of the slowdown point. As previously discussed, the torque can be determined from the current drawn by the motor 12. In some embodiments, the slowdown point is reached when the electrical current drawn by the motor 12 is at least about: 0.25 A, 0.50 A, 0.75 A, 1 A, 1.25 A, 1.5 A, 1.75 A, 2 A, 2.5 A, 3 A, values between the aforementioned values, or other values. Some implementations that include a polyphase motor (e.g., a 3-phase motor) use the average total forward current of the phases in determining the current. Certain variants use a direct-quadrature-zero transformation or Park's Transformation in determining the current.

In some embodiments, the slowdown point is a function of time. For example, in certain variants, the slowdown point occurs a certain amount of time from Time 0. In some embodiments, the slowdown point occurs at least 300 ms and/or less than or equal to 500 ms from Time 0 (or between about 300 ms and about 500 ms). In certain variants, the slowdown point occurs at greater than or equal to about 200 ms after Time 0 (or greater than or equal to about 200 ms).

In some embodiments, the threshold point and the slowdown point are the same point. For example, as shown, both the threshold point and the slowdown point can occur at the beginning of Period 3. In some implementations, this is determined by an amount of time from Time 0, such as at least about: 150 ms, 200 ms, 250 ms, 300 ms, 350 ms, 400 ms, 500 ms, values between the aforementioned values, or other values. In other embodiments, the threshold point and the slowdown point are different points. For example, in some embodiments, the slowdown point occurs before the threshold point; in other embodiments, the slowdown point occurs after the threshold point. In some implementations, the threshold point and the slowdown point are separated by an amount of time (e.g., less than or equal to about 100 ms). In some embodiments, the threshold point and the slowdown point are separated by an amount of torque (e.g., less than or equal to about 3 N-cm).

As illustrated, Period 4 (e.g., similar to about the second half of the fourth stage and the overtorque stage discussed above) begins after Period 3 ends, such as at about the apex of the torque curve. Period 4 can include a decrease in the torque (e.g., a negative torque gradient). This can suggest that yielding and/or stripping of the screw and/or the substrate is imminent or has begun. In some embodiments, the screwdriver 100 monitors the torque data for N consecutive decreasing torque values. For example, in some implementations, N equals 2, 3, 4, 5, 6, 7, or otherwise. In an embodiment in which N is 4, the torque-limiting condition would be satisfied when 4 consecutive decreasing torque values are observed. In various embodiments, after the torque-limiting condition has been satisfied and the threshold point has been passed, the torque-limiting algorithm can instruct that the screwdriver 100 cease turning the screw. For example, power to the motor 12 can be reduced or eliminated.

Figure 12:
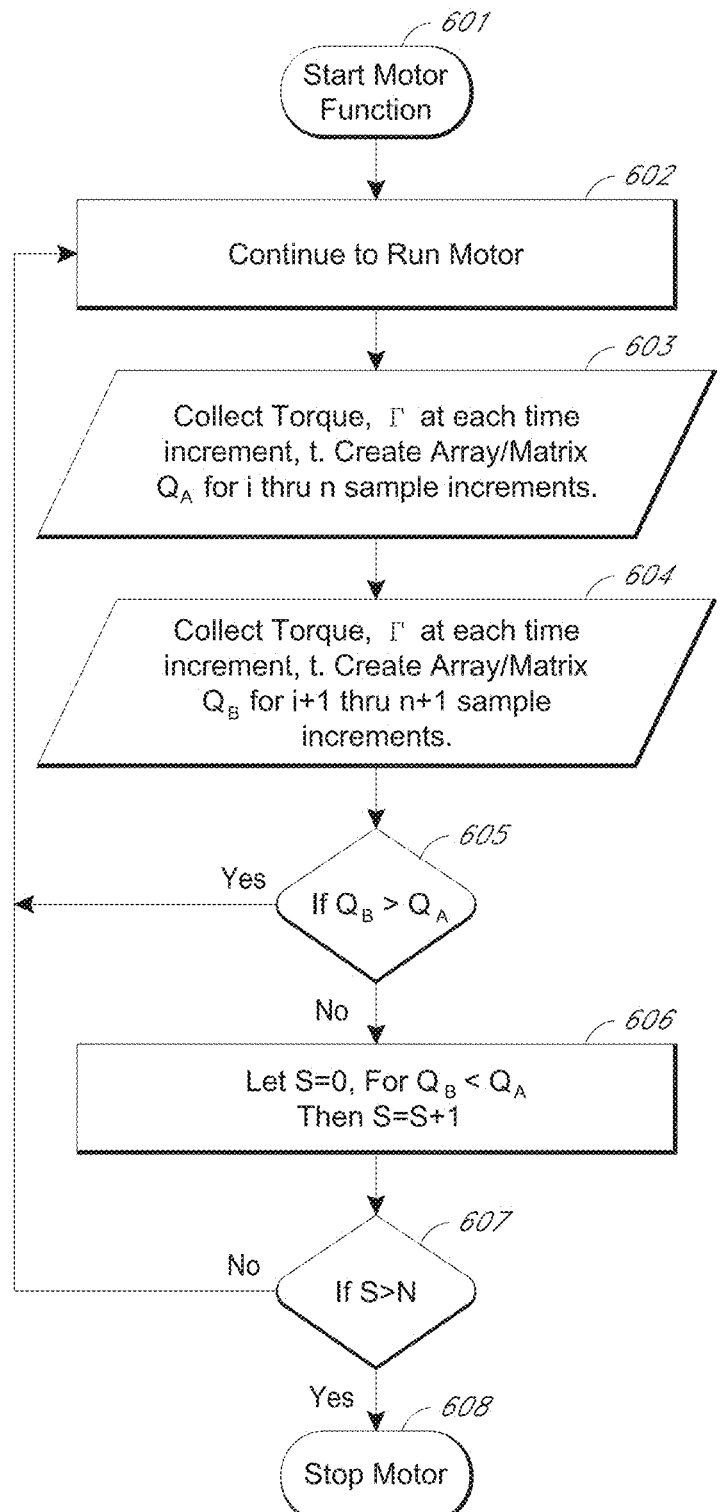
FIG. 12 illustrates a process of monitoring and controlling torque during a screw driving operation.

FIG. 12 illustrates another embodiment of a torque-limiting method and algorithm. In this algorithm:
t is the time increment in microseconds;
I is the current sampling;
Γ is the torque, which is proportional to the current sample;
i is the time increment of the system sample;
n is the array length;
Q is dΓ/dt; and
S is a count variable.
The algorithm can include arrays, such as:

$$\overline{Q}_A = \begin{vmatrix} \Gamma_i & \dots & \Gamma_n \\ t_i & \dots & t_n \end{vmatrix} \overline{Q}_B = \begin{vmatrix} \Gamma_{i+1} & \dots & \Gamma_{n+1} \\ t_{i+1} & \dots & t_{n+1} \end{vmatrix}$$

As illustrated, in a first block 601, the motor 12 can be started. For example, in response to a user activating an input (e.g., a button or switch), the controller 20 on the screwdriver 100 can instruct that power be supplied to the motor 12 to begin turning the screw. In some embodiments, the motor 12 continues to run in at least a second block 602.

In various embodiments, torque values are collected (e.g., observed and recorded). In this regard, various embodiments detect (e.g., with a sensor 18) the amount of current being drawn by the motor 12. This current draw data can be used to determine the amount of torque because the current drawn by the motor 12 is generally proportional to the amount of torque that the motor is applying to a screw being driven by the screwdriver 100. As shown, in block 603, a torque amount at each time increment can be collected and stored in the memory 24. This torque and time data can be used to create an array or matrix $Q_A$ for i through n sample increments. In a subsequent block 604, further torque values can be collected for additional time increments, and that further time and torque data can be used to create another array or matrix $Q_B$.

Some embodiments include a comparison block 605, in which $Q_A$ and $Q_B$ are compared. In certain implementations, if $Q_B$ is greater than $Q_A$, then the algorithm returns to an earlier block, such as block 602. This can allow additional arrays $Q_A$ and $Q_B$ to be created and compared. Accordingly, in some embodiments, the comparison of arrays $Q_A$ and $Q_B$ is substantially constantly occurring in a loop during implementation of the algorithm.

As illustrated, if $Q_B$ is not greater than $Q_A$, then an iterative portion of the algorithm can be performed. In some embodiments, this includes initializing and/or incrementing a count variable S. For example, for each time the algorithm determines that $Q_B$ is not greater than $Q_A$, then the algorithm can proceed to block 606, in which the count variable S is increased by 1.

As shown, in block 607, the count variable S is compared to a preset number N of allowable consecutive decreasing torque values (e.g., 2, 3, 4, 5, 6, or otherwise). For example, if the count variable S is not greater than the number N, then the algorithm can return back to an earlier block (e.g., block 602). Additional $Q_A$ and $Q_B$ arrays can be created and compared in blocks 603-605. On returning to block 605, if $Q_B$ is still not greater than $Q_A$, then the algorithm can proceed to block 606 and the count variable S is increased by 1 again. In various embodiments, if $Q_B$ is greater than $Q_A$, then the count variable S is initialized (e.g., S=0).

In certain embodiments, if the count variable S is greater (or greater than or equal to in some variants) than N consecutive decreasing torque values, then the algorithm proceeds to block 608, in which a torque-limiting function can be activated. For example, the controller 20 can issue an instruction that the motor 12 should be stopped (e.g., by eliminating or reducing the power supplied to the motor). Thus, the torque being applied to the screw can be controlled and/or limited.

According to various embodiments, if fewer than N consecutive decreasing torque values are observed, the motor 12 continues to operate. This can reduce the likelihood that the torque-limiting algorithm will prematurely stop the driving of the screw. For example, by not stopping the motor 12 unless at least N consecutive decreasing torque values are observed, premature stoppage of the motor due to noise in the current signal or transitory torque reductions can be avoided.

In some embodiments, if the count variable S is greater than or equal to a preset number N of consecutive decreasing torque values, then the motor is stopped. For example, if N equals 4, then the motor is stopped when the count variable S is greater than or equal to 4 (e.g., four consecutive iterations through blocks 602-606 in which the torque values decrease each time). Otherwise, in some embodiments, the motor continues running and driving the screw.

Zone of Tolerance and Peak Determination

Figure 13:
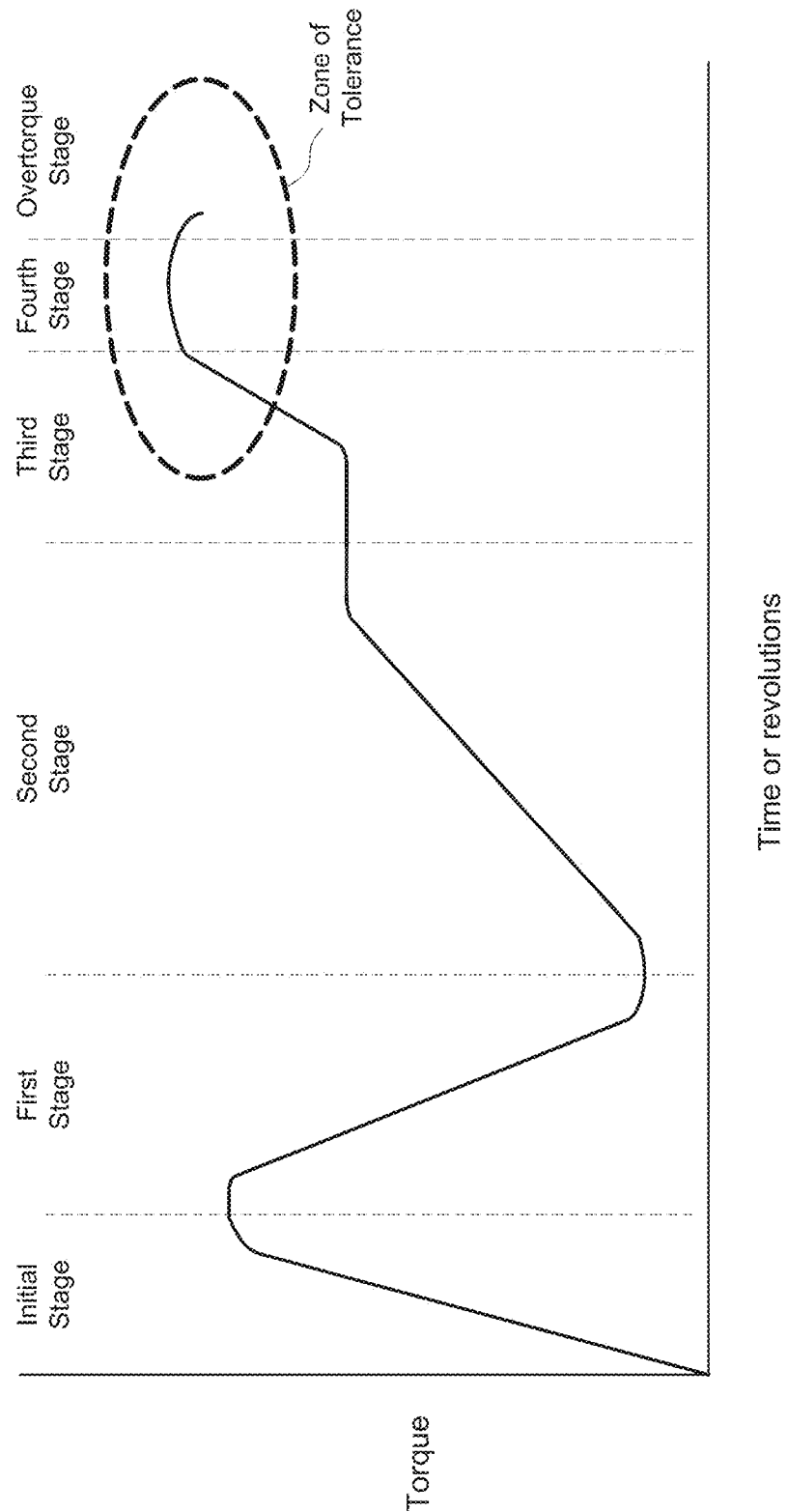
FIG. 13 illustrates a torque plot with a zone of tolerance.
Figure 14:
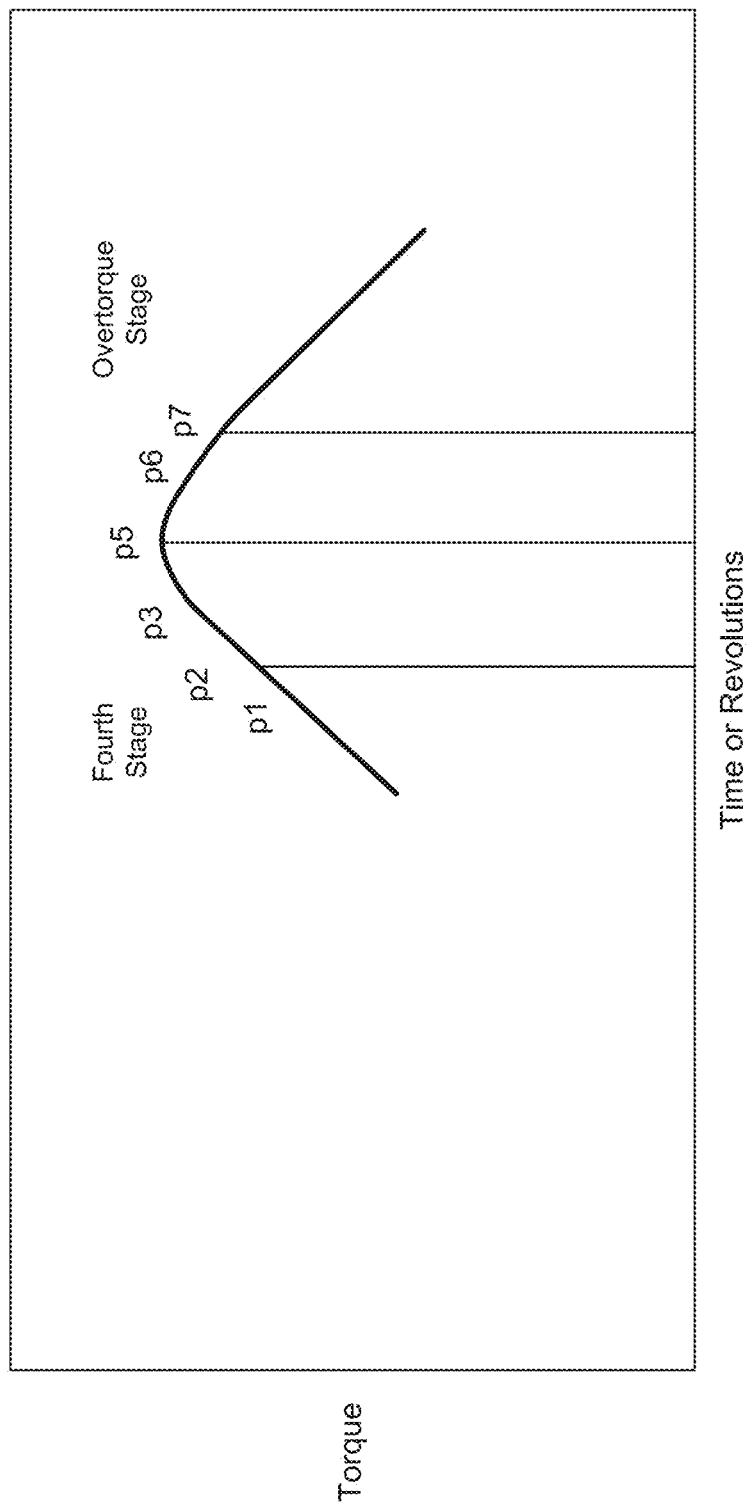
FIG. 14 illustrates a close-up view of an example torque apex.

FIGS. 13 and 14 illustrate a further embodiment of a torque-limiting method and algorithm. As shown, certain embodiments include a "zone of tolerance" prior to and after the apex of the torque curve. Stopping the rotation of the screw in the zone of tolerance can provide confidence that the screw is secured in the bone (e.g., the screw has not been stripped-out).

As shown in FIG. 13, the zone of tolerance can include an inflection point (e.g., the slope changes becomes zero, changes from positive to negative, or otherwise). In some embodiments, the inflection point is in two dimensions, such as torque and time (or revolutions of the screw). Certain implementations of the screwdriver 100 monitor for and/or issue a stop instruction based on the inflection point having been reached. This can enable the screwdriver 100 to stop the motor 12 near, at, or after the inflection point has been reached. In some variants, the motor 12 is partially or completely stopped after the inflection point has been reached and an additional event has occurred. For example, the event can be an amount of torque change (e.g., a torque reduction of at least about: 5%, 10%, 20%, 30%, values between the aforementioned values, or other values), a rotation of the screw occurs (e.g., an additional rotation of at least about: ⅛ turn, ¼ turn, ½ turn, ¾ turn, 1 turn, 2 turns, values between the aforementioned values, or other values), or otherwise.

In some embodiments, the controller 20 can determine the zone of tolerance by monitoring the torque for a number of consecutive increasing torque values and a number of consecutive decreasing torque values. For example, the controller 20 can determine when N1 (e.g., 2, 3, 4, 5, 6, 7, etc.) consecutive increasing values have occurred, followed by N2 (e.g., 2, 3, 4, 5, 6, 7, etc.) consecutive decreasing values. This can indicate that the peak has been reached and that the torque-limiting functionality should be engaged. In some embodiments, one or more torque values separate the consecutive increasing values and the consecutive decreasing values. For example, the torque-limiting functionality can be engaged in response to N1 consecutive increasing values can be detected, followed by one or more interim torque values, followed by N2 consecutive decreasing values. This can account for slight variations in the torque at or near the peak and/or for substantially equal peak torque values.

The zone of tolerance can be further seen FIG. 14's close-up view of an example torque apex. As illustrated, the zone of tolerance can include a positive slope portion (also called the upslope portion), a negative slope portion (also called the downslope portion), or both sides of slope. In some embodiments, the torque-limiting algorithm considers both the upslope portion and downslope portion during the screw insertion process. In certain embodiments, the upslope portion of the algorithm facilitates or ensures securing of the screw, while the downslope portion of the algorithm facilitates or ensures that the screwdriver ceases turning the screw after the torque has reached an apex.

Certain embodiments determine the upslope by determining the change in torque over change in time ($\Delta q/\Delta t$) values during the insertion operation. The method can also include measuring X number (e.g., 2, 3, 4, 5, 6, or otherwise) of torque data points. The method can include rotating the screw and monitoring the torque value until the torque value reaches the peak (e.g., apex). For example, the peak can be determined by comparing $\Delta q/\Delta t$ values at different torque sampling points (e.g., 0, 1, 2, 3, 4), such as can be expressed as: $\Delta q(p0)/\Delta t$, $\Delta q(p1)/\Delta t$, $\Delta q(p2)/\Delta t$, $\Delta q(p3)/\Delta t$, $\Delta q(p4)/\Delta t$, etc. In some embodiments, the peak (e.g., when the value of $\Delta q/\Delta t$ has reached its maximum value) indicates that the screw is secured in place and has compressed the bone plate against the bone. If the $\Delta q/\Delta t$ value is at or near zero, then this can indicate that the screw is secured and/or is at or near the peak torque. As such, in certain embodiments, in response to the $\Delta q/\Delta t$ value being at or near zero, screw rotation is stopped (e.g., by stopping the motor 12).

Similarly, certain embodiments determine the downslope by determining the change in torque over change in time ($\Delta q/\Delta t$) values during the insertion operation. However, in using the downslope to determine the peak torque, the $\Delta q/\Delta t$ comparison looks for $\Delta q/\Delta t$ values that are zero or slightly decreasing (e.g., less than about 5% of the previous value) for N number of consecutive points.

Inflection Points

Some embodiments identify when an inflection point (also referred to as the peak or apex of the torque curve) has been reached or surpassed. The inflection point can occur in the zone of tolerance. FIGS. 15A-15E illustrate various examples of methods and algorithms that can be used to identify when the inflection point has been reached or surpassed and/or to take action in response to the inflection point having been reached or surpassed. For example, similar to the embodiments discussed above, the method can be configured to determine a torque-limiting condition that can be used to activate torque-limiting functionality. This can enable the screw to be seated correctly while also inhibiting the screw from stripping. For example, in some embodiments, the screwdriver 100 can issue a torque-limiting instruction based on the inflection point having been reached or surpassed (e.g., after the deadband). As another example, in some embodiments, the screwdriver 100 can issue a torque-limiting instruction based on the inflection point having been reached or surpassed and after an additional event has occurred. The methods described in connection with FIGS. 15A-15E can include any of the features of the methods described in connection with FIGS. 10-14.

Figures 15A, 15B:
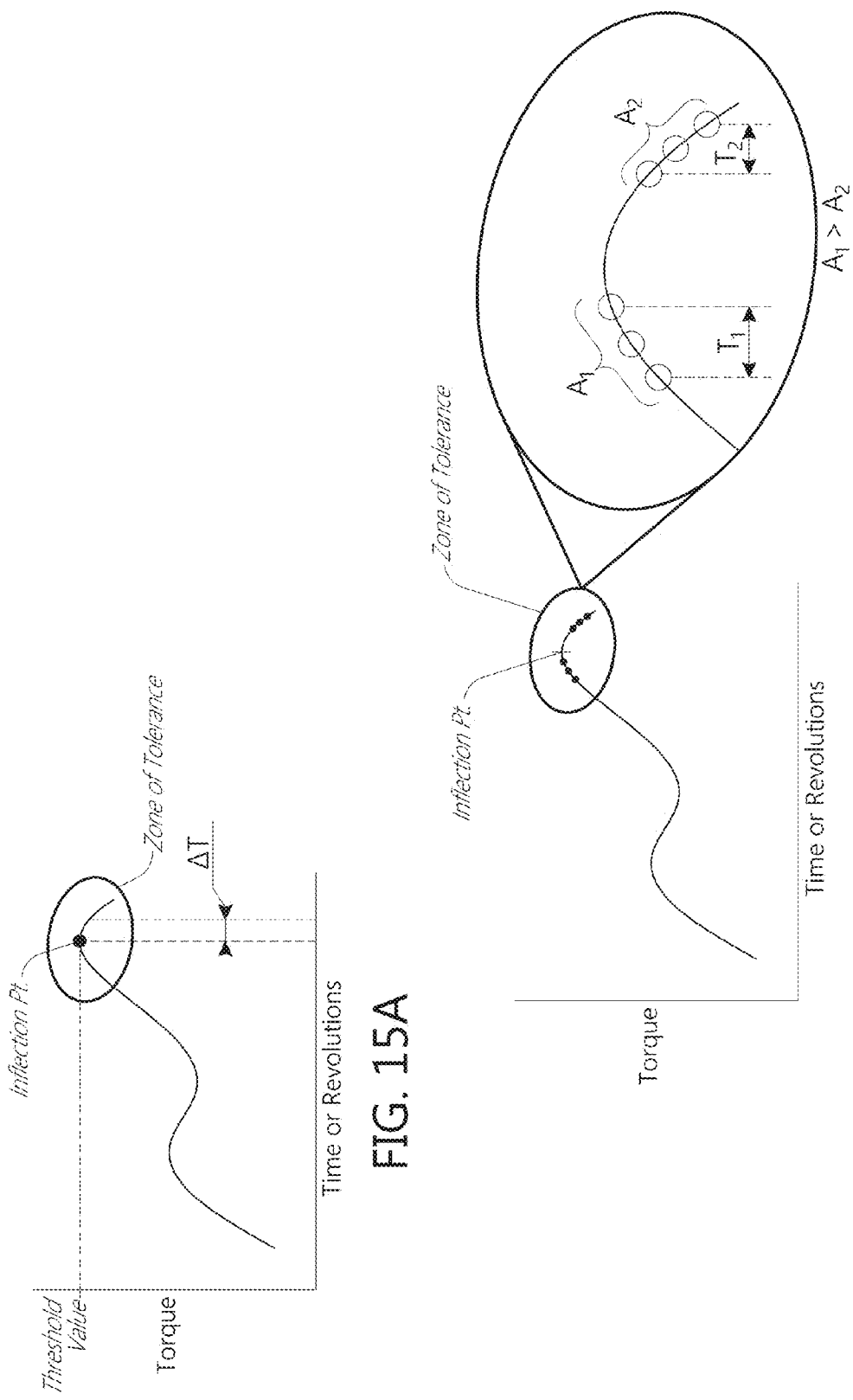
FIG. 15A illustrates a torque plot with an inflection point and a method of issuing a torque-limiting instruction.
FIG. 15B illustrates a torque plot with an inflection point and a method of issuing a torque-limiting instruction.

As shown in FIG. 15A, some methods identify that the inflection point has been reached or surpassed by determining that a torque value is greater than or equal to a threshold value. The threshold value can be an absolute or average torque value. In some embodiments, the threshold value can be the inflection point, and in various other embodiments, the threshold value can correspond to a point on the torque curve at or near the inflection point, such that it approximates the location of the inflection point. In some embodiments, the controller 20 can issue a torque-limiting instruction when the threshold value is greater than or equal to the threshold value. For example, in some embodiments, the controller 20 can slow and/or stop the motor 12 when the threshold value has been satisfied. In some embodiments, the controller 20 can issue a torque-limiting instruction when the threshold value is greater than or equal to the threshold value and after a subsequent time interval ΔT has elapsed. For example, in some embodiments, the controller 20 can slow and/or stop the motor 12 when the threshold value has been satisfied and the time interval ΔT has elapsed.

FIG. 15B illustrates a method of identifying that the inflection point has been reached or surpassed by determining one or more averages and then comparing them. For example, as illustrated in FIG. 15B, a first average $A_1$ of N consecutive torque values over a period $T_1$ can be determined and compared to a subsequently determined average $A_2$ of N consecutive torque values over a later period $T_2$. The sample number N can be any suitable number (e.g., 2, 3, 4, 5, 6, 7, 8, 9, 10, or more than 10). The periods $T_1$ and $T_2$ can have the same or a different duration, and be any suitable value. In some embodiments, the controller 20 can issue a torque-limiting instruction when $A_1$ is greater than $A_2$. For example, in some embodiments, the controller 20 can slow and/or stop the motor 12 when $A_1$ is greater than $A_2$. In some embodiments, the averages $A_1$ and $A_2$ can have overlapping torque values. In some embodiments, one or more torque values can separate the sample of N consecutive torque values in average $A_1$ from the subsequent sample of N consecutive torque values in average $A_1$. A separation between the averages $A_1$ and $A_2$ can help account for slight variations in the torque at or near the inflection point and/or for substantially equal torque values at or near the inflection point. The separation can be at less than or equal to 2, 3, 4, 5, 6, or more torque values.

Figure 15C:
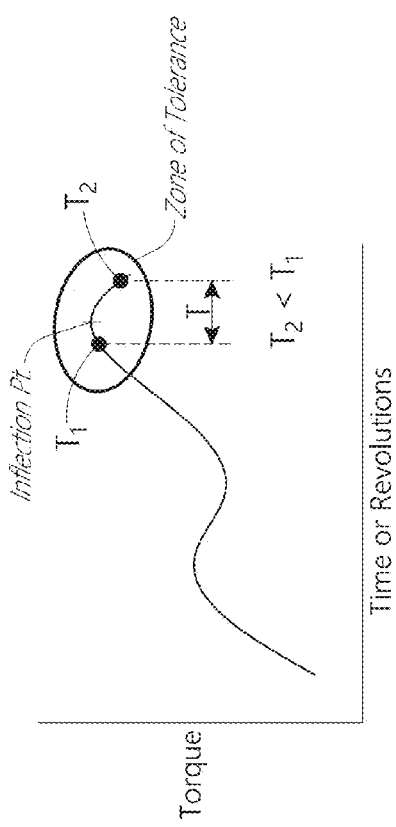
FIG. 15C illustrates a torque plot with an inflection point and a method of issuing a torque-limiting instruction.

FIG. 15C illustrates a method of identifying that the inflection point has been reached or surpassed by comparing first and second torque values (e.g., a current torque value with a previous torque value). For example, as illustrated in FIG. 15C, a first torque value $\Gamma_1$ can be compared to a second torque value $\Gamma_2$. In some embodiments, the controller 20 can issue a torque-limiting instruction when $\Gamma_2$ is less than $\Gamma_1$. For example, in some embodiments, the controller 20 can slow and/or stop the motor 12 when $\Gamma_2$ is less than $\Gamma_1$. In some embodiments, $\Gamma_1$ and $\Gamma_2$ can be separated by period T and $\Gamma_1$ and $\Gamma_2$ can be sampled at any suitable sample interval I. The sample interval I can be less than or equal to the period T. In some embodiments, $\Gamma_1$ is related and/or anchored to a reference value that is less than the expected value of the inflection point. In some embodiments, $\Gamma_2$ can be iteratively measured at every sample interval I and then compared to the same $\Gamma_1$. In some embodiments, $\Gamma_2$ is a current torque value and $\Gamma_1$ is a torque value measured before $\Gamma_2$.

Figure 15D:
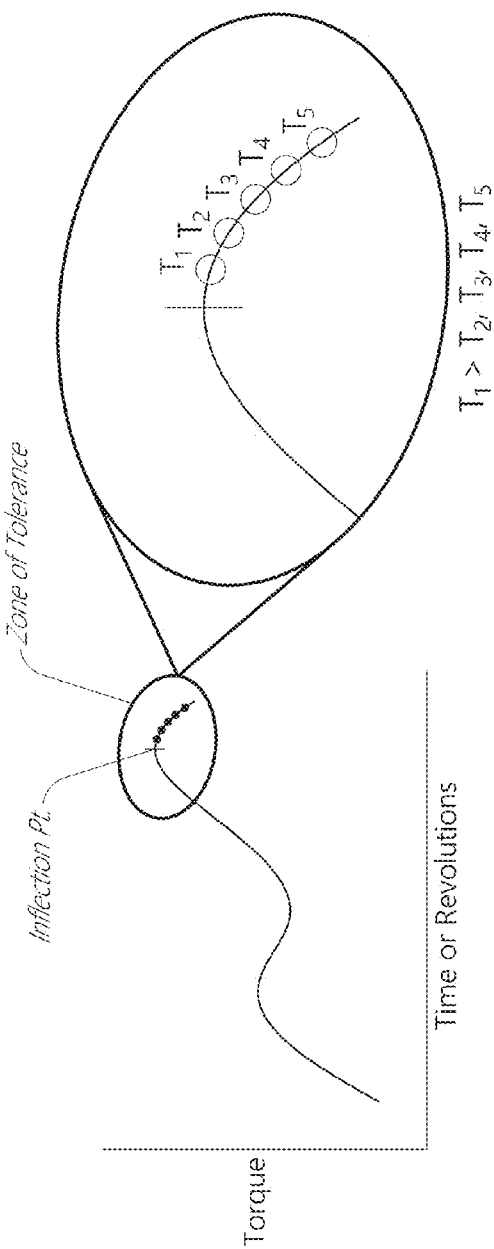
FIG. 15D illustrates a torque plot with an inflection point and a method of issuing a torque-limiting instruction.

FIG. 15D illustrates a method of identifying that the inflection point has been reached or surpassed by comparing the first torque value of a measured sample to one or more subsequent torque values of the measured sample. For example, as illustrated in FIG. 15D, a first torque value $\Gamma_1$ can be compared to four subsequent torque values $\Gamma_2$-$\Gamma_5$ for a sample S having five measurements. The sample S can include any suitable number of measurements (e.g., 2, 3, 4, 5, 6, 7, 8, 9, 10, or more). For sample sizes of 2, the method of FIG. 15D essentially rephrases the method articulated above with respect to FIG. 15C. With respect to FIG. 15D, the controller 20 can issue a torque-limiting instruction when the first torque value $\Gamma_1$ is the largest value in the sample. For example, in some embodiments, the controller 20 can slow and/or stop the motor 12 when $\Gamma_1$ is the largest value in the sample (e.g., when $\Gamma_1$ is greater than $\Gamma_2$, $\Gamma_3$, $\Gamma_4$, and $\Gamma_5$ in FIG. 9D). The measurements of the sample S can be consecutive and can be measured at any suitable sample interval I.

Figure 15E:
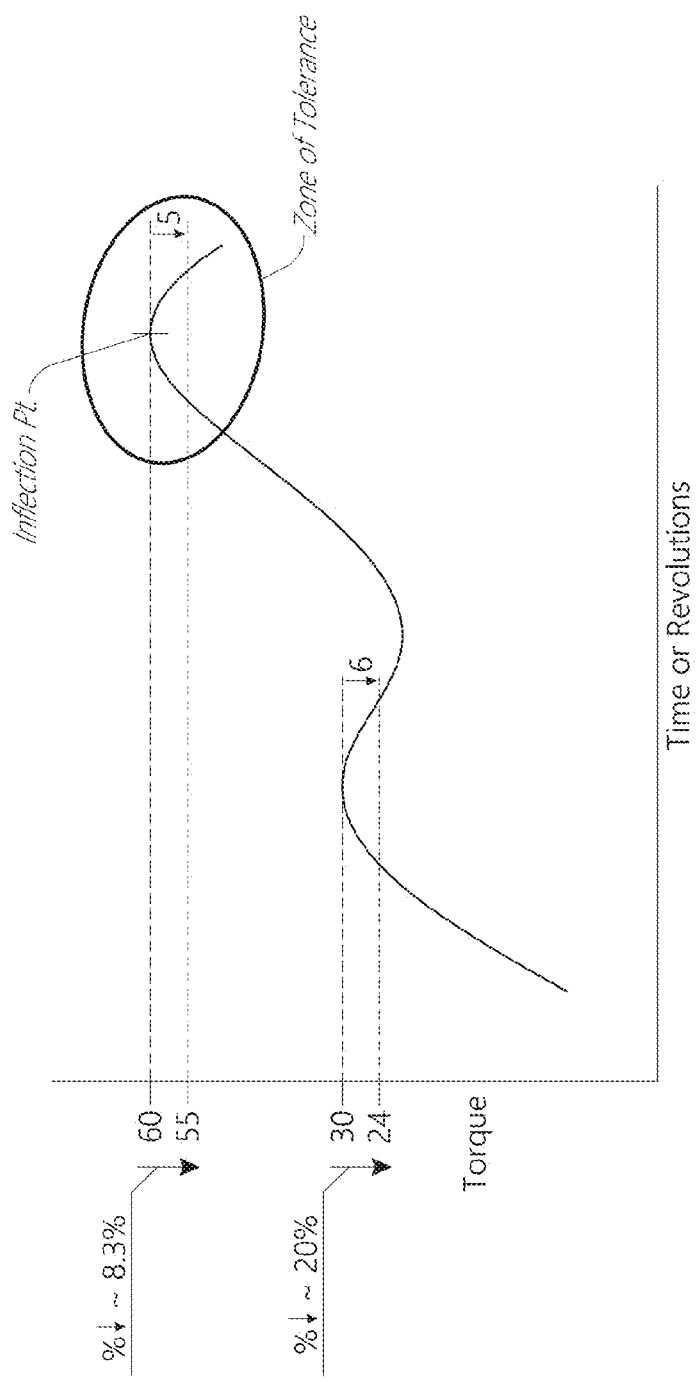
FIG. 15E illustrates a torque plot with an inflection point and a method of issuing a torque-limiting instruction.

FIG. 15E illustrates a method of identifying that the inflection point has been reached or surpassed by determining that a percentage reduction in torque is less than or equal to a threshold percentage (also referred to as a percentage filter). As illustrated in FIG. 15E, the percentage calculation can be triggered when a threshold decrease in torque is measured. In some embodiments, the threshold decrease can be about, 5 N-cm, although any suitable threshold is appreciated (e.g., values outside the aforementioned range). In some embodiments, when a measurement is greater than or equal to the threshold decrease, either the measurement or the threshold decrease can be used to then compute a percentage decrease. If the percentage decrease is less than or equal to a percentage threshold decrease, then the controller 20 can slow and/or stop the motor 12. For example, in some embodiments, the controller 20 can issue a torque-limiting instruction to slow and/or stop the motor 12 when a measured decrease in torque is greater than or equal to a threshold decrease and the percentage decrease in torque computed from the measured or threshold decrease is less than or equal to a threshold percentage.

The percentage threshold can help to differentiate between the peak at the inflection point in the zone of tolerance from other lower value peaks that may occur (e.g., peaks which result from erroneous or transitory torque values and/or the peak between the initial and first stage in FIGS. 8A, 8B, and 8C). For example, in some embodiments, the threshold decrease and percentage threshold can be set to 5 N-cm and 10%, respectively. In such embodiments, if a 5 N-cm decrease is measured from a peak value of, for example, 60 N-cm, the percentage decrease would be about 8.3%. In this case, since the measured decrease of 5 N-cm is greater than or equal to the threshold decrease and the computed percentage decrease of 8.3% is less than or equal to the percentage threshold, the controller 20 would issue a torque-limiting instruction to slow and/or stop the motor 12. However, if in the same example, a 6 N-cm decrease is measured from a peak value of, for example, 30 N-cm, the percentage decrease would be about 20%. In this case, even though the measured decrease of 6 N-cm is greater than or equal to the threshold decrease, the controller 20 would nevertheless not issue a torque-limiting instruction since the computed percentage decrease of 20% is not less than or equal to the percentage threshold. In some embodiments, the threshold decrease and percentage threshold can be established from analysis of a compilation of sample torque curves (e.g., a statistically significant sample of torque curves). In some embodiments, the controller 20 can issue a torque-limiting instruction when the measured decrease in torque is greater than or equal to the set threshold decrease without also computing whether the percentage threshold has been satisfied or exceeded.

Hybrid Functionality

Some embodiments of the screwdriver 100 are configured to operate as a "hybrid" screwdriver, which is a screwdriver having a powered state and a manual state. In the powered state, the motor 12 can power the driver head 104, thereby driving the screw. In the manual state, a user (e.g., a surgeon) can manually turn the screwdriver 100, thereby driving the screw. In some embodiments, a surgeon can easily switch back and forth between the automated and manual operation during a surgical procedure, depending on the particular needs of the surgeon and/or demands of the procedure.

For example, some surgeons prefer to manually begin the insertion of a screw into a patient's bone. Thus, the screwdriver 100 can be configured to enable the user to set the screwdriver 100 in manual mode. This may enable the user to feel more in control and/or can facilitate proper alignment of the screw. After the surgeon has determined that the screw is properly aligned within the bone and inserted an initial amount, the surgeon can switch to the powered mode to further drive the screw into the bone, such as to insert a majority of the screw. This can reduce the overall workload of the surgeon, reduce strain on the surgeon, reduce the chance of stripping the screw head, or otherwise.

Figure 16:
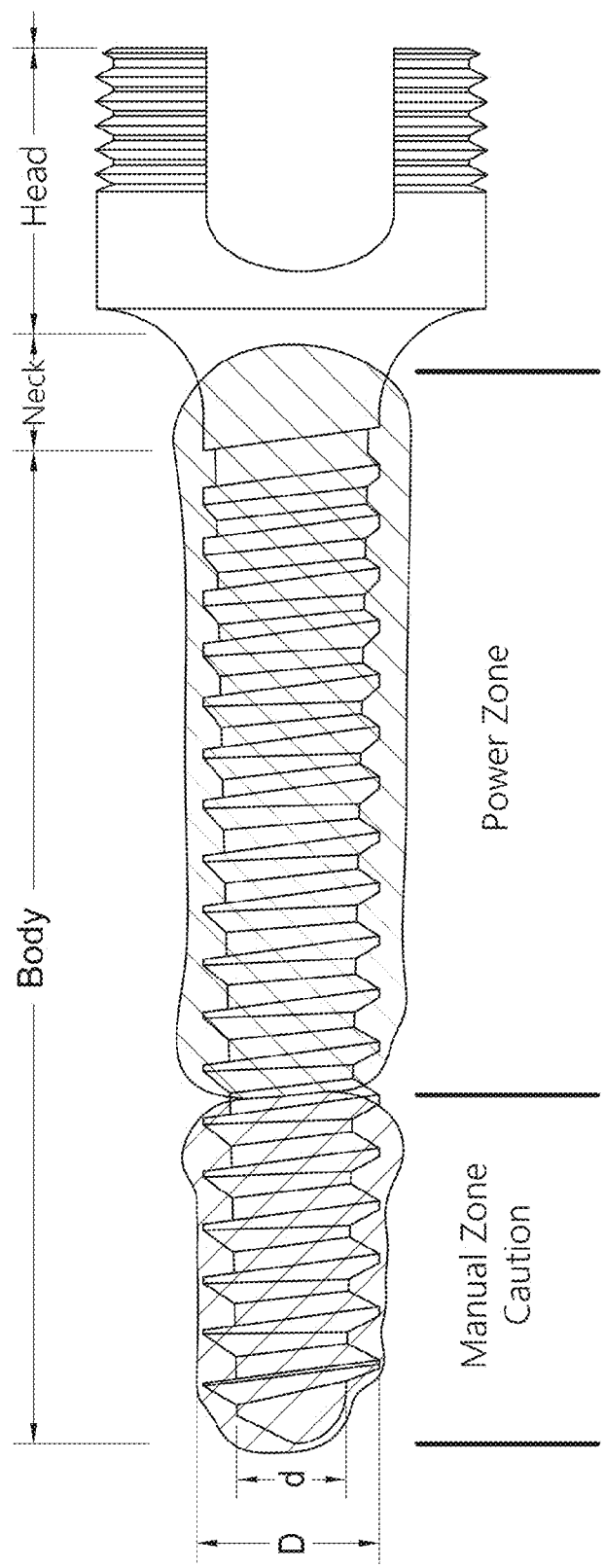
FIG. 16 illustrates a side view of an embodiment of a screw that can be used with embodiments of a screwdriver, with the screw having manual and powered zones.

An example of zones of screw insertion is shown in FIG. 16. As shown, the screw can comprise a "manual zone" and a "power zone." In some embodiments, the beginning portion of the screw (e.g., less than approximately 30% of the screw length) comprises the "manual zone." This area is where a surgeon may wish to manually turn the screw with the screwdriver 100.

In some embodiments, after the screw has been inserted to a depth beyond the "manual zone", the screwdriver 100 can be switched to the powered mode. The surgeon can then use the screwdriver's motor to drive the screw through the "power zone" of the screw shown in FIG. 16. The "power zone" can include a majority of the screw length (e.g., at least approximately 70%).

Embodiments of the screwdriver 100 can save significant effort and/or provide other benefits. Many bones, especially in the spinal region, are very dense and require significant effort to manually screw in the screw. Thus, by having a motor perform a large portion of the work associated with driving the screw, the screwdriver 100 can reduce fatigue by the surgeon, strain on the surgeon's body, etc. In addition, the powered operation of the screwdriver 100 can allow for faster surgical procedures, especially if a number of screws are needed to be inserted into a patient. Moreover, by having the powered operation, there is less of a risk of the surgeon providing motion to the screw outside the longitudinal axis (e.g., by accidental rotation during manual use), thereby widening the hole in the bone, damaging the edges of the bone, or stripping the screw.

This can be advantageous for surgical procedures, such as procedures in which radioactive fluoroscopic imaging is commonly used. By using embodiments of the disclosed screwdrivers 100, patient exposure to the radioactive elements can be reduced, especially for children. For example, by including powered mode, surgical procedures can be sped up. Moreover, as surgeons repeatedly perform these types of procedures, they can experience cumulative radiation exposure. Thus, it can be advantageous to reduce the amount of time that surgeons experience the radioactive elements of fluoroscopic imaging.

Further, as embodiments of the disclosed screwdriver 100 may include a torque-limiting function as discussed above, it may again be advantageous for the screwdriver to switch to manual mode after the "power zone." This allows the user to make any final adjustments to the screw after it has been mostly inserted into the patient. For example, if, in the surgeon's opinion, the torque-limiting functionality of the screwdriver 100 stops insertion of the screw prematurely, the manual mode of the hybrid screwdriver can enable the surgeon to add some final manual turns to further insert the screw into the patient.

In some embodiments, a ratcheting mechanism can be used to switch between powered and manual operation of the screwdriver 100. In some embodiments, the ratchet operates only in one direction, such as in the forward (e.g., clockwise) direction. Some embodiments include an inverse over-running clutch mechanism. In some embodiments, a double drive ratcheting mechanism can be used. However, other systems can be used to switch between manual and automatic, and other methodologies do not limit the disclosure. The ratcheting technology can enhance feel and allow a surgeon to leverage the benefits of power and manual device.

In some embodiments, switching from powered mode to manual mode can insert a stop (such as a bar, tab, or tooth) to inhibit or prevent rotation of the motor or any intermediate parts in the transfer assembly (shafts, gears, etc.), thus providing the ability for a user to manually turn the screwdriver 100. When switching from manual to powered mode, the stop can be removed allowing the motor to turn the drive head 104. The particular methodology for switching between manual and powered modes is not limiting, and other methods can be used as well.

In some embodiments, the default setting for the screwdriver 100 would be manual, and it is only upon operation of a particular mechanism that the motor 12 would turn on and powered operation can be performed. By having the default setting set to manual, the screwdriver 100 would not switch to powered without the surgeon purposefully doing so. Therefore, the risk of unintended powered operation of the screwdriver 100 can be reduced or eliminated. Further, by having the default set to manual, this can reduce the chance of the battery being unintentionally discharged and allow for a longer shelf life of the screwdriver 100. However, it will be understood that in other embodiments the default setting may be powered operation.

Different methods can be used for switching from manual to powered control (or vice versa). For example, the body 102 could include a button (similar to buttons 106) that when pushed switches the screwdriver 100 from manual operation to powered operation. When the button is released, the screwdriver 100 can automatically switch back to manual operation. Thus, when a surgeon wishes to run the screwdriver 100 in powered mode, they will hold the button down the entire time. Thus, allows the surgeon to quickly and easily stop the powered mode if needed, providing significant control to the surgeon. In some embodiments, the screwdriver 100 can be pressure activated, and thus when a tip of the screwdriver 100 senses pressure being applied it can automatically start to rotate.

Other methods of switching the screwdriver 100 can be used as well. For example, the body 102 can include other actuation mechanisms such as a lever, switch, touch sensor, heat sensor, or pressure sensor. In some embodiments, the body 102 can have a portion which can be rotated to activate powered mode. As discussed above, with these actuation mechanisms the default can be for manual control and only upon actuation will the screwdriver switch to powered operation. The particular location of these buttons, switches, or other actuation members is not limiting, and can be located on the body 102 at a location that would be easiest for a surgeon to activate.

In some embodiments, the screwdriver 100 can create a self-contained wireless or Bluetooth network that can be accessed by the surgeon, or someone else from the surgical team. Upon request by the surgeon, a member of the surgical team can connect to the wireless network and manually switch the screwdriver 100 to powered mode, such as by pressing on the screen of a smart phone. When the surgical team member releases the phone screen, the screwdriver 100 can switch back to manual. This will allow the surgeon to control the screwdriver 100 while keeping his or her hands free from any additional buttons or other actuation members.

In some embodiments, the body 102 can include other control mechanisms for switching the powered operation of the screwdriver 100 between a "screw mode" and a "drill mode." This can modify the torque-limiting functionality of the screwdriver and provide for different rotational speed/power output/torque depending on what is desired for the surgeon. In some embodiments, the default in drill mode may be powered and the surgeon may not need to further hold down an actuator to turn the screwdriver 100 to powered mode. However, when the screwdriver 100 is switched to screw mode, the default will again be for manual operation.

In some embodiments, the power system for operating the screwdriver 100 may include buck/boost circuitry which can adjust voltage and/or amperage to meet certain conditional requirements. For example, higher torque requires higher amperage, higher speed requires higher voltage. This allows the screwdriver 100 to easily switch between screw and drill mode while maintaining sufficient power to the screwdriver.

In some embodiments, the screwdriver 100 can have a first powered mode to drive a first portion of a screw (such as the portion of the screw that threads into bone) and a second powered mode to drive a second portion of the screw (such as the set-screw portion of the screw). The screwdriver 100 can include a mode switch which allows the screwdriver 100 to switch between the two modes. For example, the mode switch can adjust operational parameters of the driver (speed, torque, etc.) between the two powered modes. In some embodiments, the mode switch can activate a torque limiting algorithm, such as disclosed in U.S. Pat. No. 9,265,551. In some embodiments, the mode switch can be located on the screwdriver 100, such as through a button or switch. In some embodiments, the mode can be switched by wirelessly connecting to the screwdriver 100. Further, multiple modes can be included with varying modifications to the screwdriver 100, such as 2, 3, 4, 5, or 6 different powered modes.

Screw Differentiation and Mapping

In some embodiments, the drive head 104 of the screwdriver 100 may be configured to receive or detect the type of screw that is engaged with the screwdriver 100. In some embodiments, data related to the type of screw can be entered into the screwdriver 100. This can be done manually and inputted by a user. In some embodiments, the screwdriver 100 can access a pre-made database. In some embodiments, the screwdriver 100 can adaptively learn different screw types. This way, the screwdriver 100 may be able to change different features, such as torque or switching from automatic to manual and back, by tracking the number of revolutions of the screw into the patient. Thus, the screwdriver may be able to variably change its operation based on input information.

Screws having markings can be used in conjunction with the screwdriver. For example, as shown in FIG. 16, the screw may be marked to show the different zones (e.g., manual and power zones). In some embodiments, the first 30% of the screw can be colored one color (such as red) whereas the rest of the screw can be colored a different color (such as green). Thus, the markings give a user a visual cue as to when it is less risky to switch to a power mode. For example, if they drive the screw and only see green and they do not feel any issues, the screw is likely properly aligned. In some embodiments, a thick line marking can show the difference between the two zones. In some embodiments, the screwdriver may emit a sound or light or other cue when the screw is safe to use in the power zone.

As mentioned above, certain screwdrivers include a fixed torque value for a specific screw type. For example, for a 3 mm screw, the screwdriver 100 can include a torque limit set at a value that is specific to that type of screw and to the particular type of bone the screw is to be inserted into. For a screwdriver 100 configured to receive and drive three types of screws (e.g., 3 mm, 4 mm, and 5 mm), the screwdriver 100 would include three torque limit values. The values can be determined by experimentation for each screw type with each substrate. For example, in some embodiments, the three types of screws (e.g., 3 mm, 4 mm, and 5 mm) can be mapped to the device to establish insertion measurements specific to each type of screw. Indeed, in some embodiments, any type of screw that is compatible with the device can be mapped (e.g., customer specific screws) to the device to determine its insertion measurements.

For example, in fixed torque-limiting embodiments, the torque limit value of compatible screws can be determined (e.g., the torque limit values for 3 mm, 4 mm, and 5 mm screws). In variable torque-limiting embodiments, as will be described in more detail below with reference to FIGS. 10-15E, various insertion measurements corresponding to different points along a torque curve can be determined. In some embodiments, such mapping advantageously allows the device to be customized for use with many types of compatible screws, both for fixed torque-limiting embodiments and for variable torque-limiting embodiments. In some embodiments, such mapping can advantageously allow many types of compatible screw to be optimally or nearly optimally seated against a bone plate in many types of bone density (e.g., heterogeneous, homogeneous, healthy, and/or osteoporotic bone densities, among others).

Figure 17:
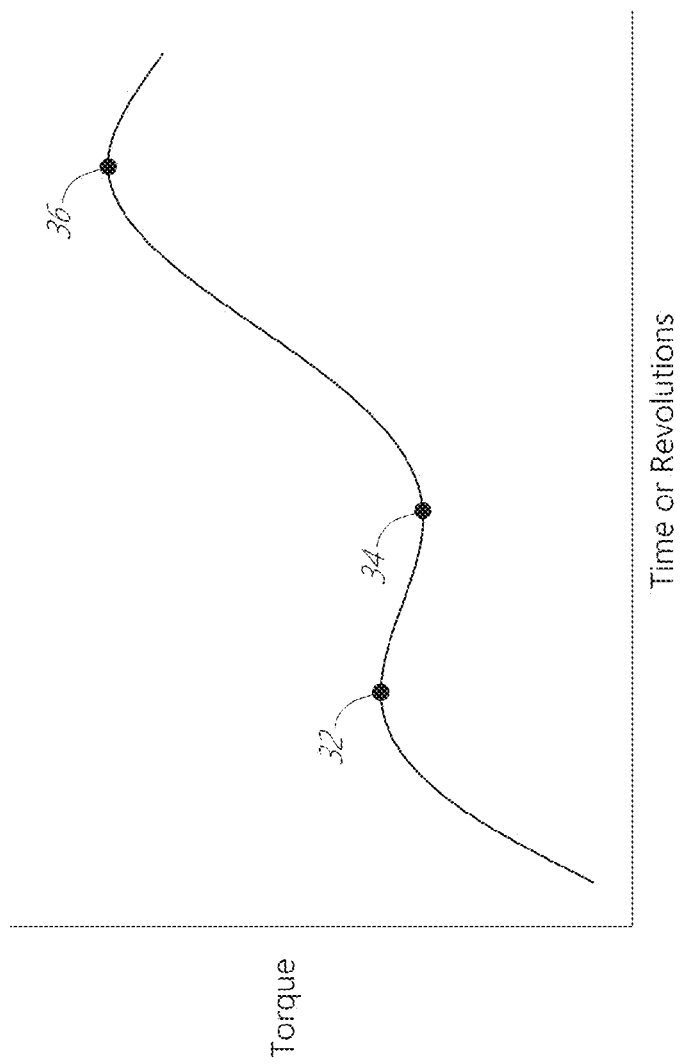
FIG. 17 illustrates three exemplary insertion measurements in relation to a torque curve.

In some implementations, a screw is mapped to the device by screwing it into a known substrate (e.g., cadaver bone sample and/or an anatomically accurate synthetic bone sample) and taking measurements to determine the resultant torque curve. During the mapping process, the bone sample can have any suitable density. In some embodiments, a statistically significant number of the same type of screw is driven into various bone samples to determine its insertion measurements. From the resultant torque curves, various insertion characteristics can be determined. For example, in some embodiments, insertion characteristics can include the initial torque peak (e.g., the torque when the threads initially catch the bone sample), the torque valleys and/or leveling events, and/or the maximum torque during seating. FIG. 17 illustrates, for example, an initial torque peak 32, a torque valley during leveling 34, and a maximum torque during seating 36. However, other insertion characteristics are also appreciated. For example, for pedicle screws, the torque spikes from density transitions can be mapped, such as, for example, by using bone samples with variable densities.

In some embodiments, the data from the above mapping can be stored in the memory 24 and can be referenced before and/or during use. In some embodiments, the insertion measurements can function as threshold torque-limiting conditions that, once satisfied or exceeded, cause the controller 20 to issue torque-limiting instructions to slow and/or stop the motor 12. In some embodiments, the mapped insertion characteristics can function as "guide rails" and/or as backup measurements to the real time torque measurements during insertion into a patient. For example, during insertion of the screw, the mapped insertion characteristics for that type of screw can be used to determine if the screw being inserted is within certain parameters, such as within a percentage of the mapped insertion characteristics. In some embodiments, the percentage is plus and/or minus less than or equal to about: 30%, 20%, 10%, 5%, percentages between the aforementioned percentages, or other percentages. In certain embodiments, the mapped insertion characteristics can be used to identify and/or filter-out measured data. For example, the mapped insertion characteristics can operate as high and/or low filters (e.g., data outside of the mapped insertion characteristics is filtered-out).

As discussed above, screw mapping can address issues that arise because not all screws are the same. By saving (e.g., in memory of the screwdriver 100) a reference for what proper seating of a specific type of screw looks like (e.g., in terms of certain torque curve characterizes), improper driving of the screw can be identified and/or corrective action can be taken. A challenge related to this approach can be how to determine the type of screw that is currently engaged in the device, and therefore which characterizations to reference in the memory.

Figure 18:
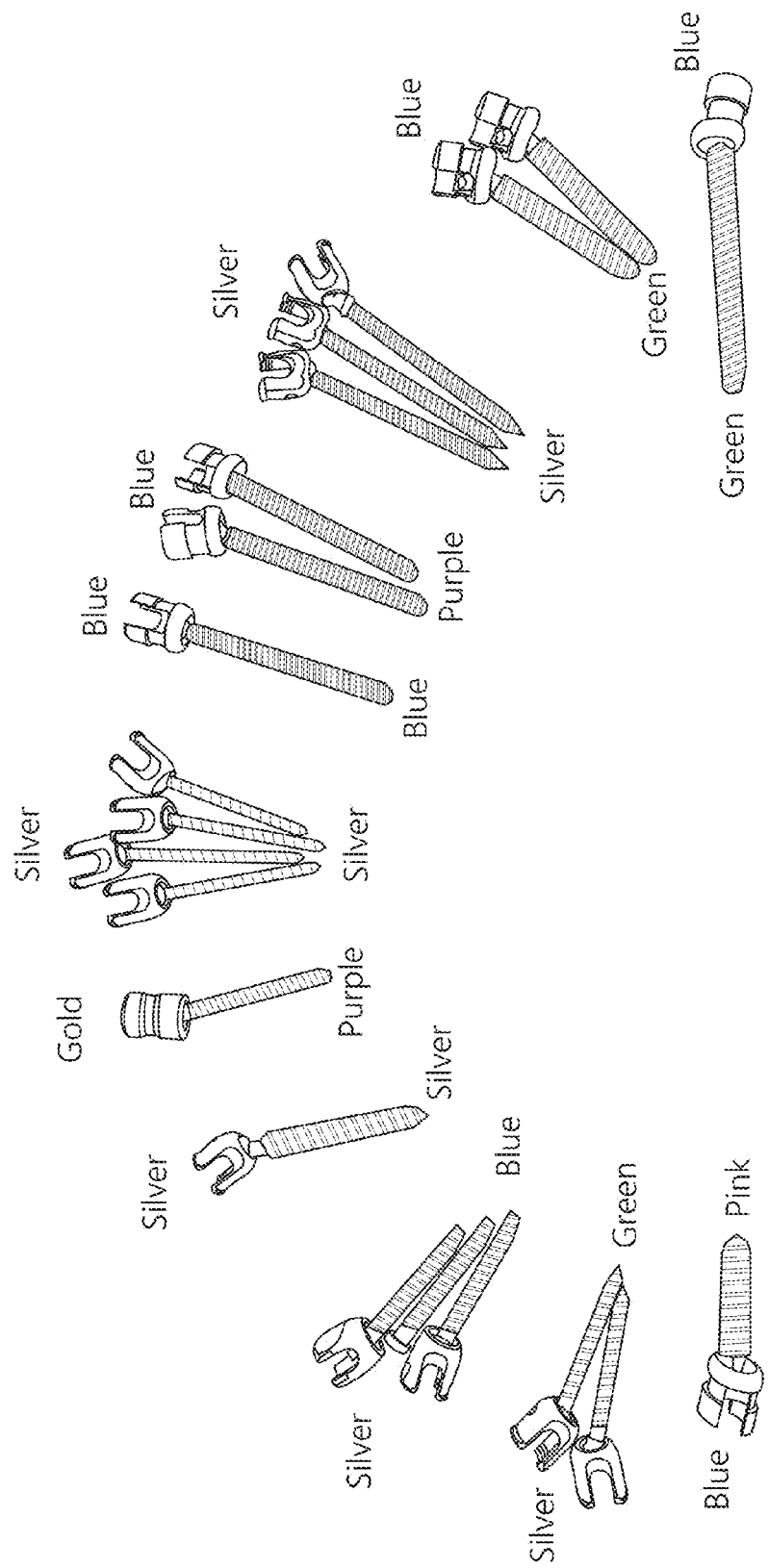
FIG. 18 depicts certain screws with head portions and thread portions, with example colors for the head portions and thread portions indicated.

Some embodiments are configured to recognize the type of screw engaged with the screwdriver based on the coloration of the screw. FIG. 18 depicts certain example screws with head portions and thread portions, with example colors for the head portions and thread portions indicated. As shown, the left-most screw has a blue head portion and pink thread portion. In certain implementations, the screwdriver 100 can be configured to determine the color of the head portion and/or thread portion of the screw. For example, some embodiments use electronic color recognition, such as a light emitting diode (LED) illumination. The LED can be embedded at or near the portion of the device that engaged with the screw. In some embodiments, the screwdriver 100 can include a plurality of photoresistors having different sensitivities to different colors (e.g., light wavelengths). The screwdriver 100 can be configured to determine the color of the head portion and/or thread portion of the screw and to use that color to identify the type of screw. Certain embodiments are configured to access a corresponding mapped screw profile (e.g., torque curve) for that type of screw. The screwdriver 100 can then use the corresponding mapped screw profile to monitor the driving of the screw and/or to identify whether the screw is being driven properly (e.g., substantially consistent with the mapped screw profile) or improperly (e.g., not substantially consistent with the mapped screw profile).

Figure 19:
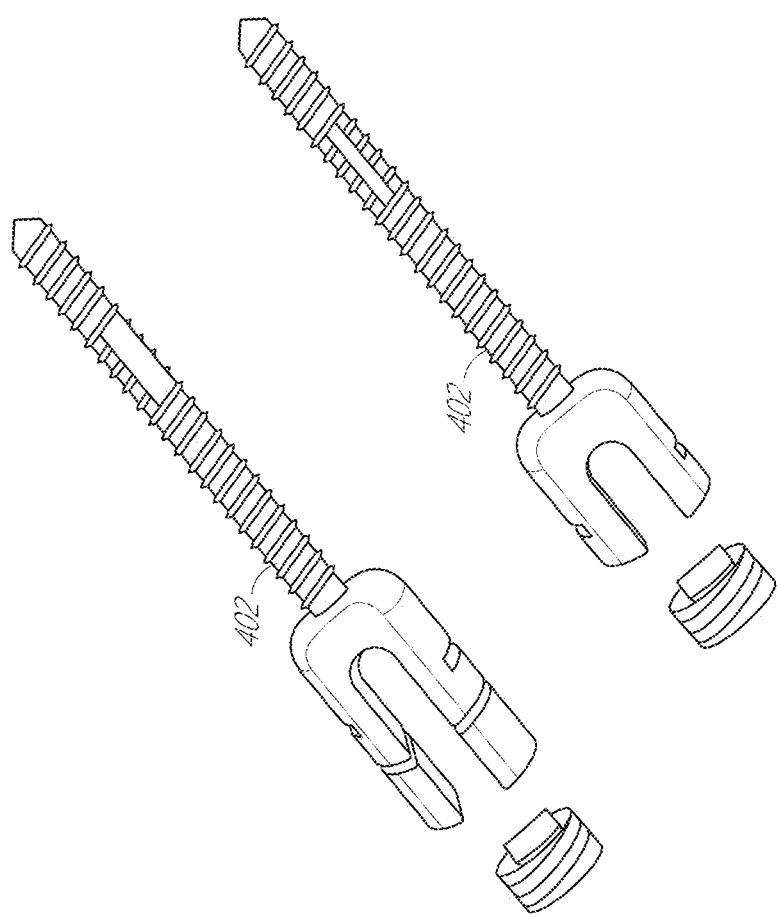
FIG. 19 illustrates two example pedicle screws with set screws.
Figure 20:
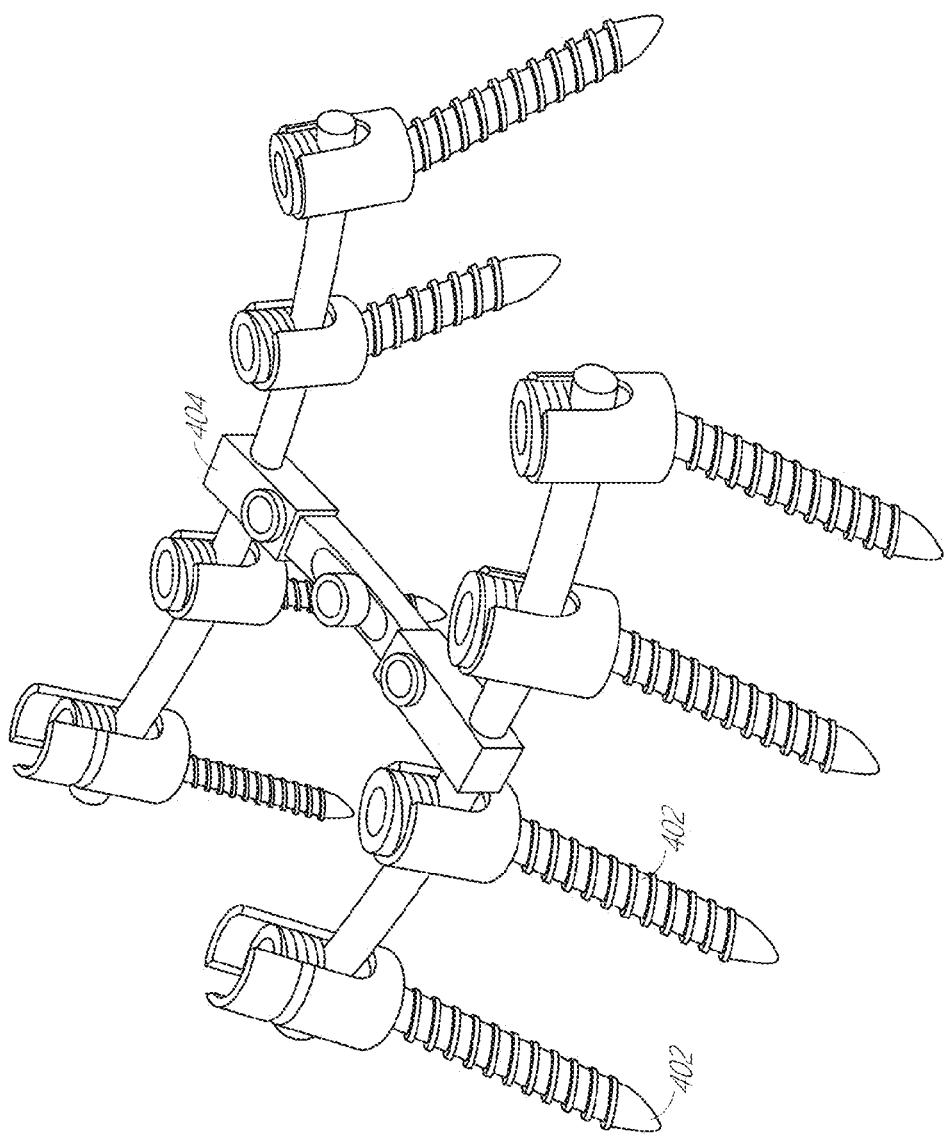
FIG. 20 illustrates an embodiment of a spinal fixation system.

As shown in FIG. 19, some screws include set screws 402. These set screws 402 can hold a fixation rod 404 in place, as shown in FIG. 20. For example, the set screw 402 can tighten the rod 404 against the screw head. The set screw 402 can secure and/or support the fixation rods 404 that are actually performing the therapeutic "fusing" function. The rods 404 can be held in place with set screws 402 that squeeze the rods 404 against the screw head. In some embodiments, the screwdriver 100 is configured to identify proper seating of the set screw 402. For example, the screwdriver 100 can have a mode switch that tightens to a given torque, a mechanical torque limiting ratcheting option, or implements and of the torque-limiting method disclosed herein to identify proper seating of the set screw 402.

Embodiments can set a specific torque for "smart locking" fixing screws that are designed to create a rigid screw plate construct and mitigate risk of screws backing up, which is commonly used as with CMF fixation plates. Further, embodiments can be used for setting specific torque for spinal fixation set screws, setting a specific torque for spinal pedicle screws, and setting a specific torque for extremities fixation screws, and setting a specific torque for CMF fixation screws.

Figure 21:
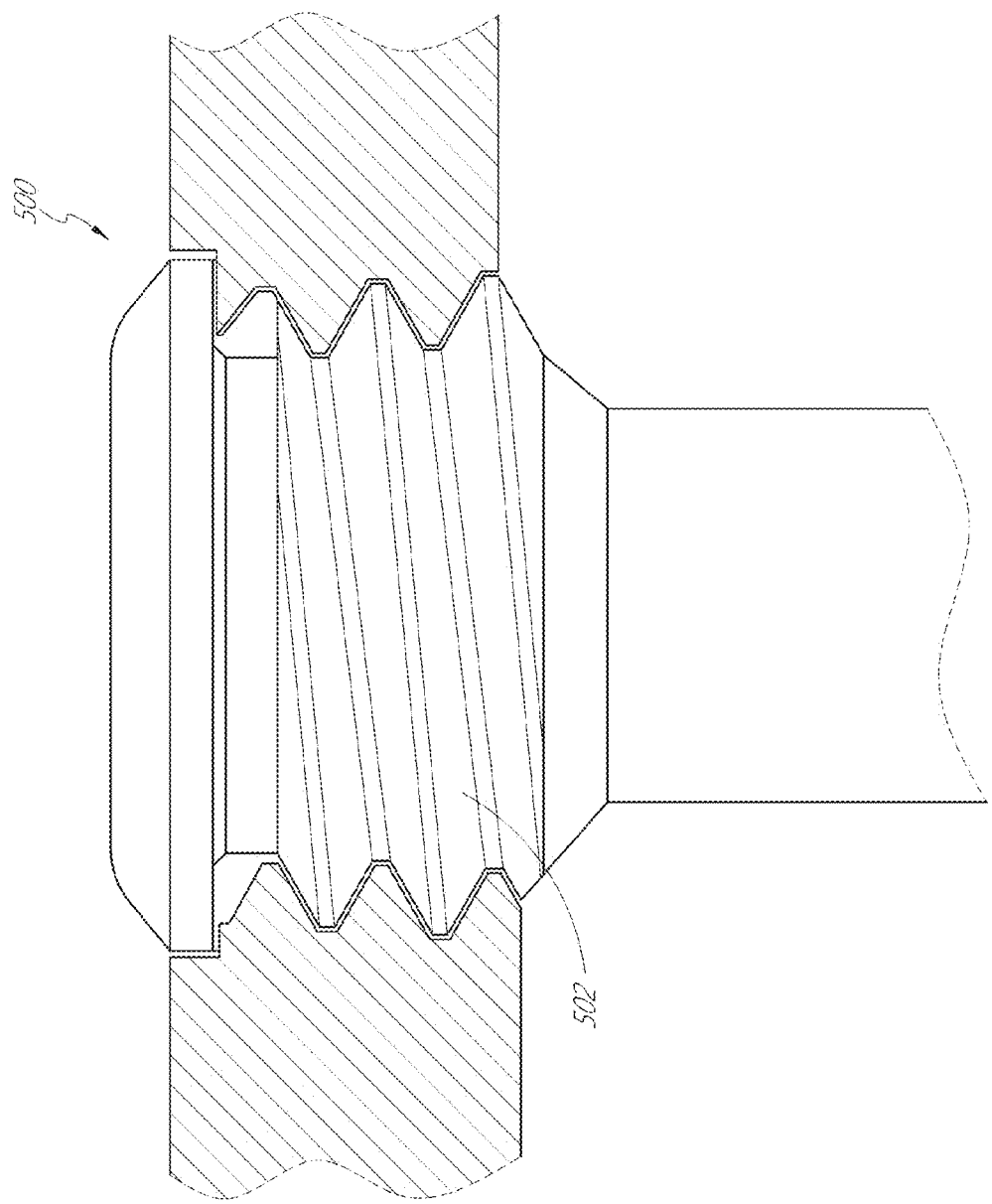
FIGS. 21-23 illustrate embodiments of a smart locking screw.
Figure 22:
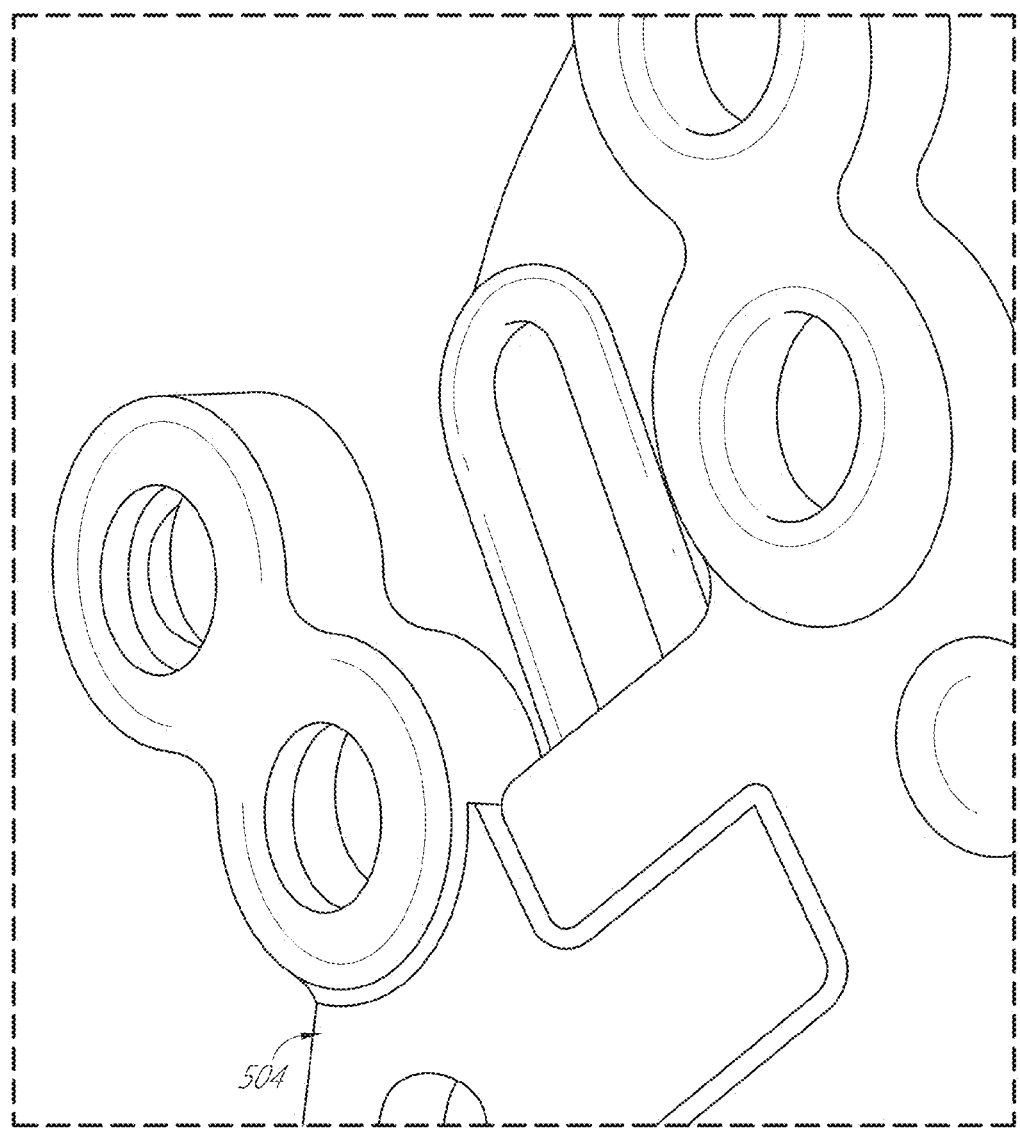
Figure 23:
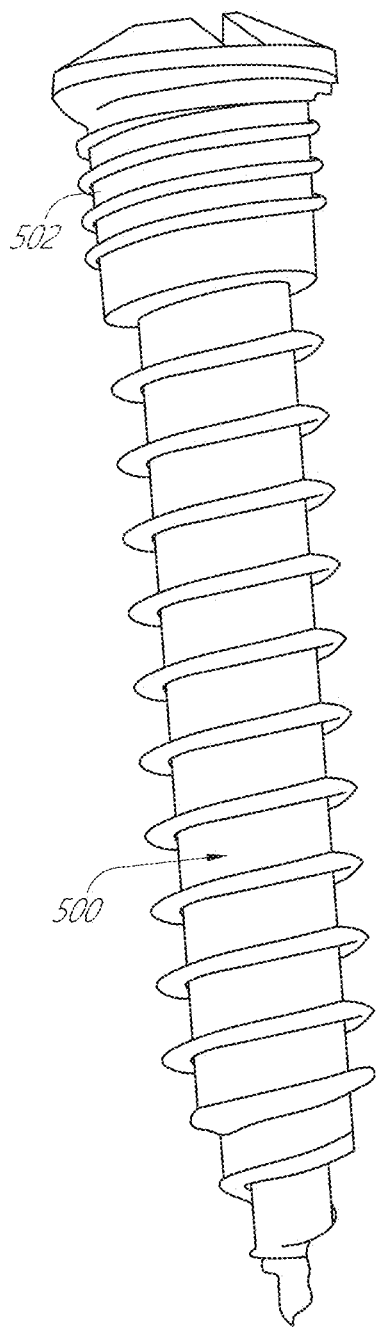

FIGS. 21-23 illustrate embodiments of a smart locking screw 500. In some embodiments, the head 502 of the smart locking screw 500 can have a different thread type and often larger diameter that can be designed to locking into a fixation plate. Surgeons may use power to drive the screw the majority of the way in and use a manual torque wrench to "lock" the screw to the fixation plate 504 shown in FIG. 22. In some embodiments of this disclosure, the smart locking screws 500 can be driven and locked into the plate 504 to a specific torque value. Thus, embodiments of the disclosure are capable of locking smart locking screws 500 to a plate 504 at a specific pre-specified torque value or values Override Functionality Some embodiments of the screwdriver 100 allow a user to override the torque limitation determined by the controller 20. This can be beneficial by permitting the user to override the stoppage of the screw, such as if the screw happens to stop before seating on the plate. In several embodiments, the screwdriver 100 includes an override input, such as a switch, button, or the like. The override input can be configured to send an override signal to the controller 20, which overrides the controller's stoppage of the screwdriver's turning of the screw.

As noted above, certain embodiments of the override input can facilitate seating the screw against the plate. Sometimes, when placing the screw, the screw head remains "proud" of the bone plate (e.g., a bottom surface of the head of the screw remains spaced apart from a top and/or mating surface of the plate). This can result in a less secure mounting of the plate relative to the bone, can inhibit or prevent healing, and/or can cause the patient discomfort. To aid in remedying a proud screw, or for other reasons, the override input can allow a user to rotate the screw an incremental amount, thereby further driving the screw into the bone and more fully (or completely fully) seating the screw on the plate. In certain implementations, the override input momentarily overrides the torque-limiting feature and allows some or all available power to go to the motor 12 to execute the incremental turn. In various embodiments, activation of the override input provides an additional incremental rotational movement of the screwdriver bit of at least about: 45°, 90°, 135°, 180°, 270°, 360°, 540°, 720°, values between the aforementioned values, or otherwise.

In certain embodiments, the override functionality can be engaged whenever the override input is activated (e.g., depressed). For example, some embodiments allow an override for each activation of the override input and/or do not limit the number overrides permitted. In certain implementations, only a limited number of overrides are allowed. For example, some embodiments only allow one override, after which additional override inputs are ignored. In some embodiments, the override input is configured to rotate the screw a predetermined amount (such as about: 1 revolution, ½ revolution, ¼ revolution, values between the aforementioned values, or other values), for each activation of the override input.

According to some variants, activation of the override input allows override operation of the screwdriver 100 for a period of time without requiring additional activation of the override input. This can facilitate convenient operation of other inputs (e.g., controls to drive the screw forward or in reverse) during the override period without the need to repeatedly activate the override input. For example, an override button or other input device can be depressed or otherwise activated to initiate the override time period, during which one or many operations can be performed that would otherwise be inhibited or prevented (e.g., because of the torque-limiting features described above). In some embodiments, the override time period can be at least about: 5 seconds, 10 seconds, 30 seconds, 1 minute, 2 minutes, 5 minutes, values between the aforementioned values, or otherwise.

A variety of override input devices and methods for activating and/or otherwise controlling the override feature are contemplated. For example, in certain embodiments, the override feature is activated by engaging (e.g., pressing and/or holding) a button, or combination of buttons. Some variants include a dedicated button that activates the override feature. Certain embodiments of the override input device include a switch, rocker, slide, proximity sensor, touch screen, or otherwise. Various embodiments can provide feedback (e.g., tactile visual and/or audible) to the user.

Several implementations include an adjustable override input device that can be moved to a plurality of positions to provide different override functionality. For example, the input device can comprise a button, slider, or switch with multiple positions, each with a different override function, such as different operations that are permitted and/or different override time periods.

In some embodiments, the adjustable override input device comprises a wheel or dial that can be rotated between various positions. For example, the wheel or dial can have several (e.g., two, three, four, five, six, or more) positions located a rotational distance apart, such as at least about 45° apart or at least about 90° apart. The screwdriver 100 can be configured to detect the position of the dial or wheel and to provide an incremental rotation of the screwdriver bit or the motor 12 that is about equal to, less than, greater than, or otherwise related to the incremental rotation of the dial or wheel. In certain variants, the incremental rotation of the screwdriver bit is proportional to the rotation of the wheel or dial. In some various embodiments, while rotating the wheel or dial, the user receives tactile or audible feedback, such as distinct "clicks" or detents, such as at each 90° increment.

Certain embodiments have a dial or wheel with multiple positions. For example, the wheel can have three positions that are each located about 90° apart. In some such embodiments, when the dial or wheel is positioned in the first position then the screwdriver 100 will provide a first incremental rotation (e.g., about 90°). When the dial or wheel is positioned in the second position then the screwdriver will provide a second incremental rotation (e.g., about 180°). When the dial or wheel is positioned in the third position then the screwdriver will provide a third incremental rotation (e.g., about 270°).

In some embodiments, the override input device controls the direction of rotation of the bit of the screwdriver 100. This can allow the override input device to control whether the screw is being driven forward or in reverse. In certain variants, the screwdriver 10 drives the screw forward when the override input device is in a first position and reverses the screw when the override input device is in a second position. In some implementations, the override input device is a wheel or dial, and the rotational direction of the screwdriver bit is the same as the direction that the wheel or dial is rotated.

Spinal Applications

Embodiments of the above-described screwdriver can have particular application for the insertion pedicle screws in the spinal context. While the torque restrictions and hybrid applications discussed above can be used with respect to the below described spinal applications, the torque restrictions and hybrid applications can be used with other types of tissues/materials/structures as well and can thus differentiate between the different types of materials.

Figure 24B:
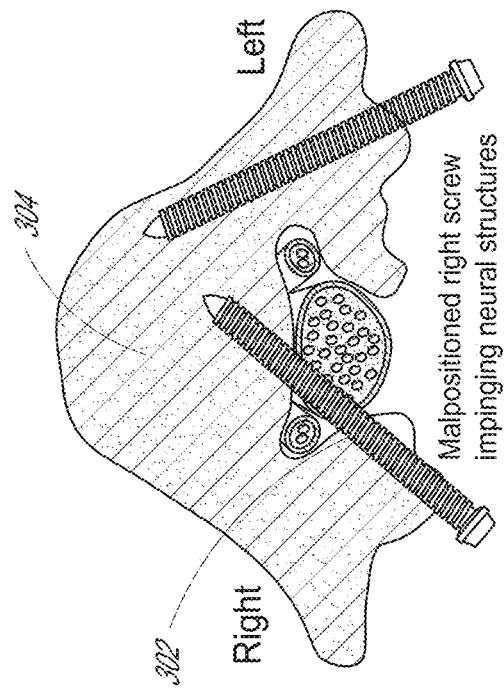
FIG. 24B illustrates a properly placed lumbar pedicle screw and a misplaced lumbar pedicle screw.
Figure 24A:
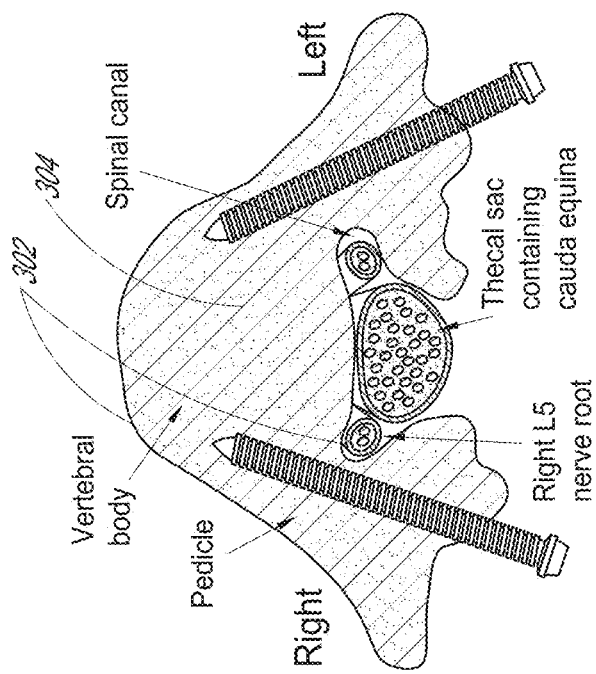
FIG. 24A illustrates two properly placed lumbar pedicle screws.

Proper placement of screws can prevent damage to a patient's spinal area. In some embodiments, the screwdriver 100 can include a system, such as software and hardware as discussed above, which can alert a user that a screw is being placed in an improper area, such as in the improper area of a spine. An example of the screw placement is shown in FIGS. 24A-B. In particular, spinal pedicle screws can require precise placement. The properly placed screws are shown in FIG. 24A, whereas the improperly placed screw is shown in FIG. 24B.

When operating on a patient's spine, the screw will initially pass through a cortical bone 302 having a high density (using higher torque to pass through) and move into the inner cancellous bone 304 having a lower density (using lower torque to pass through). Once in the cancellous bone 304, it would be undesirable for the screw to pass through another layer of cortical bone 302, which would mean the screw is out of alignment or about to pass too far through the spinal cord, such as shown in FIG. 3B. Accordingly, it can be advantageous for a user to know if they were passing through cortical bone, which would likely mean the screw was misaligned.

Accordingly, embodiments of the screwdriver 100 can have a sensing system, such as the above described torque-limiting, that can notify a user if there was a premature spike in torque due to hitting cortical bone 302 that surrounds the spinal cord (e.g., moving out of the cancellous bone 304). For example, the screwdriver 100 can provide an audio or visual indication to a user using the screwdriver 100. In some embodiments, the screwdriver 100 can substantially constantly provide an audio or visual indicator which can change upon hitting cortical bone. In some embodiments, power to the drive head 104 of the screwdriver 100 can be automatically cut off when the premature spike occurs, and thus any driving/drill operations would cease. The screwdriver 100 can include actuators to turn this feature on or off as well. In some embodiments, the disclosed sensing system can cut off power and/or provide visual/auditory indication if there is a sudden increase or decrease of torque due to a breach of the cortical bone (e.g., over a 1% change, over a 5% change, over a 10% change, or over a 20% change from the current torque) (or (e.g., over about a 1% change, over about a 5% change, over about a 10% change, or over about a 20% change from the current torque). In some embodiments, the torque restrictions can be manually set by the user depending on the type of procedure or surgery being performed.

In some embodiments, the screwdriver 100 can include a visual indicator showing which type of bone the screw is in based on the feedback from the screwdriver. For example, the screwdriver 100 can produce a red light when in cortical bone and a green light when in cancellous bone. In some embodiments, a sound may be produced by the screwdriver 100 which is different based on the type of bones. Further, any visual system connected to the screwdriver 100, such as discussed above, may provide indication of the type of bone the screwdriver 100 is in. However, the particular indicator is not limiting.

Figure 25:
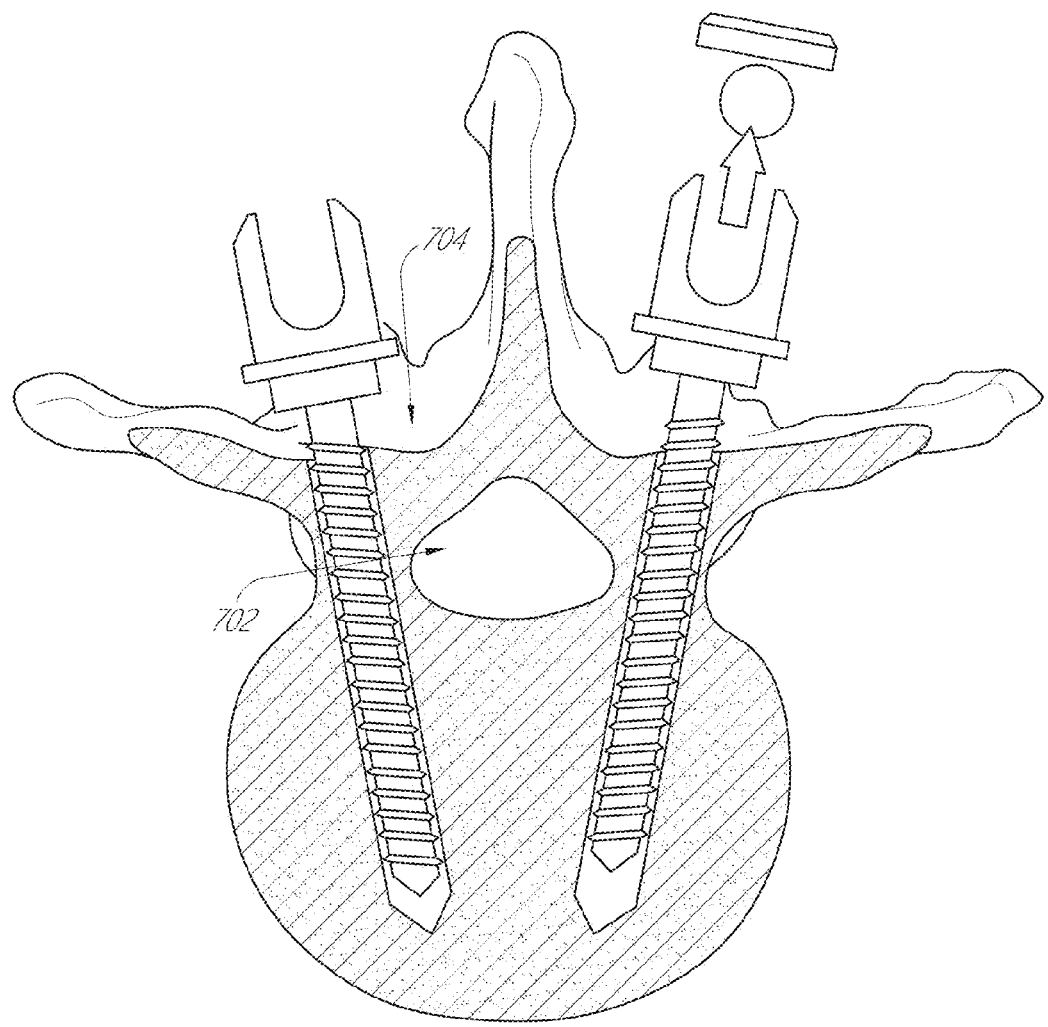
FIG. 25 illustrates a screw travel path in relation to a portion of a patient's spinal column.

As mentioned above, one of the riskiest portions of driving a pedicle screw can be the initial approximately 30% of the driving, such as because of the risk of hitting nerves or the thecal sac. Thus, a user (e.g., a surgeon) can use manual screwing, such as discussed above with the hybrid screwdriver, where the process is slow and careful with feel to the user. As shown in FIG. 25, the gap between the spinal column 702 and the outer vertebra 704 is quite narrow in the early portion of the screw travel. This is when a cortical breach of the spinal column bone, which can cause serious complication, can be most likely to happen. The phrase "breach of the spinal column" can mean "exiting the vertebra." A failed drill or screw installation does not necessarily dictate that the spinal column has been breached. Rather, breach of the spinal column involves the screw or drill blade crossing a second cortical layer. This may indicate that the path does not terminate in the vertebra. Using certain embodiments of the disclosed screwdriver 100, a user can slowly and carefully drive a screw manually through this narrow gap. In some implementations, after the tip of the screw has safely cleared the nerve, the user can switch the screwdriver to powered mode for the remaining portion (e.g., at least approximately 70%) of the screw travel and/or for seating the screw head and/or for applying the torque limiting features.

Substrate Identification and/or Differentiation Overview

In some embodiments, in particular for spinal applications, data inputs (e.g., measurements performed during a portion or throughout a screw insertion procedure) can be used by a screwdriver 100 to make certain determinations. For example, the screwdriver 100 can be configured to use the data inputs to distinguish between and/or identify different types of tissues that the screw is being driven into. This can be called "tissue differentiation." While discussed below in context of spinal application, it will be understood that the tissue differentiation can be used for other purposes.

The data inputs can come from, for example, motor current and/or speed, though other methods of torque measurement can be used as well. In some embodiments, the data inputs comprise a measured torque, which can be data that is derived from or indicative of the torque being supplied by the screwdriver 100. In some implementations, the data inputs comprise current and/or voltage measurements, and an algorithm can be used to convert the inputs into torque values.

As discussed in more detail below, in some embodiments, the screwdriver 100 can use the data inputs, and/or changes in the data inputs, to determine a particular material type that the screwdriver 100 is driving the screw into. For example, the screwdriver 100 can be configured to discern whether the screw is being driven into soft tissue or bone based on the data inputs and/or changes in the data inputs. Further, the screwdriver 100 can be configured to discern between different soft tissues or different bone types (e.g., cortical and cancellous) based on the data inputs and/or changes in the data inputs.

In some embodiments, the data inputs and/or the determinations can be used to adjust operation of the screwdriver 100. For example, an algorithm (e.g., a discrete torque analysis algorithm) can use the data inputs to manage the screw insertion velocity of the screwdriver 100. The algorithm can be used to adjust other characteristics/functionalities of the screwdriver 100, such as voltage, current, rotational speed of the bit, and/or power supplied to the motor. In some embodiments, the measured torque and/or changes in the measured torque can be used to control driving of the screw, such as stopping operation of the motor, changing the driving velocity of the screw, or other changes. This can be similar to the torque analysis algorithm discussed above.

In some embodiments, the changes in torque can be presented (e.g., shown or displayed) to a user. For example, embodiments of the screwdriver 100 can include one or more indicators, such as lights or sounds, which indicate the screw is being driven in a particular torque range and/or that the screw is being driven in a particular tissue layer or type. For example, a first indicator can activate when the screw is being driven into a first tissue type and/or layer, and a second indicator can activate when the screw is being driven into a second tissue type and/or layer. The screwdriver 100 can include a display (e.g., an electronic screen) that displays certain information, such as the torque being applied to the screw, the type of tissue the screw is being driven into, or otherwise. The display can be located directly on the screwdriver 100, or can be through another connected visual device, such as a TV screen or monitor in which the screwdriver 100 is connected to, for example wirelessly or wired.

As discussed in detail below, the torque and/or changes in torque can be measured in a number of different ways. For example, torque measurements can be taken during some or all (and consistently or inconsistently) of the screw insertion procedure. In some implementations, variations between consecutive measurements can be provided to the user. In some embodiments, an alert is provided to the user when the measured torque is outside of a certain range or beyond a threshold. This threshold may be created, for example, by a user inputting a particular torque profile into the screwdriver 100 for a particular procedure. For example, the torque profile could be for the insertion of a pedicle screw and could include pre-programmed thresholds for that particular procedure. Further, changes in the torque or other aspects of the torque, such as the first or second derivatives of torque measurements, may be provided to the user.

The screwdriver 100 can use tissue differentiation in a variety of applications and environments. For example, the screwdriver 100 can be configured to distinguish and/or identify different tissue types during a spinal orthopedic surgery. One type of spinal orthopedic surgery is a spinal fixation procedure (or "fusion"), in which vertebrae are fixedly connected or together, such as with rods or plates that are secured to the vertebrae with pedicle screws.

Figure 26:
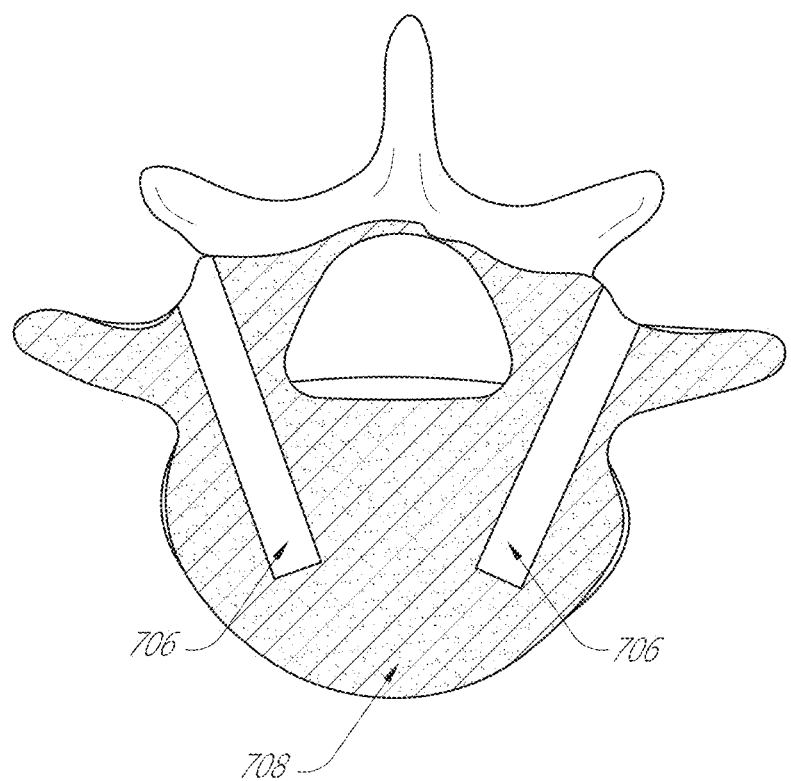
FIG. 26 illustrates a pathway for proper insertion of a pedicle screw.
Figure 27:
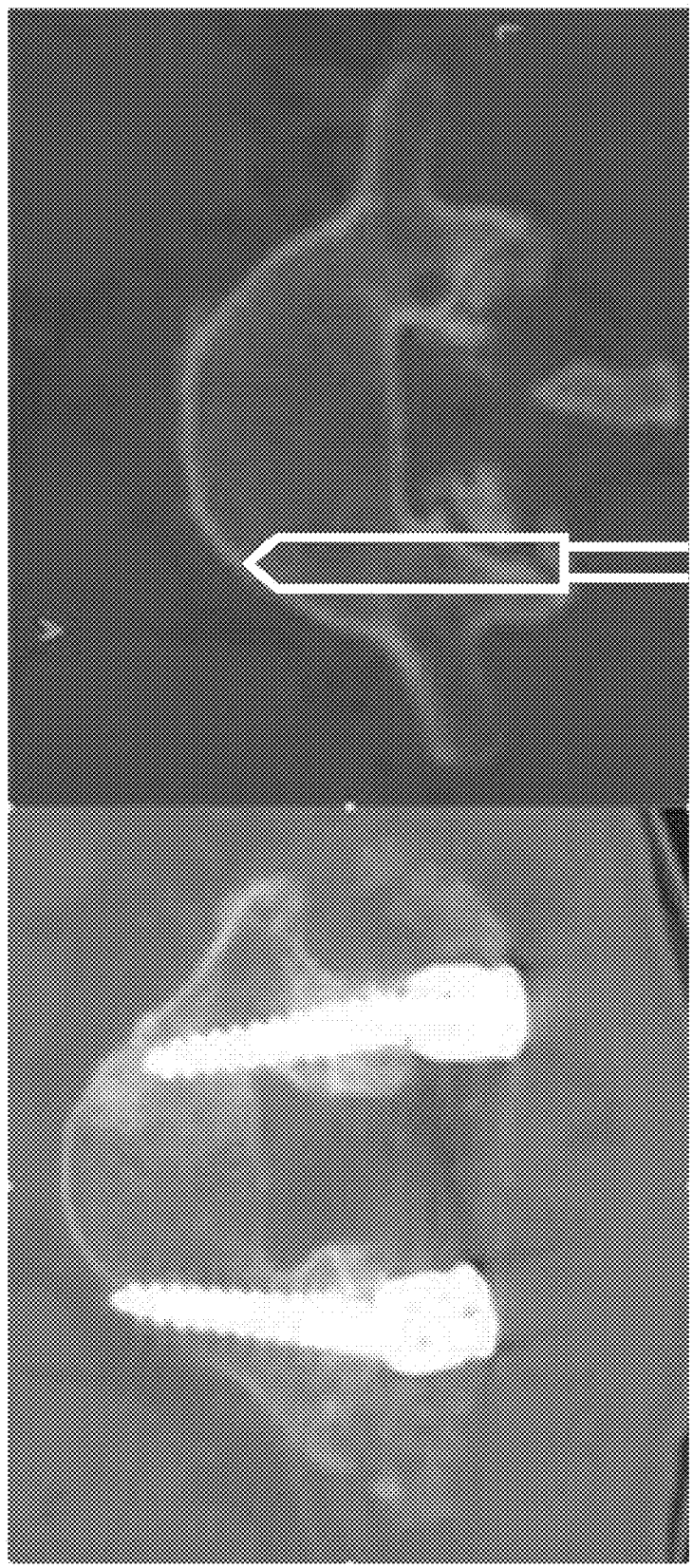
FIG. 27 illustrates X-ray images of examples of an anterior breach.
Figure 28:
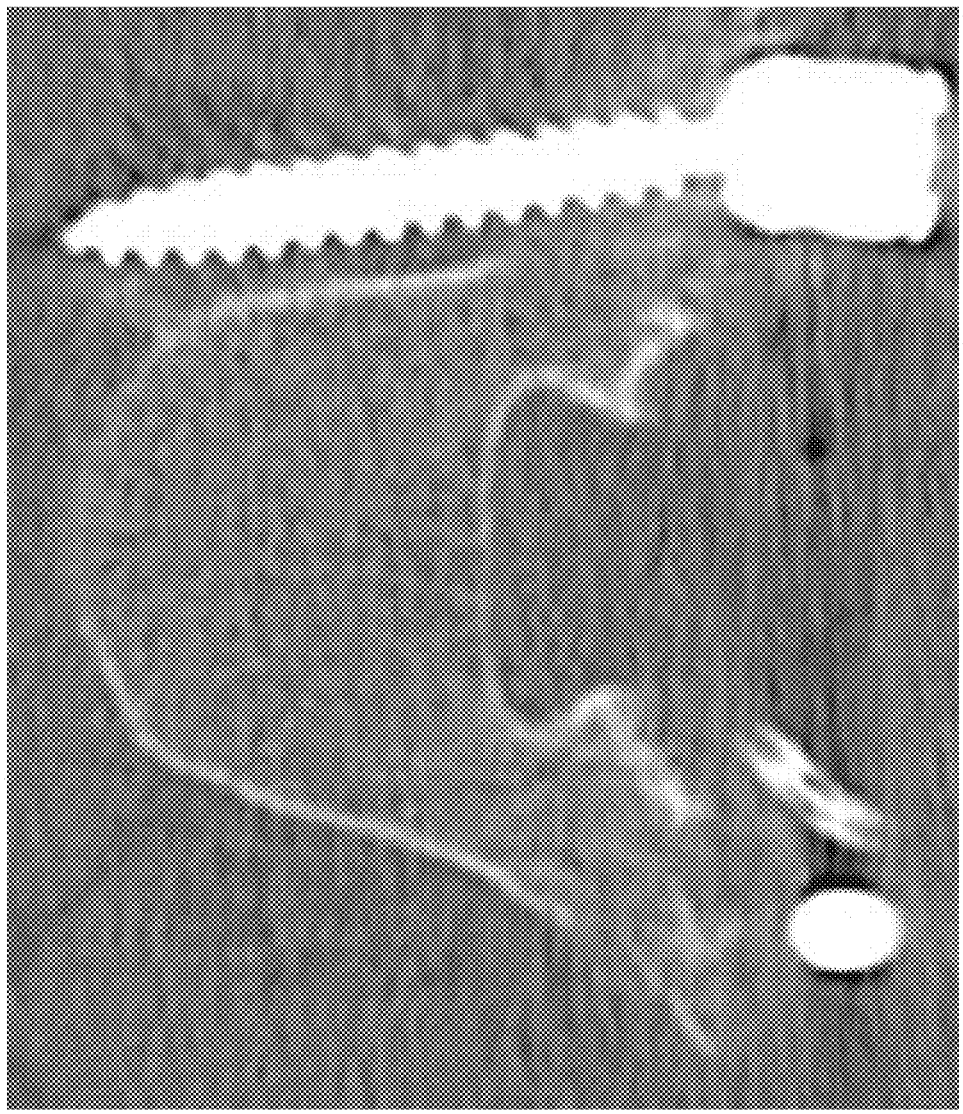
FIG. 28 illustrates X-ray images of an example of a lateral breach.

The pedicle screws can be driven through a narrow pedicle channel 706 in the vertebrae 708, as shown in FIG. 26. This channel can be approximately 15 mm across, though this measurement is not limiting. A cortical breach can result when an object, such as a pedicle screw, breaches the cortical bone surrounding the spinal column, such as shown and discussed above with respect to FIG. 24B. If the cortical breach occurs, the screw could penetrate into the foramen, thereby potentially damaging spinal nerve roots and causing a detrimental outcome for the patient. The breaches can occur in a number of different directions, such as anterior and lateral breaches, as shown in FIGS. 27-28, respectively.

Various embodiments of the screwdriver 100 are configured to reduce or avoid a cortical breach, regardless of the breaching direction. For example, the screwdriver 100 can be configured to inhibit or prevent a breach in the anterior direction (see FIG. 27), lateral direction (see FIG. 28), and/or medial direction. Anterior and lateral breaches may be fairly common and can result in penetrations with significant consequences for a patient, such as pain, nerve damage, or otherwise. In some applications, pedicle breaches are more common in medial direction (e.g., about 74% medial vs. 26% lateral). However, in some applications related to the T3-T8 vertebrae, breaches may occur more often in the lateral direction (e.g., 92% lateral vs. medial 8%).

In some embodiments, the screwdriver 100 can be configured to identify characteristics that indicate a cortical breach is about to occur and can take action to inhibit or prevent a breach, thereby significantly mitigating the risk associated with placement of pedicle screws. In some embodiments, the screwdriver 100 can use a torque curve or profile to identify that a breach is about to occur or occurring, and can take action to respond (e.g., stop driving of the screw) before full penetration of the cortical bone surrounding the foramen occurs. In some embodiments, the motor 12 can be slowed, altered, and/or de-energized before the tip of the screw fully penetrates the cortical bone surrounding the foramen, thereby reducing the chance of damage to sensitive structures in the spine.

Figure 29:
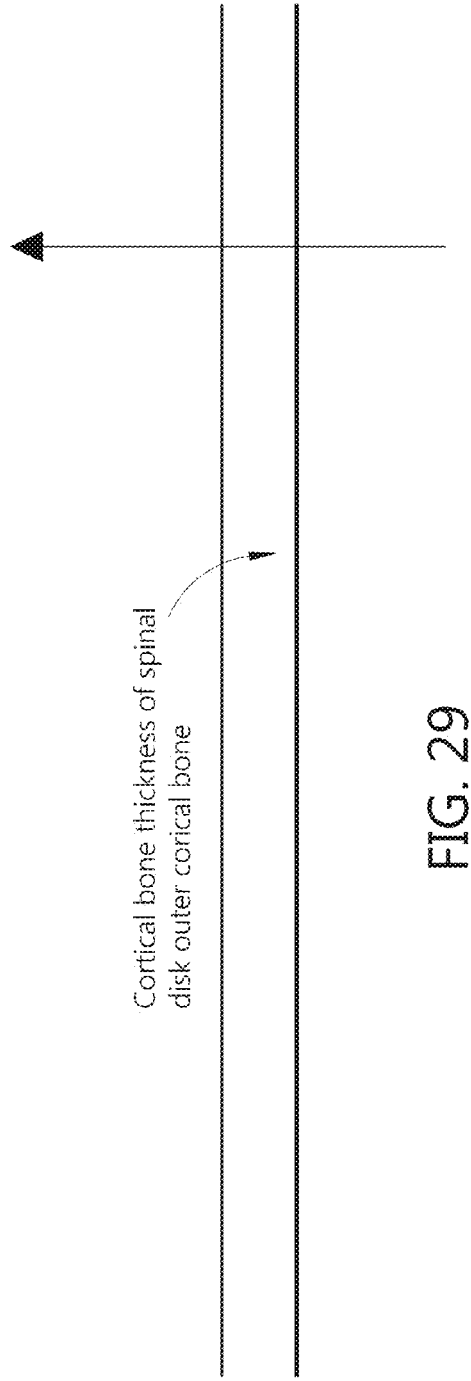
FIGS. 29-30 schematically illustrate screws being driven into different tissues, which can be used for tissue differentiation purposes.

FIG. 29 illustrates a schematic of pedicle screw during insertion. The large arrow in the figure represents the screw path. As shown, the screw passes through the cortical bone that surrounds the outer vertebrae to the cancellous bone that constitutes the inner tissue layer. As cortical bone is harder than cancellous bone, the screwdriver 100 would detect a change in torque, such as from a higher torque level to a lower torque level.

Figure 30:
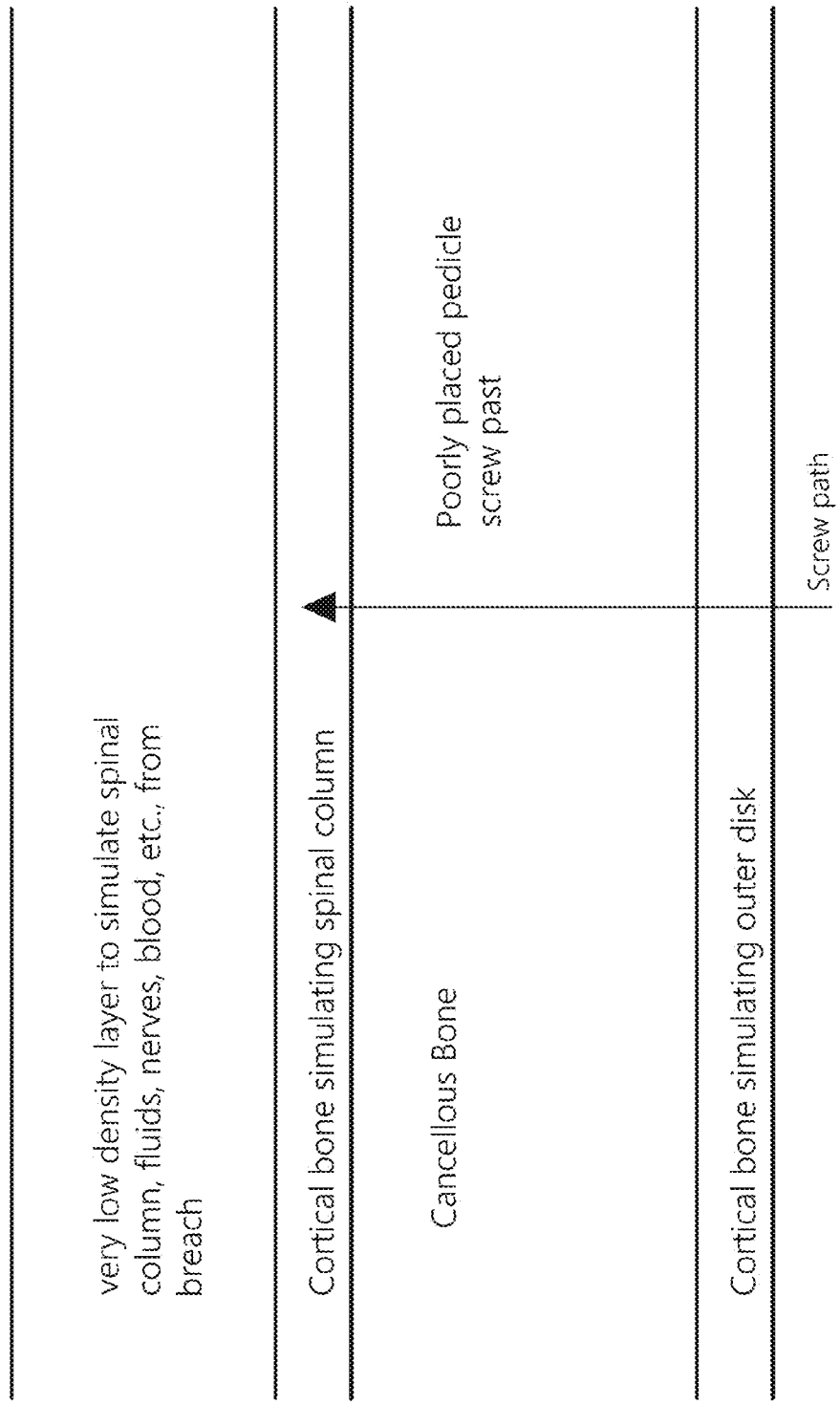

In various embodiments, the screwdriver can be programmed or otherwise configured to correlate a torque value or change to a tissue type or change in tissue type. For example, in the embodiment of FIG. 29, the screwdriver can correlate the reduction in torque to the screw passing from cortical bone to cancellous bone. In some embodiments, the driver receives, such as via a user input, various operational parameters. For example, the driver can receive the number and/or order of tissue types that the screw may encounter during insertion, the corresponding torque values of those tissue types, and/or the torque changes between those tissue types, FIG. 30 illustrates a schematic of the pedicle screw of FIG. 29 that is misplaced and on track to impact cortical bone. Again, the large generally vertical arrow in the figure represents the screw path. As shown, the spinal structure can include three tissue zones and two transitions between. First, the screw would encounter a first layer of outer cortical bone that surrounds the outer vertebrae, followed a first transition to a layer of cancellous bone that constitutes the inner tissue layer. If the screw continues to be inserted, the screw can encounter a second transition zone to a second layer of cortical bone that surrounds the spinal column. Generally, it is advantageous to stop the screw short of fully breaching the second layer of cortical bone to avoid unintentionally damaging tissues within the spinal column itself. Thus, in driving the screw, two different transition zones can be detected by the screwdriver 100. The first zone from higher torque to lower torque (e.g., moving from cortical to cancellous bone) followed by a second transition zone from lower torque to higher torque (e.g., moving from cancellous bone to cortical bone).

In some embodiments, the screwdriver 100 is configured to detect that the screw is beginning to penetrate the second cortical bone layer and to take an action in response. For example, in response to determining that the screw is beginning to penetrate the second cortical bone layer, the screwdriver 100 can stop (e.g., depower) the motor, such as after a certain number of rotations, such as one, two, three, four, or more.

While the discussion above relates to an example of the screwdriver 100 for use in the context of reducing cortical breaches, the screwdriver 100 can be used in other contexts as well. Various embodiments of the screwdriver 100 can be used to characterize other tissues and tissue transition zones, and the particular tissue or transition zone is not limiting. Thus, the screwdriver 100 can be configured for a myriad of applications, both surgical and non-surgical.

Examples of Substrate Identification and/or Differentiation

Figure 31:
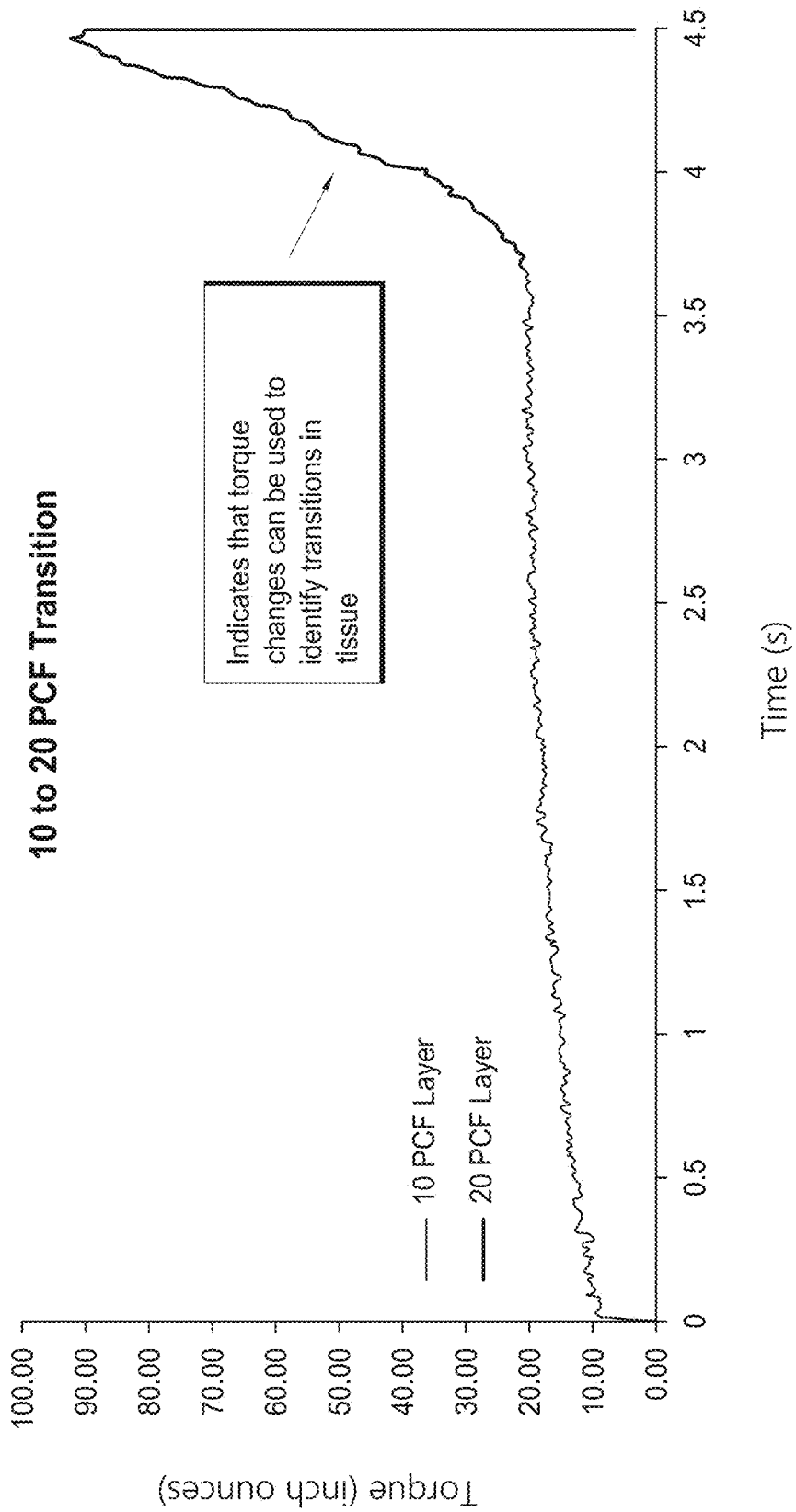
FIGS. 31-51 illustrate various torque curves for a screw being inserted into one or more bone-simulating materials, and certain features of the curves that can be used in operating embodiments of a screwdriver.

FIG. 31 illustrates a torque curve from driving a screw from a 10 pound per cubic foot (PCF) block into a 20 PCF block (e.g., from a less dense to a more dense material). The screw used was a screw for composite wood and wood, square drive, type 316 stainless steel, no. 8, 2" screw, though this is merely an experimental example. As shown, the torque measurements have a transition from the 10 PCF block to the 20 PCF block. This would be similar to transitioning from a less dense cancellous layer (10-15 PCF generally) to a more dense cortical layer (40-50 PCF generally). Accordingly, the screwdriver can use the change in torque (e.g., about: 5%, 10%, 15%, 25%, 30% in the amount of torque applied to the screw) to detect a change in tissue type. In some embodiments, the screwdriver can use the change in a slope of the torque to detect a change in tissue type, such a change of at least about: 25%, 30%, 35%, 40%, 45%, or 50%. In some embodiments, the screwdriver 100 can relay the change of torque information to a user and/or automatically change its function, such as shutting off the motor, as discussed above.

Figure 32:
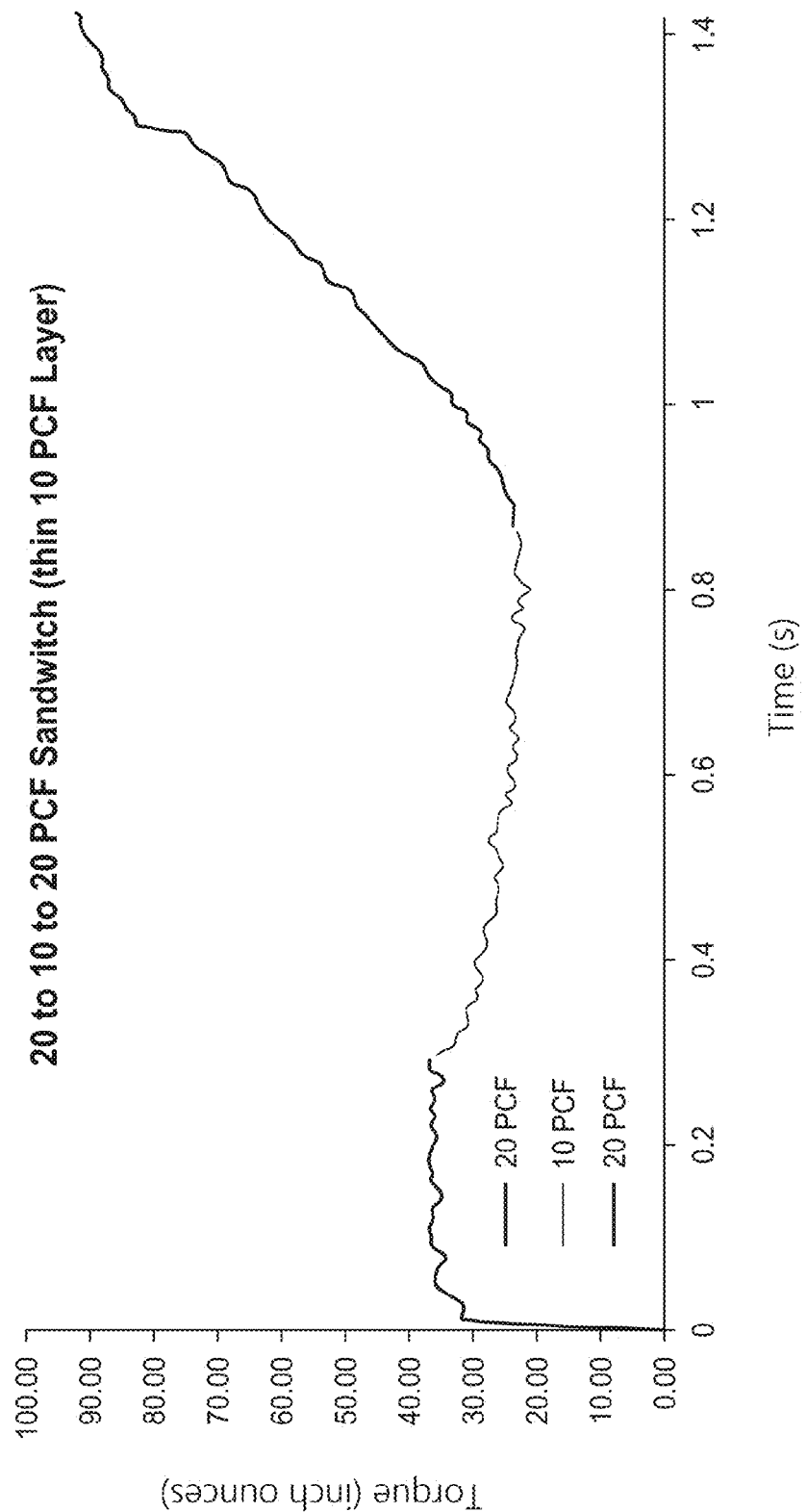
Figure 33:
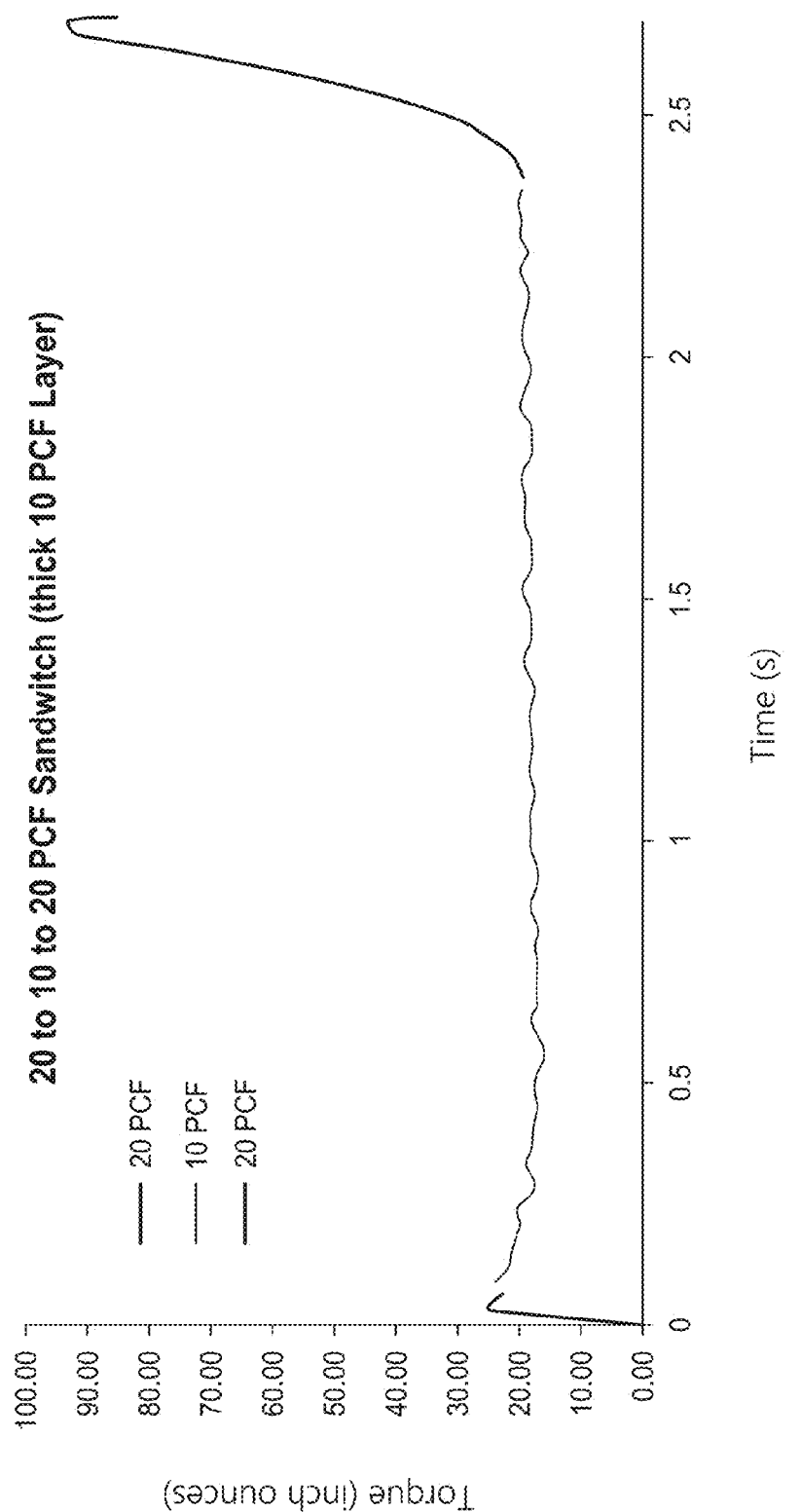

FIGS. 32-33 illustrate examples of a substrate comprising a 20 PCF layer, a 10 PCF layer, and another 20 PCF layer. In FIG. 32, the 10 PCF layer is thinner than the 20 PCF layers. In FIG. 33, the 10 PCF layer is thicker than the 20 PCF layers. As shown, there can be an initial higher torque area, followed by a lower torque area, then another higher torque area. Thus, the higher torque areas can sandwich the lower torque areas, similar to the cortical-cancellous-cortical procedure discussed above with respect to cortical breach. Again, embodiments of the screwdriver 100 can detect the different torque values and/or changes and correlate such data to a particular tissue type and/or transition between tissue types. Some embodiments provide the torque values and/or changes, or the tissue type and/or transition between tissue types, to the user to allow the user to understand what portion of tissue the screw is in. In some embodiments, the screwdriver can be configured to shut off the motor after experiencing a second increased torque area (such as the second 20 PCF areas shown in FIGS. 32-33).

Figure 34:
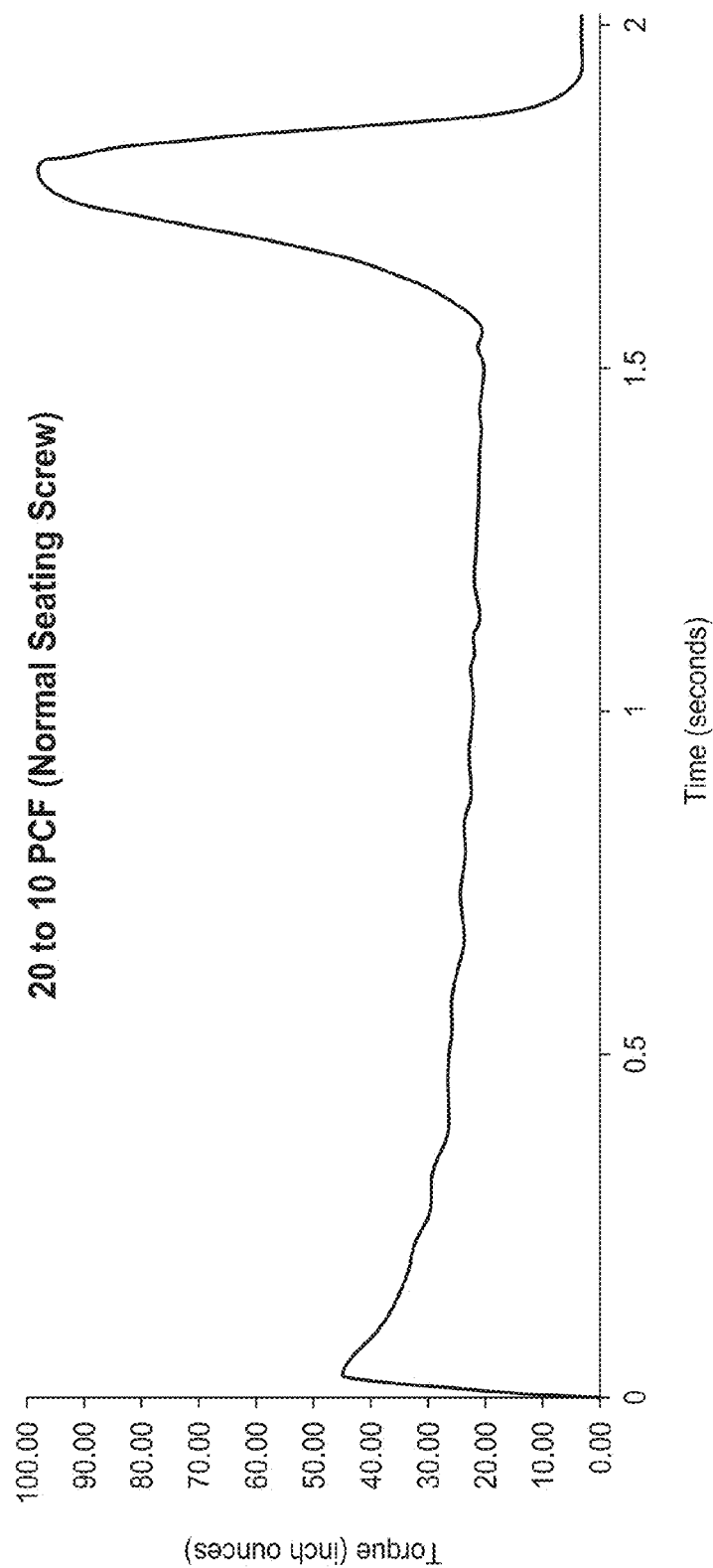

FIG. 34 illustrates an example torque curve of a well-placed pedicle screw. As shown, the pedicle screw can experience two high torque areas: the initial cortical bone (shown at the leftmost spike approaching around 45 in-oz) and the seating in the second cortical bone (shown in the rightmost spike reaching about 100 in-oz). In some embodiments, the motor 12 can be de-energized as the torque is increasing along the second spike, which can occur as the screw is cutting into the second cortical bone. For example, the motor 12 can be de-energized before the torque values are decreasing, which may indicates that the screw has pierced the bone.

In some embodiments, the torque differentiation is not used for seating a screw, but can instead be used prior to seating occurring. For example, in some embodiments, the torque curve can be used prior to a terminal portion of the torque curve, which is a high torque area where the seating would occur during a procedure. This terminal portion would be the rightmost spike of FIG. 34, and thus torque analysis could occur prior to the rightmost peak. In some embodiments, the screwdriver 100 can provide an output or change function of the screwdriver 100 prior to the second peak, such as at the transition of the relatively flat middle section to the second peak.

In some embodiments, the motor 12 of the screwdriver 100 can be shutoff during the seating procedure to avoid stripping of the screw. However, in some embodiments, the torque differentiation is not used to avoid stripping as the torque differentiation occurs prior to the seating of the screw.

While the actual torque values and curve can be useful for determining changes in torque, and thus tissue structure, it can also or alternatively be advantageous to look at derivatives of the torque, such as the speed or acceleration of the torque. This may provide for more accurate estimates in some embodiments and/or aid in determining tissue types, changes in tissue types, and/or location of the screw within the tissue types.

Figure 35:
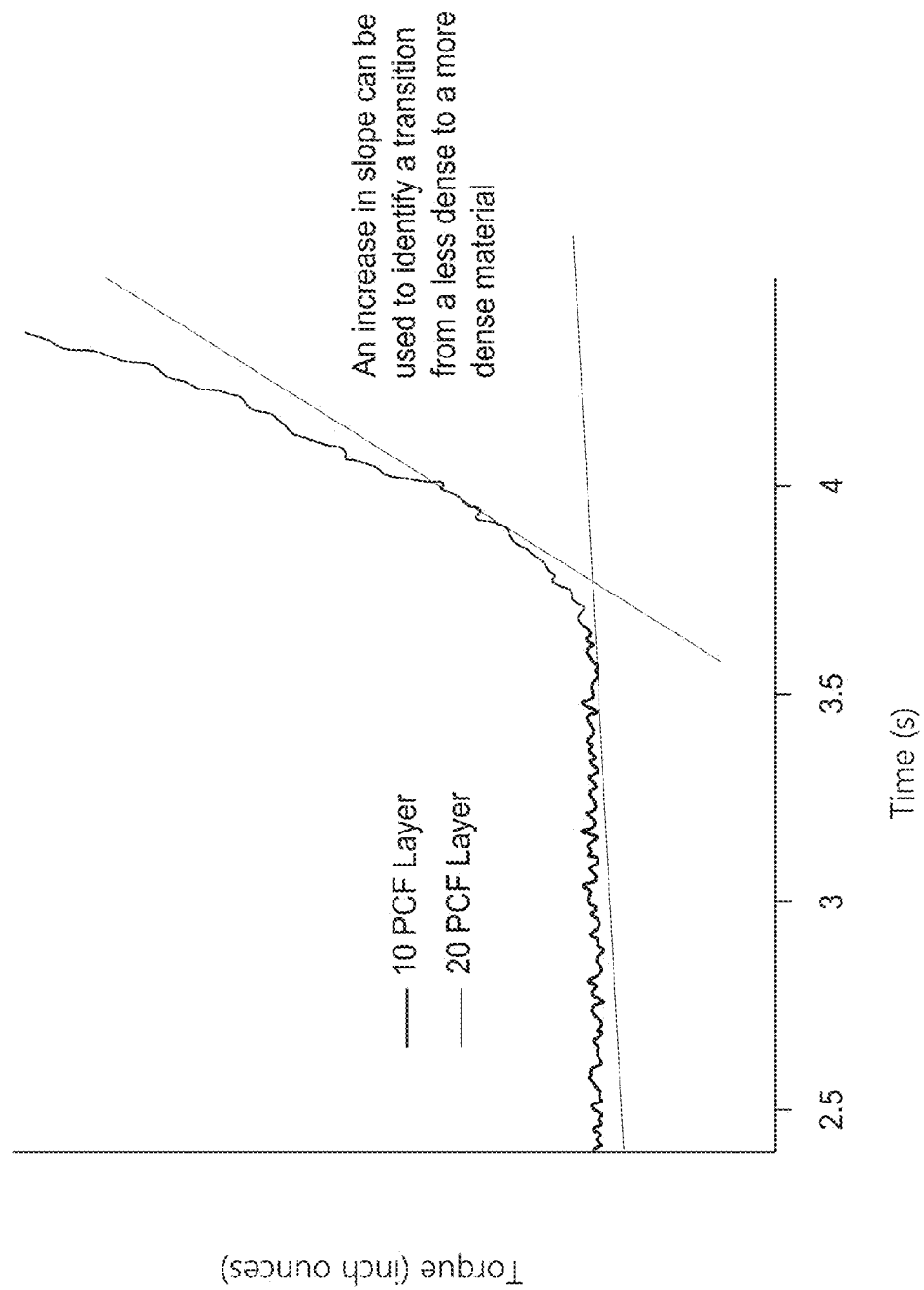
Figure 36:
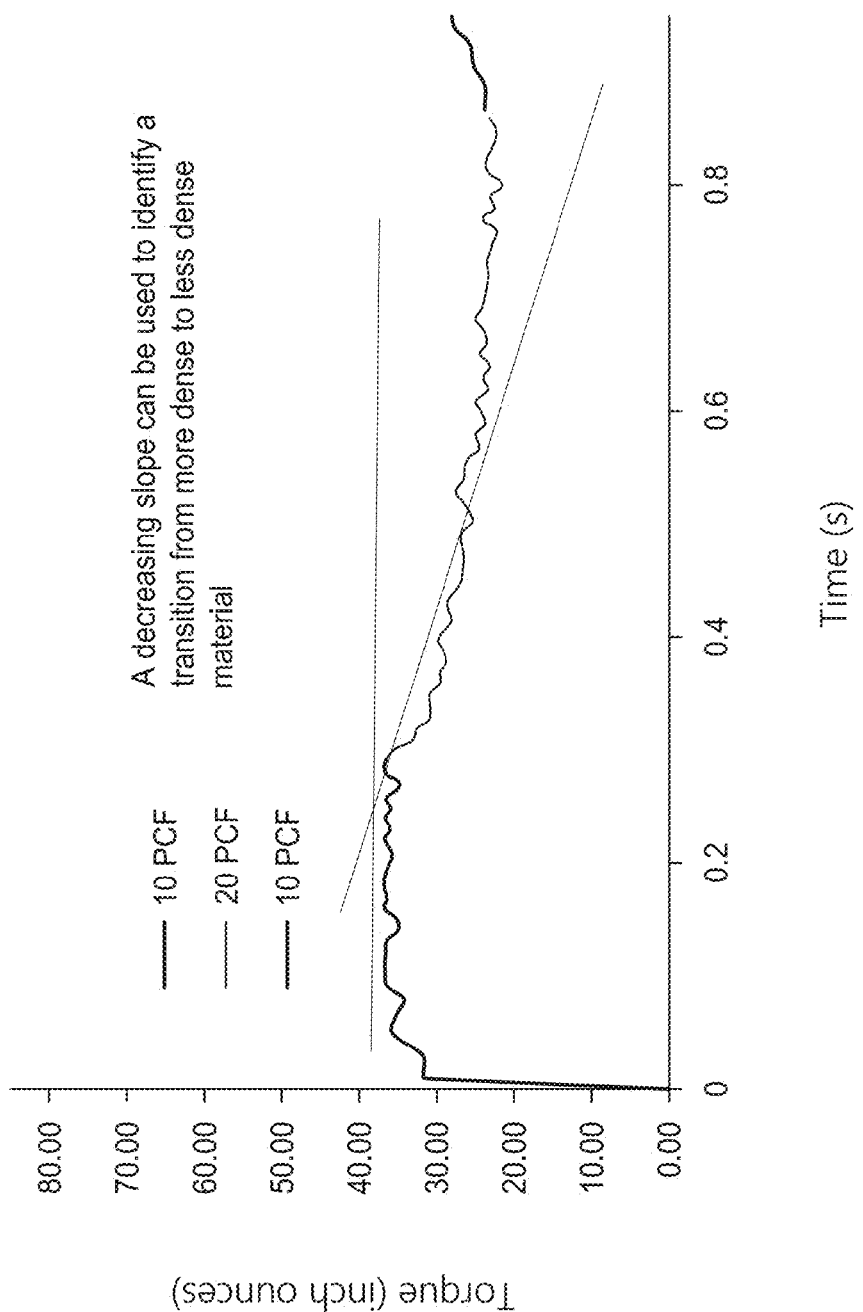

For example, in some embodiments, a first derivative can be used to determine penetrations from less dense to more dense tissue, such as shown in FIG. 35, which is the derivative of FIG. 31. Thus, when the screw moves from less dense to more dense tissue, the derivative value can increase and this information can be provided to a user. Similarly, a first derivative can be used to determine penetration from more dense to less dense tissue, such as shown in FIG. 36, which is a derivative of FIG. 31. Thus, apexes and valleys of the first derivative can be used to show changes in torque, which then can be related to the screwdriver and/or user.

Second derivatives can be used to determine various decreases and increases in the first derivative, which can be used to quantify changes in relative densities. With similar tissue densities, it would be expected to have a smaller change (e.g., faster change) in the first derivative, compared to a transition from a significantly less dense to a significantly more dense tissue which would be expected to have a much larger change (e.g., slower change) in the first derivative. So as a specific example, with the transition from cortical to the very low density tissues in the foramen there would be an expected rapid decrease in the first derivative that could be captured by the second derivative and the second derivative could be used to characterize that a very dense to non-dense transition occurred. On the other hand, the second derivative could be used to identify less pronounced tissue transitions, such as slightly more dense muscular tissues to slightly less dense fat tissue.

Figure 37:
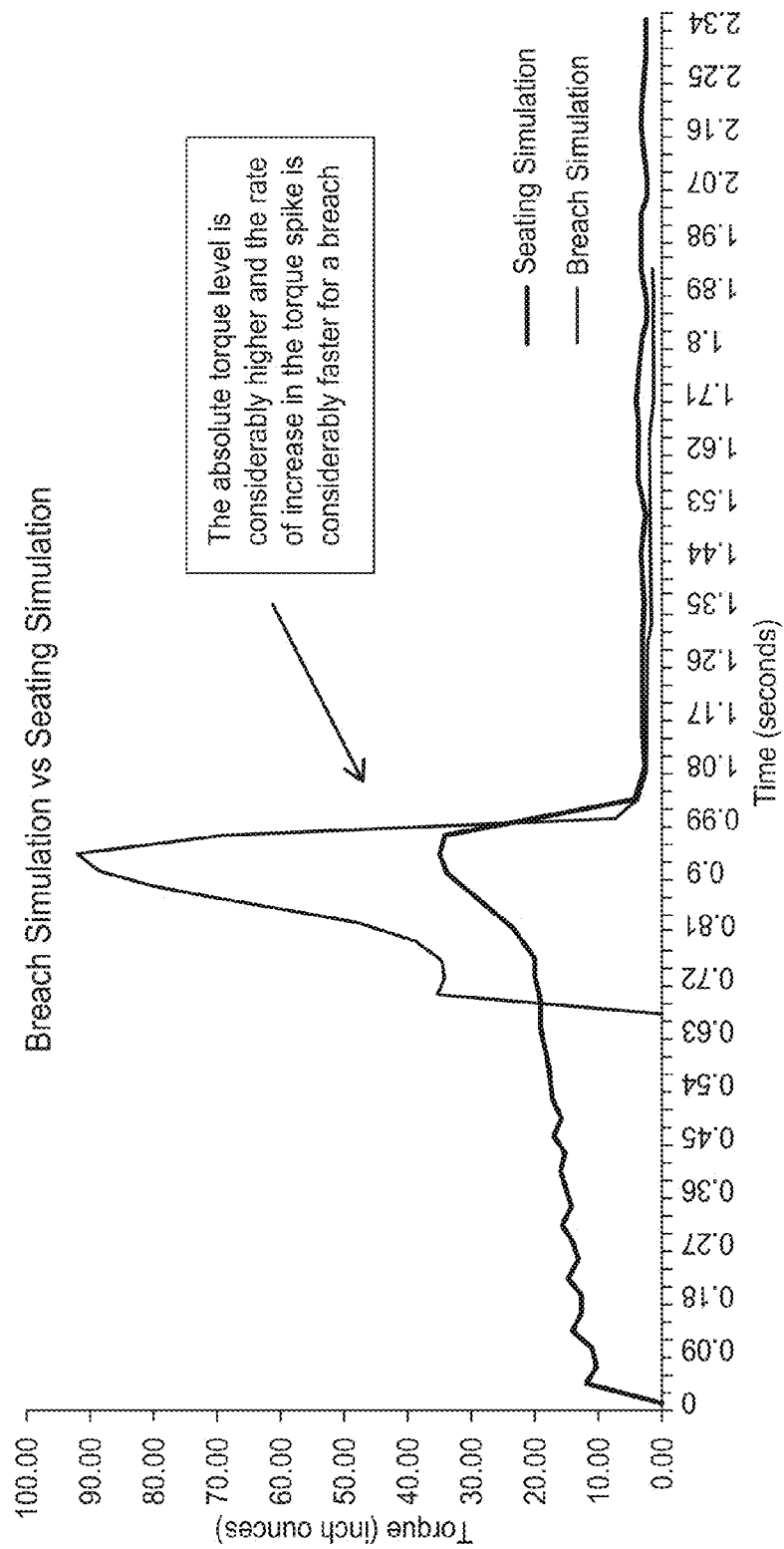

In some embodiments, the second derivative can be used in differentiating between screw seating and impact (e.g., an increase in torque from hitting higher density bones). FIG. 37 illustrates torque measurements showing a breach and showing a screw seating, specifically shown by the two peaks in the figure. In both peaks, the initial screw penetration peak and the screw seating peak for the first derivative is decreasing. As shown, the impact peak is "sharper" than the screw seating peak, which is generally rounder. Accordingly, the sharper peak (e.g., the impact peak) will have a first derivative that is changing (e.g., decreasing) more rapidly than the rounder peak. In some variants, the second derivative can be used to capture the relative rates of change of the first derivative, and/or to characterize the "curvature" of the torque curve. This can enable differentiation of the two peaks, identification of the type of peak (e.g., an impact peak vs. a seating peak, etc.). An example of this feature is shown in FIG. 37. As shown in the figure, the absolute torque from a screw impacting higher density cortical bone seems to be considerably higher than from the screw seating. Further, the rate of increase in torque from an impact appears to be considerably faster than from the screw seating. Thus, the rate of change of the first derivative appears to be faster with an impact than with seating.

Figure 38:
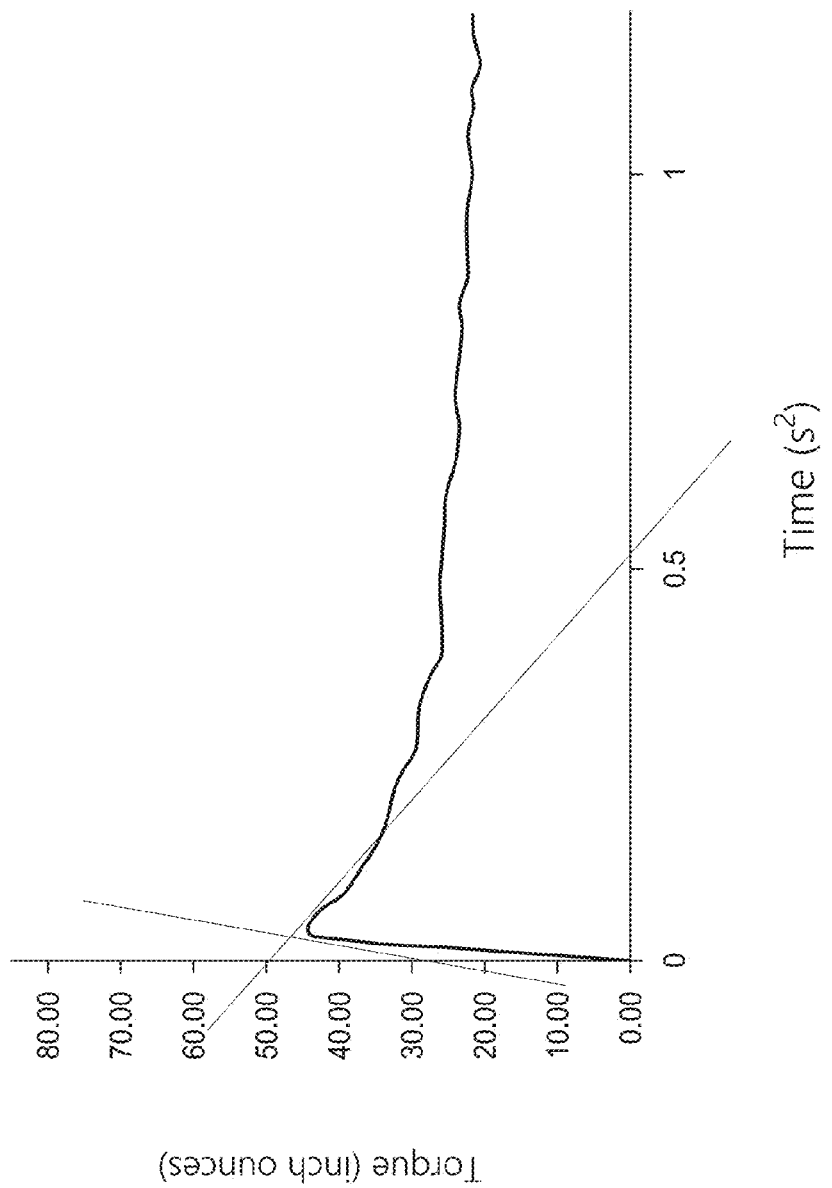

In some embodiments, the second derivative can be used to aid in distinguishing between various screw behaviors, such as between seating and initial screw penetration. In screw seating we expect an increasing first derivative and likewise after the first few threads of screw penetration we expect a decreasing first derivative. The second derivative can be used to distinguish between these two screw behaviors. An example second derivative is shown in FIG. 38.

Figure 39:
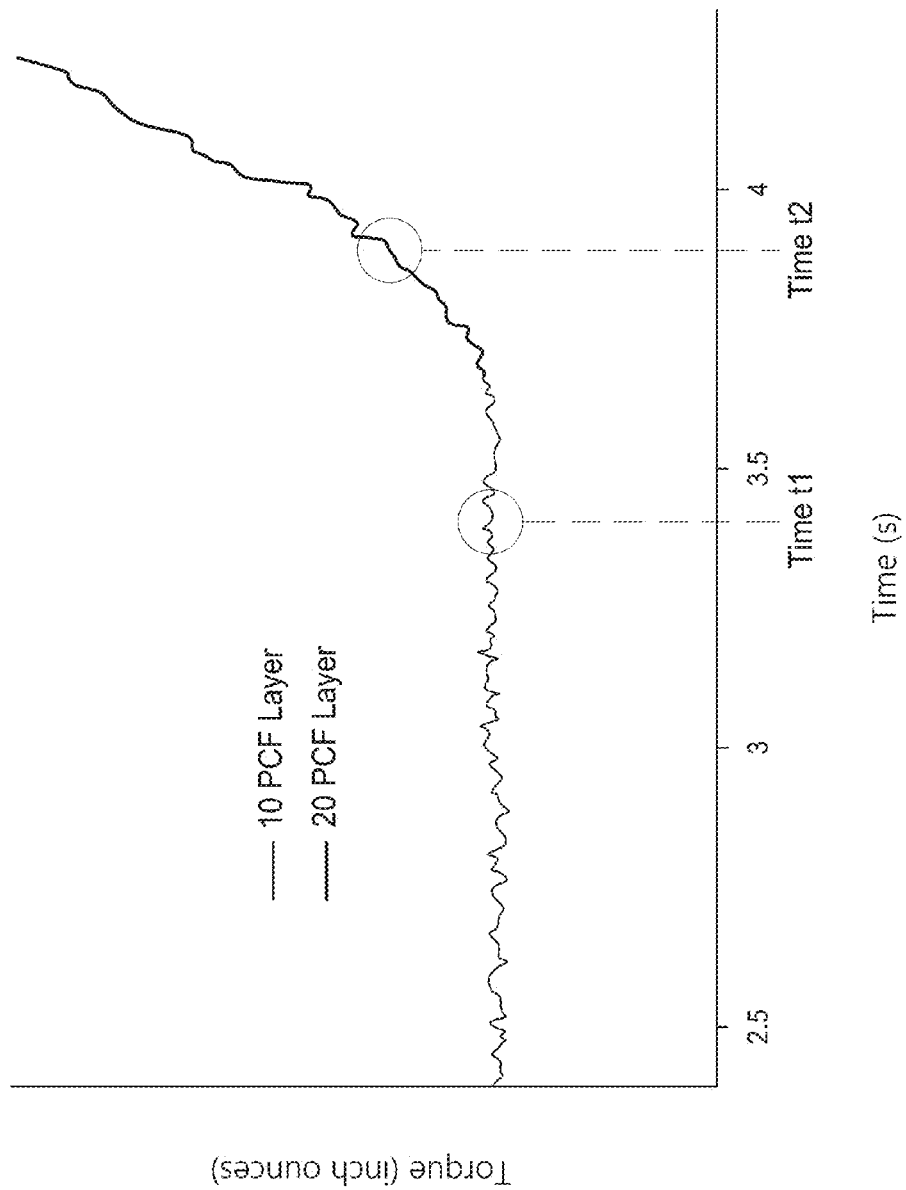

In some embodiments, an algorithm, such as a mathematical formula, can be used to identify torque changes as discussed above. For example, in the embodiment illustrated in FIG. 39, if torque t2 greater than t1, then the screw is determined to have penetrated a new material that is likely more dense. If torque at t2 less than or equal to t1, then the screw is determined to remains in the same material or have penetrated a new material that is equally or likely less dense. In some embodiments, the same equations can be used but with additional explicit values included, such as t2>t1+X, whereas X can be preprogrammed into the screwdriver 100 or can be added by the user. Thus, embodiments of the screwdriver 100 can use two time based torque measurements to determine if there is a transition between tissues. These measurements can be taken every few seconds, every second, or even smaller time periods such as milliseconds, and the particular time periods are not limiting and can be passed along to the user.

Figure 40:
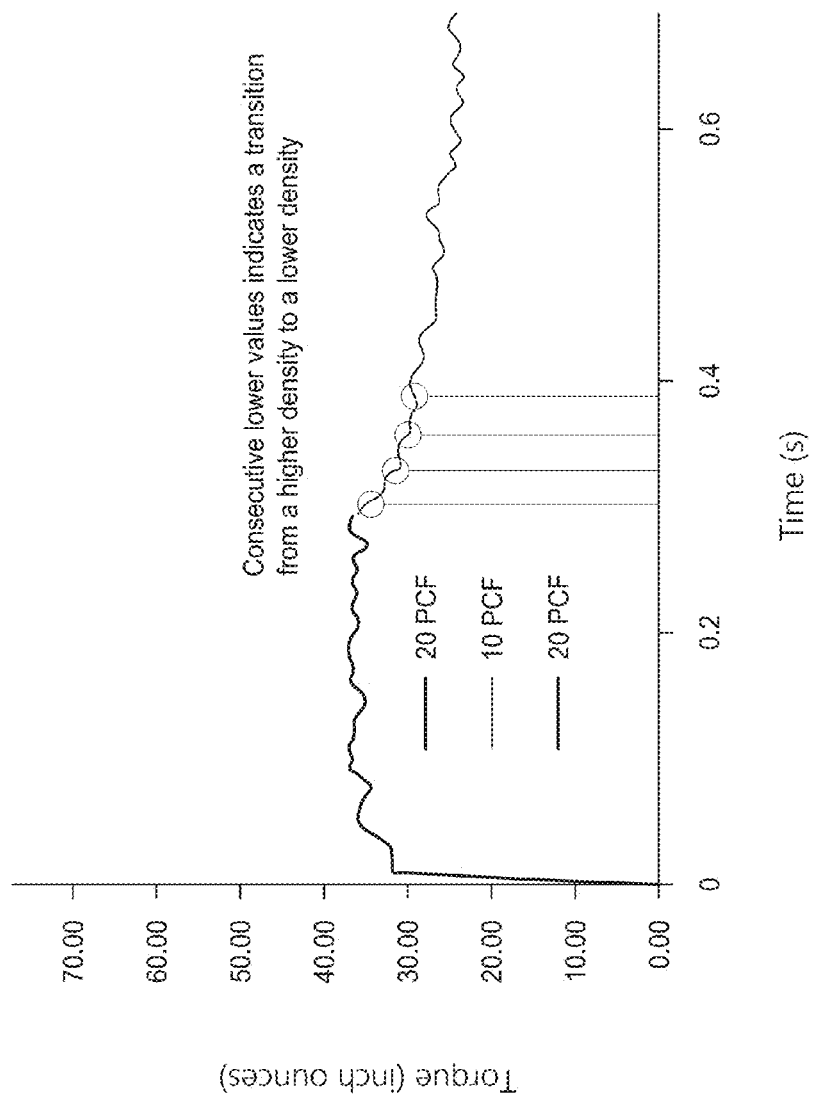
Figure 41:
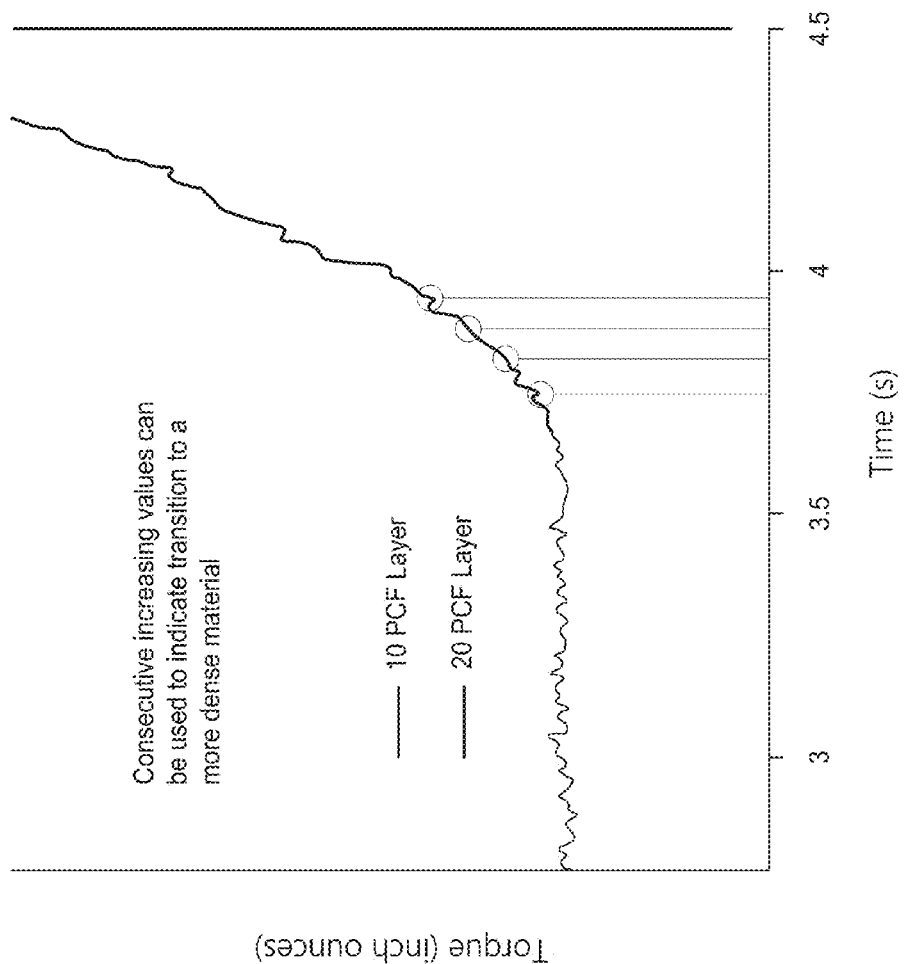

In some embodiments, consecutive lower/higher values can be used to correlate upward and/or downward transitions to more or less dense tissues, such as shown in FIGS. 40-41. Thus, in some embodiments, the screwdriver 100 can use a plurality of different torque measurements to determine tissue transitions. For example, the screwdriver can analyze 2, 3, 4, 5, 6, 7, 8, 9, or 10 different measurements. In the example shown in Figure L, the screwdriver 100 can use a plurality (e.g., 4) of consecutive decreasing torque values to identify a transition from a higher density material to a lower density material. In the example shown in Figure M, the screwdriver 100 can use a plurality (e.g., 4) of consecutive increasing torque values to identify a transition from a lower density material to a higher density material. The use of consecutive increasing or decreasing torque values can reduce the likelihood of a noise or error being detected as a tissue transition.

While all of the mathematical methods described herein can be used as standalone methods to characterize screw behavior and the penetration materials, the various operational methods can also be used as backup options. For example, the methods can be used to verify a primary torque control algorithm.

Figure 42:
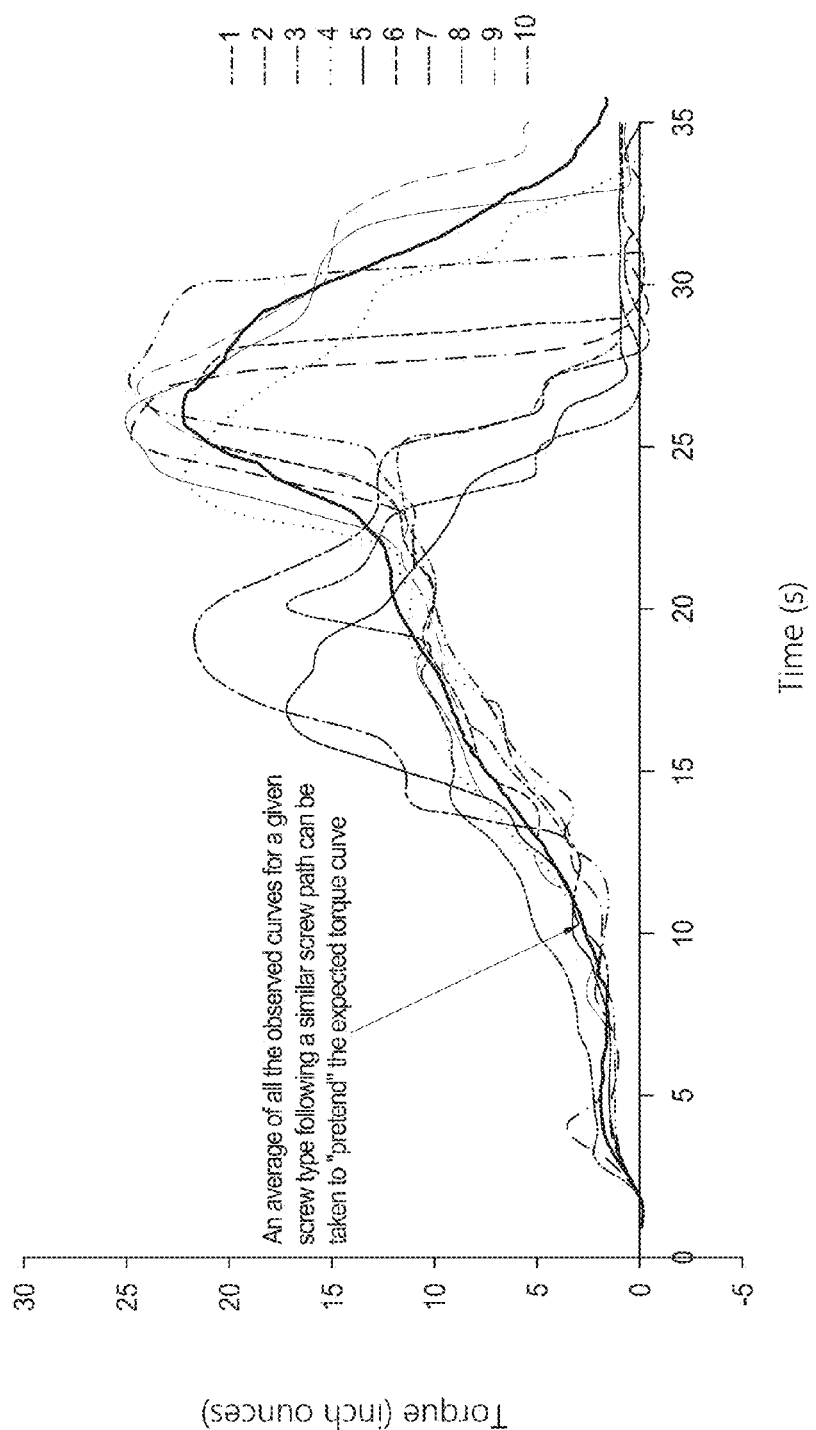

For example, "pre-mapping" torque curves to the memory of the device for reference during real time operation could be quite useful, as shown in FIG. 42. If, for example, measurements were taken of a statistically significant sample size of screws driving into a composite of materials, mean representation of those curves could be extracted and used as a reference for what the expected torque path will be. These "pre-mapped" curves could be installed into the screwdriver 100 and modifications can be made to the screwdriver 100, such as motor speed or activation of a signal, based on such curves. For example, when the torque curve is off a particular percentage from the pre-mapped torque curve, such as outside of about: 1%, 5%, 10%, or 20%. In some embodiments, this may only occur at transition sections. This information can be loaded onto the screwdriver 100 prior to any surgical procedure. An average, shown in the darker line of FIG. 42 may be constructed from the pre-mapped curves.

A priori analysis can be conducted to determine where along this mean path a material transition zone is happening, for example, and when during the actual operation of the device the data input (e.g., measured torque) curve shows similarities to that section of the torque curve drive velocity adjustments can be made accordingly.

Figure 43:
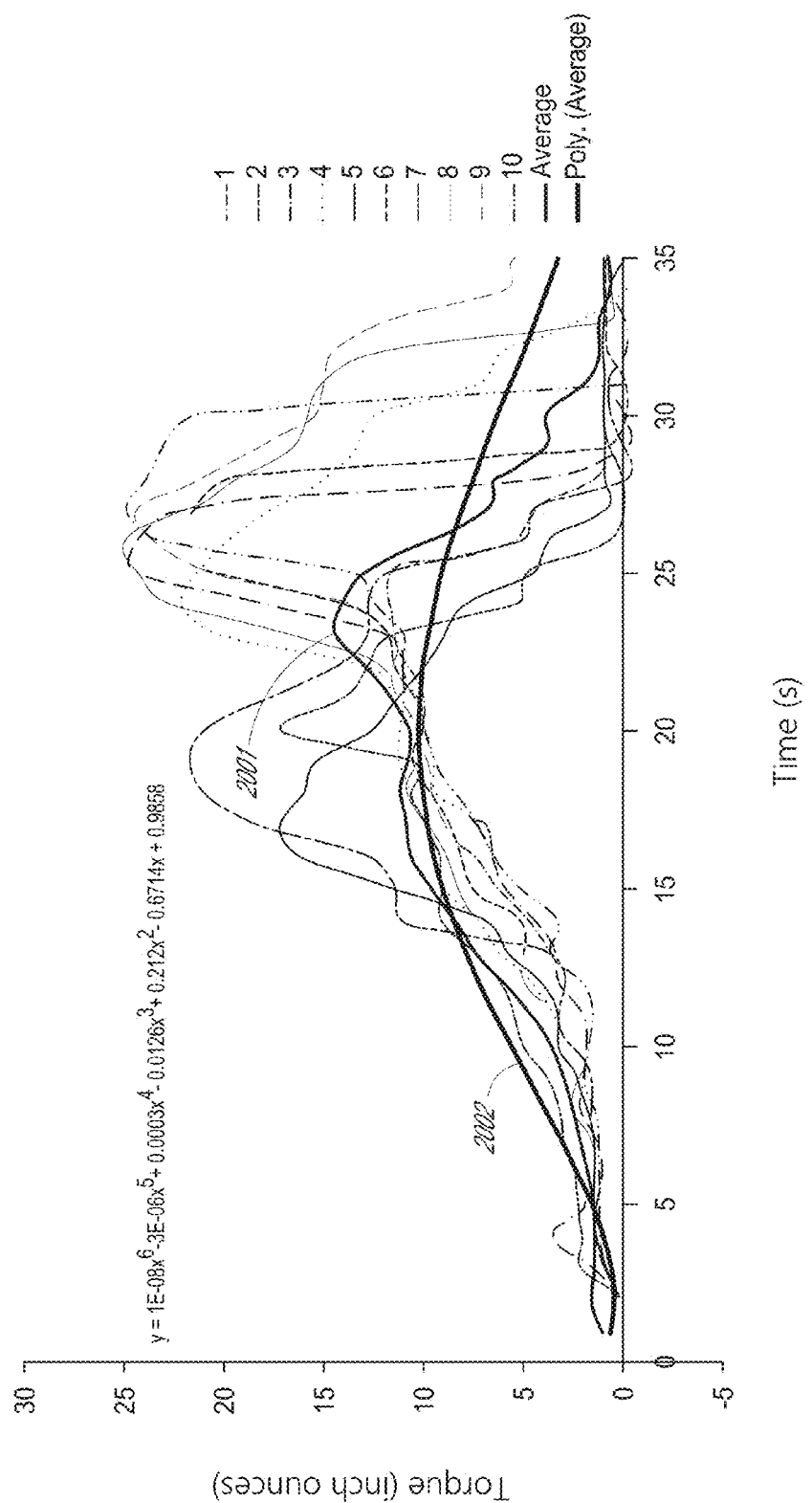

Some embodiments use mathematical function and derivatives for a priori and post facto analysis as shown in FIG. 43. With analysis of bones with variable density, for example, where similarly shaped torque curves with a vertical shift in the torque axis (a y-axis only shift) would be expected, characterizing torque curves with mathematical functions and taking derivatives and second derivatives could be very useful. Further, an average torque 2001 can be determined from the different torque curves.

For example, in FIG. 43, the aggregation of curves can be characterized with a polynomial equation 2002 and solved for the first and second derivatives at different points of time. Thus, if torque was outside a particular percentage of the polynomial equation, the user could be informed or the screwdriver could modify functionality, such as de-energizing the motor. This could be especially useful for real time depth measurements. For example, in some embodiments, the torque curves can be torque vs. time. Depth of the screw can be determined given that it will be understood what the torque curve looks like during the first few threads catching (and thus how to identify the starting depth) and given the screw's pitch and rotational speed (which can be measured from, for example, voltage). Thus, in some embodiments, the screw behavior can be characterized not only as a function of time but as a function of screw depth, which could potentially enhance the accuracy of mappings.

As an example, robotic assisted surgeries currently take MRI's and use them to preprogram robots with parameters that can restrict the motion of the tool attached to the robot. For example, if the user tries to push the tool beyond pre-programmed parameters the robot overrides the input (for example, it can stop movement along an axis, such as a depth axis for a saw after a certain depth has been penetrated, thereby preventing overcutting). Likewise, various dimensions of a patient specific disk (such as the distance from the outer cortical bone to the foramen) could be programmed into embodiments of the screwdriver. In some embodiments, a healthy torque curve could be mapped and the misplaced torque curve would look like per unit of distance for a specific patient, and then program the device with that patient specific information. Thus, exactly what would be expected to be seen from the torque curve for that specific patient at certain depths (which is much more difficult to do as a function of time) can be characterized. If the torque curve varied from the healthy torque curve, the motor 12 of the screwdriver 100 may shut off, preventing any incidental damage.

Thus, in some embodiments, pre-mapping a patient procedure can be used to program the screwdriver 100 prior to use. For example, approximating screw penetration depth and pre-mapping the patient specific procedure with what mathematically would be expected in a healthy and unhealthy torque curve could allow further control of the screwdriver.

As mentioned above, while driving the screw, the screwdriver 100 can be taking discrete measurements of torque over fixed time intervals. A table of slopes with smoothing function like a moving average can be used to make determinations about changes in materials and to identify general changes in torque.

Table B (below) demonstrates the torque changes for certain tissue transitions from less dense to more dense material.

TABLE B

| Seconds | Torque (in oz) | Slope | Slope (10 period avg) |
|---|---|---|---|
| 2.5 | 19.93 | | |
| 2.51 | 20.16 | 22.96 | |
| 2.52 | 18.91 | −124.65 | |
| 2.53 | 19.36 | 44.73 | |
| 2.54 | 19.30 | −6.26 | |
| 2.55 | 19.27 | −2.68 | |
| 2.56 | 19.75 | 47.71 | |
| 2.57 | 19.95 | 20.28 | |
| 2.58 | 20.44 | 48.90 | |
| 2.59 | 20.09 | −35.19 | |
| 2.6 | 20.15 | 6.86 | 2.27 |
| 2.61 | 19.55 | −60.24 | −6.05 |
| 2.62 | 18.75 | −79.92 | −1.58 |
| 2.63 | 19.58 | 82.60 | 2.21 |
| 2.64 | 19.59 | 1.19 | 2.95 |
| 2.65 | 19.32 | −26.84 | 0.54 |
| 2.66 | 19.96 | 63.52 | 2.12 |
| 2.67 | 19.82 | −13.72 | −1.28 |
| 2.68 | 19.27 | −55.47 | −11.72 |
| 2.69 | 19.64 | 37.87 | −4.41 |
| 2.7 | 19.29 | −35.78 | −8.63 |
| 2.71 | 19.18 | −10.44 | −3.70 |
| 2.72 | 19.49 | 31.01 | 7.40 |
| 2.73 | 19.62 | 12.52 | 0.39 |
| 2.74 | 20.02 | 39.96 | 4.26 |

Figure 44:
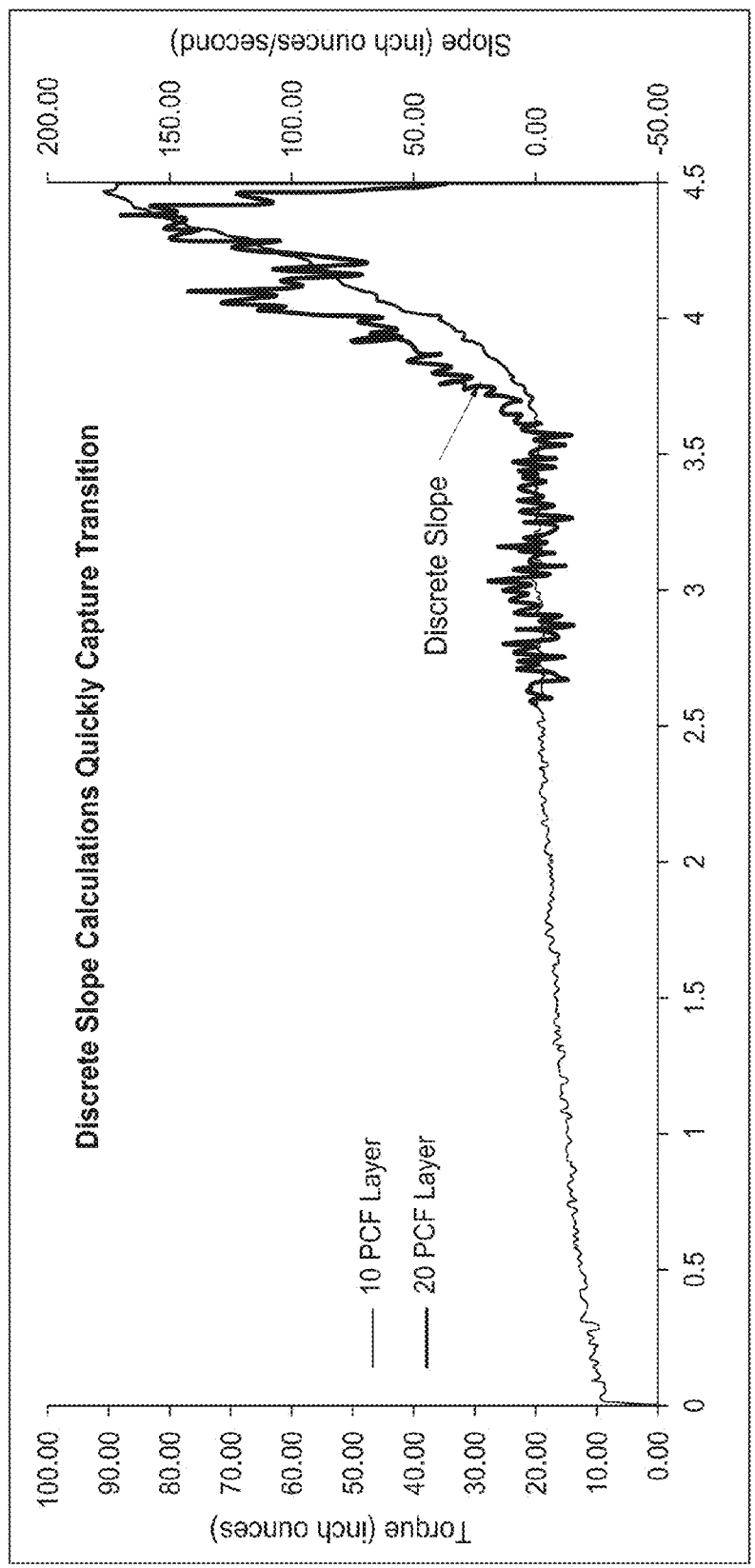

The table values above are plotted in FIG. 44 and demonstrate that the slope, even with a 10 period moving average is very quick at identifying where and when a transition zone has been identified.

Table C (below) demonstrates the torque changes for certain tissue transitions from more dense to less dense material.

TABLE C

| Seconds | Torque (in oz) | Slope | Slope (15 period avg) |
|---|---|---|---|
| 0.05 | 35.99 | | |
| 0.06 | 35.74 | −25.35 | |
| 0.07 | 35.22 | −51.29 | |
| 0.08 | 34.42 | −79.92 | |
| 0.09 | 36.64 | 222.16 | |
| 0.1 | 36.70 | 5.37 | |
| 0.11 | 36.96 | 25.94 | |
| 0.12 | 36.40 | −55.47 | |
| 0.13 | 36.56 | 15.21 | |
| 0.14 | 35.38 | −117.49 | |
| 0.15 | 35.22 | −15.80 | |
| 0.16 | 36.75 | 152.68 | |

TABLE C-continued

| Seconds | Torque (in oz) | Slope | Slope (15 period avg) |
|---|---|---|---|
| 0.17 | 36.43 | −32.21 | |
| 0.18 | 36.92 | 49.20 | |
| 0.19 | 36.93 | 0.89 | |
| 0.2 | 36.31 | −62.03 | 2.13 |
| 0.21 | 35.88 | −42.34 | 0.99 |
| 0.22 | 36.77 | 88.86 | 10.34 |
| 0.23 | 36.13 | −63.81 | 11.41 |
| 0.24 | 36.71 | 57.55 | 0.44 |
| 0.25 | 36.15 | −56.05 | −3.66 |
| 0.26 | 36.55 | 39.66 | −2.74 |
| 0.27 | 34.79 | −175.34 | −10.74 |
| 0.28 | 36.82 | 203.07 | 1.79 |

Figure 45:
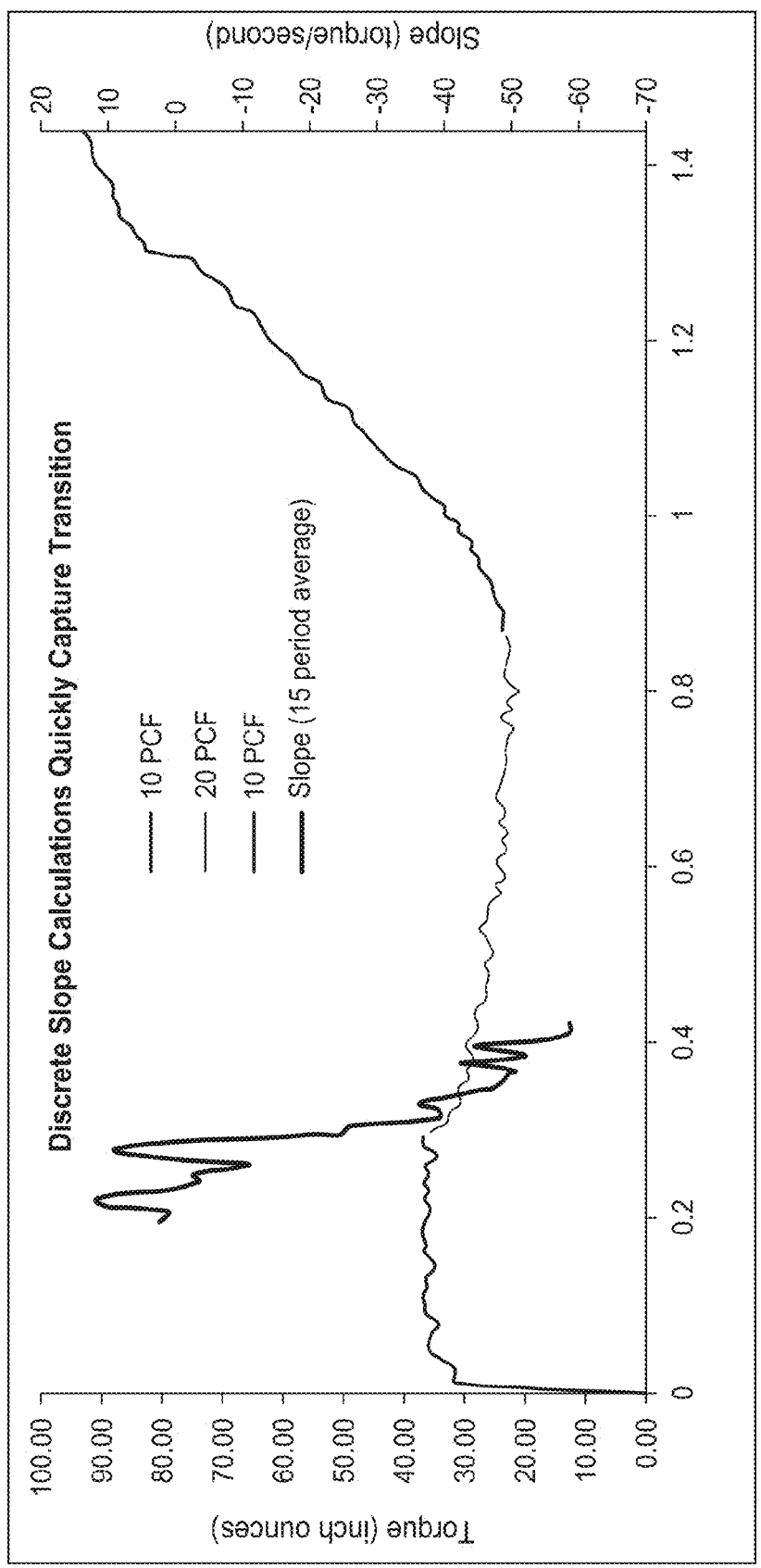

The table values above are plotted in FIG. 45 and demonstrate that the slope, even with a 15 period moving average, can be very quick at identifying where and when a transition zone has been identified. In some embodiments, rates of change in slopes or a second derivative with smoothing functions (e.g., a moving average) can be used to make determinations about changes in materials and to identify general changes in torque.

Table D (below) demonstrates that the distinct differences in behavior from the torque changes for certain tissue transitions and the torque changes of a screw initially driving for example can be captured by looking at rates of change of slope, or the second derivative.

TABLE D

| Seconds | Tissue Transition Slope | Screw Driving Slope |
|---|---|---|
| 0 | 5.49 | 98.16 |
| 0.01 | 3.43 | 7.81 |
| 0.02 | 6.38 | 13.24 |
| 0.03 | −3.31 | 5.81 |
| 0.04 | −2.24 | 15.12 |
| 0.05 | 4.35 | 13.47 |
| 0.06 | 1.25 | 10.97 |
| 0.07 | 2.59 | 22.45 |
| 0.08 | 6.14 | 22.39 |
| 0.09 | −7.19 | −3.61 |
| 0.1 | 5.84 | 7.48 |
| 0.11 | 8.35 | 8.71 |
| 0.12 | −6.80 | −1.73 |
| 0.13 | −1.34 | 11.09 |
| 0.14 | 1.67 | 1.07 |
| 0.15 | −1.46 | 1.49 |
| 0.16 | −2.89 | 14.79 |
| 0.17 | −11.18 | 0.92 |
| 0.18 | −6.26 | −12.64 |
| 0.19 | −0.12 | −4.06 |

Figure 46:
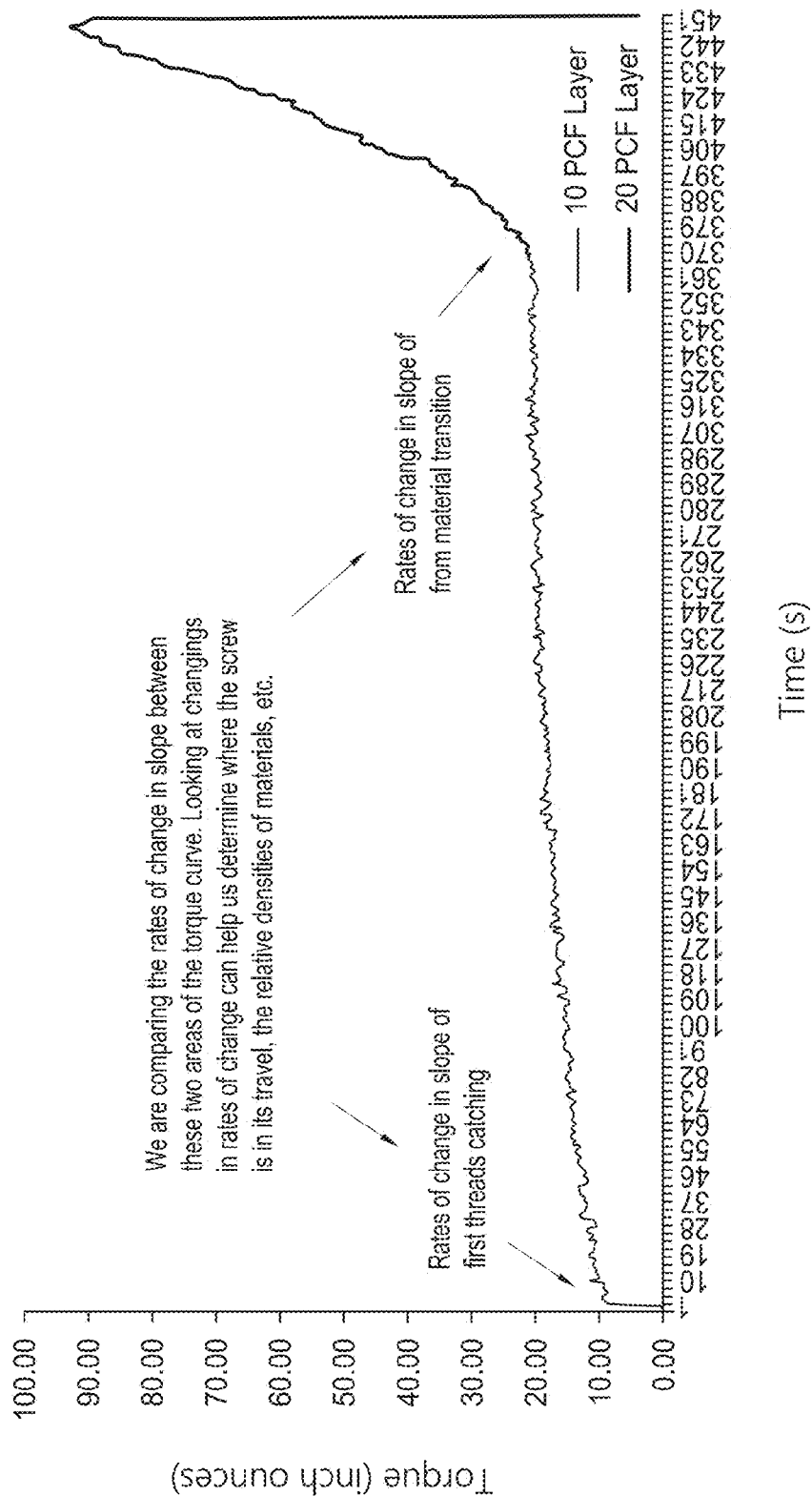

The above table values were calculated from 10 period moving averages of slope calculations from the torque curve of FIG. 46.

Figure 47:
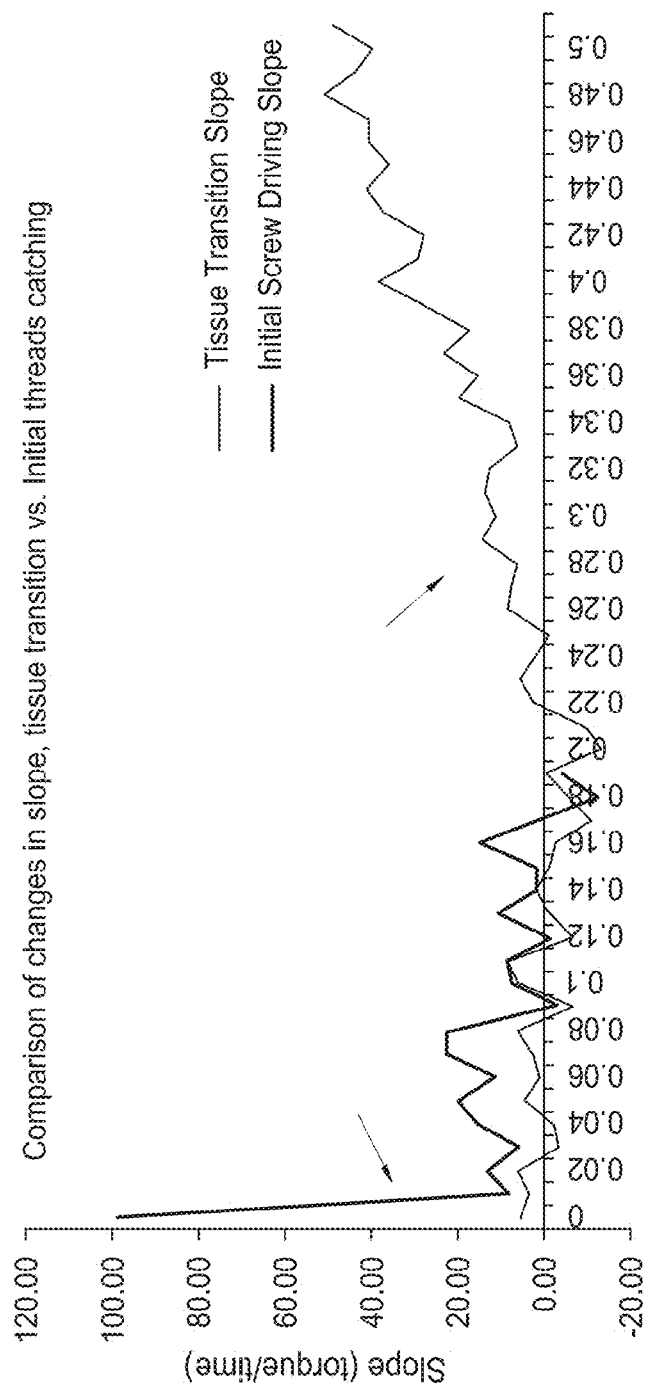

The table values above are plotted in FIG. 47 and demonstrate that rates of change in the slope can be used to identify where the screw is in its path of travel, the type of material it is in, amongst other characteristics.

Figure 48:
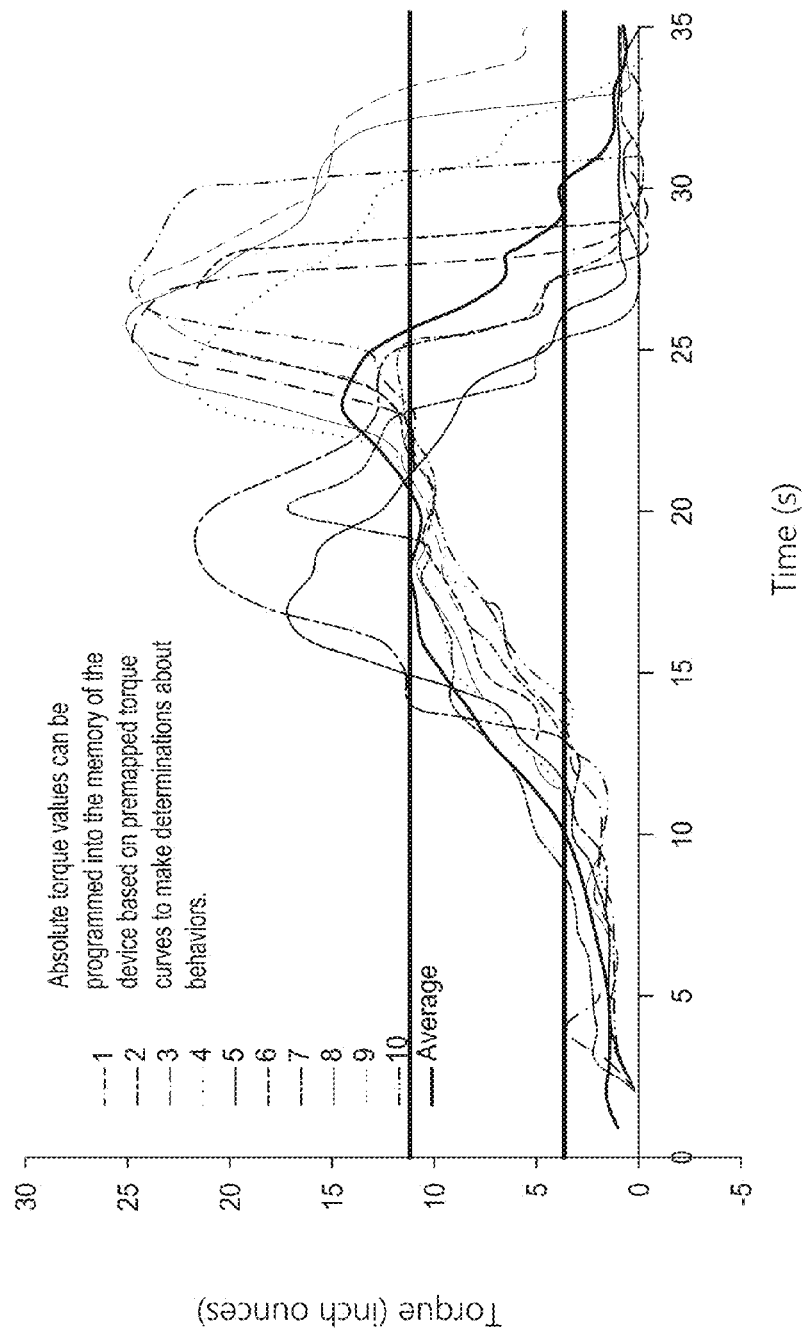

Absolute torque values can be programmed into the memory of the screwdriver based on pre-mapped torque curves to make determinations about behaviors, for example, to identify a tissue transition zone or to identify screw seating. This feature is shown in FIG. 48, with the generally horizontal lines being the absolute torque limits. While not all bone between patients is the same density, most of the variability is in the density of the cancellous bone (for example osteoporosis) not the cortical bone. Therefore, with a specific screw, specific torque values can be associated with certain stages of the screw insertion process. For example, it can take X amount of torque to start driving a screw, it can take Y amount of torque to transition from cancellous bone to cortical bone, etc. Certain embodiments of the screwdriver 100 are configured to change behavior in response to the detection of such torque values. For example, if the screwdriver 100 determines that the torque applied to the screw approaches and/or crosses an absolute torque value (which can be programmed into the screwdriver 100), the screwdriver 100 can take action, such as to stop driving the screw and/or issue an alarm.

Figure 49:
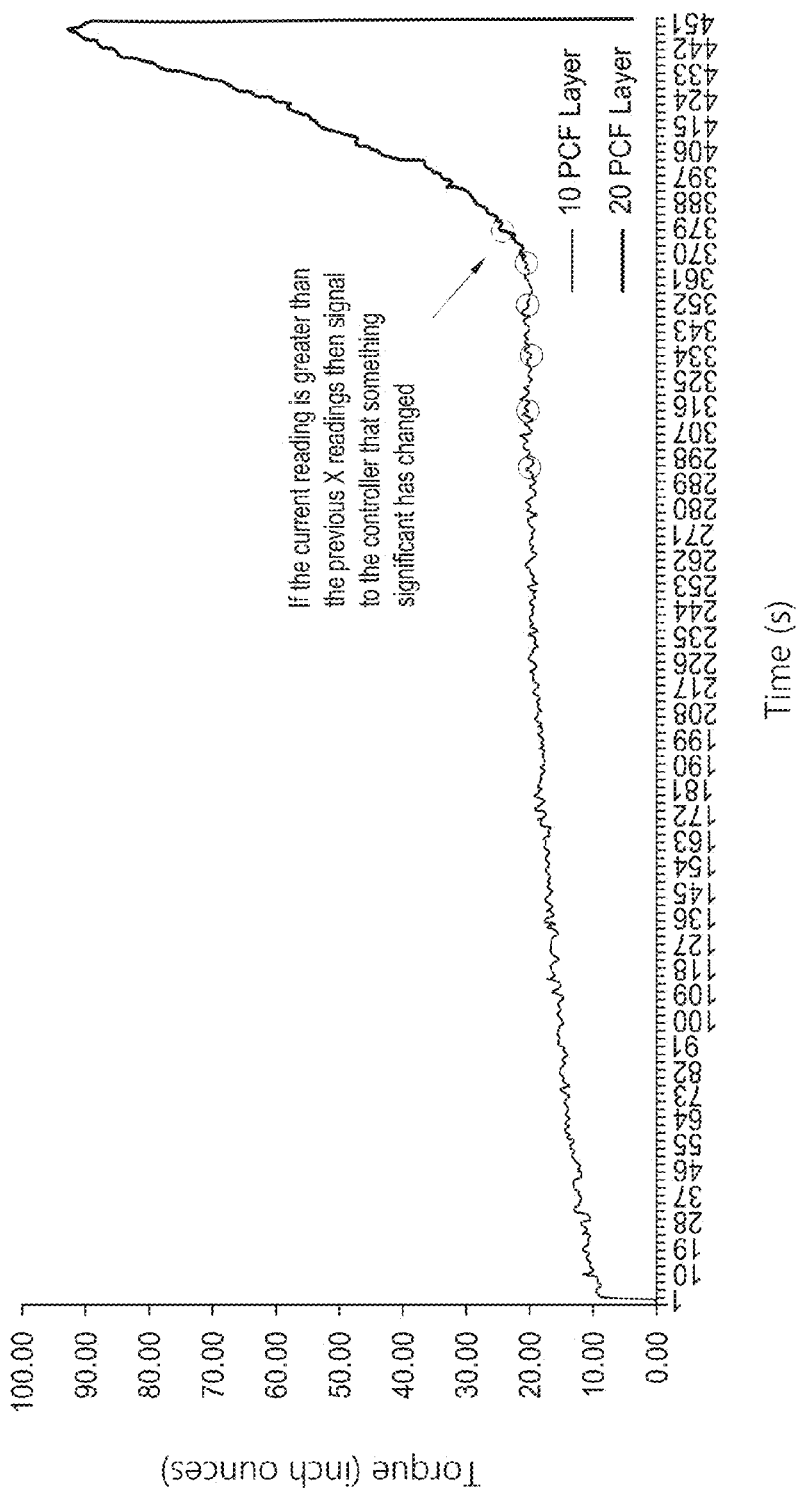

In some embodiments, the screwdriver is configured to identify material changes in torque. For example, as shown in FIG. 49, in some embodiments, if torque at time t2 is greater than the torque of X previous observed values (or a smoothing of previous values like a moving average), then the screw is determined to have penetrated a new material type that is likely more dense. This information can be relayed to the user (e.g., surgeon), such as through an audible or visual indicator. On the other hand, if torque at t2<torque of X previous observed values (or a smoothing of previous values like a moving average) then the screw remains in the same material or has penetrated new material that is likely less dense. In this situation, in some embodiments, no further information would be provided to the user.

Figure 50:
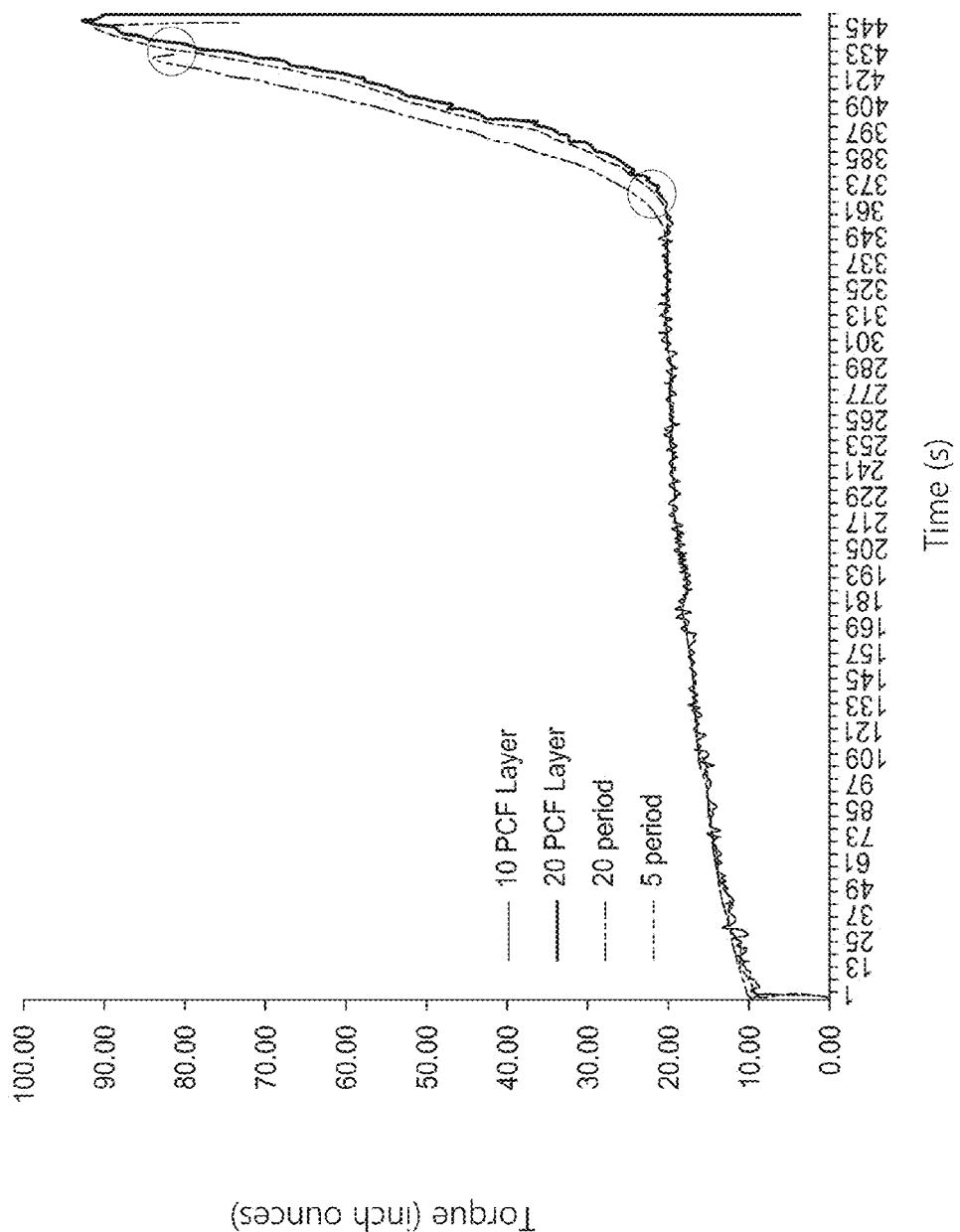

A significant challenge of using torque analysis to manage drive velocity is properly sensitizing the readings, and/or extracting the signal from the noise. Various smoothing techniques can be used to help achieve this, and the particular smoothing procedure is not limiting. One method is to plot two moving averages of the torques, a faster and slower moving average, and looking at the relative values of each to make the determination about the material the screw is currently in. For example, as shown in FIG. 50, a 5 period moving average and a 20 period moving average can help make determinations about transition zones or changes in screw behavior (like seating or the initial threads catching). The moving averages can be calibrated and relative values can be calibrated depending on the desired sensitivity. The faster moving average can be more responsive to the initial torque spike than the slow moving average. Thus, when the fast moving average came close enough or crossed the slow moving average, it could be used to indicate that the first threads of the screw have caught and the screw is actively being driven.

Figure 51:
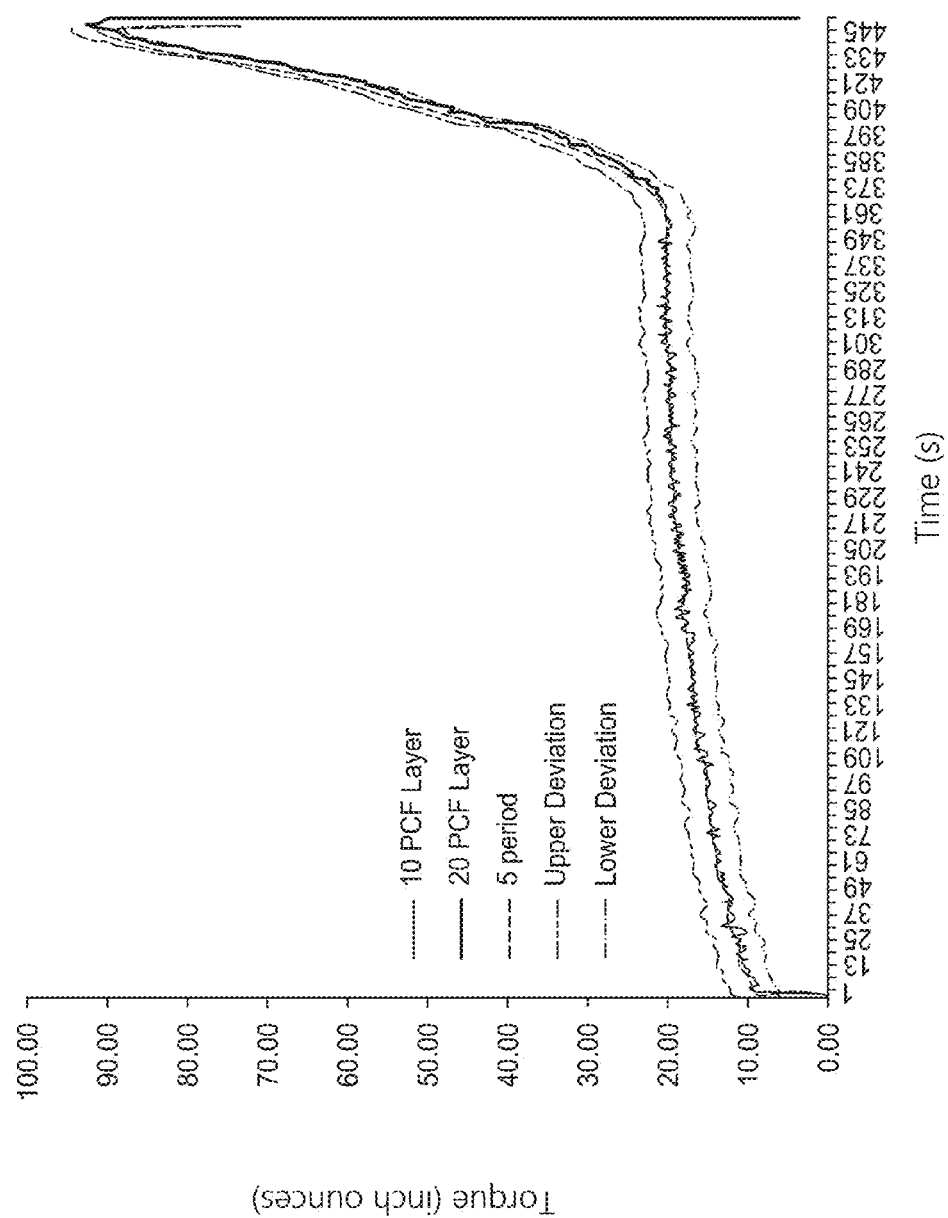

Another smoothing technique is to measure deviations from a moving average to determine points of transition, such as shown in FIG. 51. An example of this formula would be X period moving average+/−standard deviation of previous X observations. A material deviation beyond an upper or lower deviation could signal a change of material (which can be provided to the user) without being overly sensitive to smaller deviations.

In various embodiments, the screwdriver is programmed to identify when the torque curve is changing and to determine that such change indicates that something has changed in the screw path (e.g., the first few threads have successfully caught, tissue transition, screw seating, etc.). Using a fast and/or slow moving average can help identify changes to the torque curve. Certain implementations enable a user to change (e.g., calibrate) the sensitivity, such as by changing the moving average values.

More About Using Torque Differentials

Figure 53:
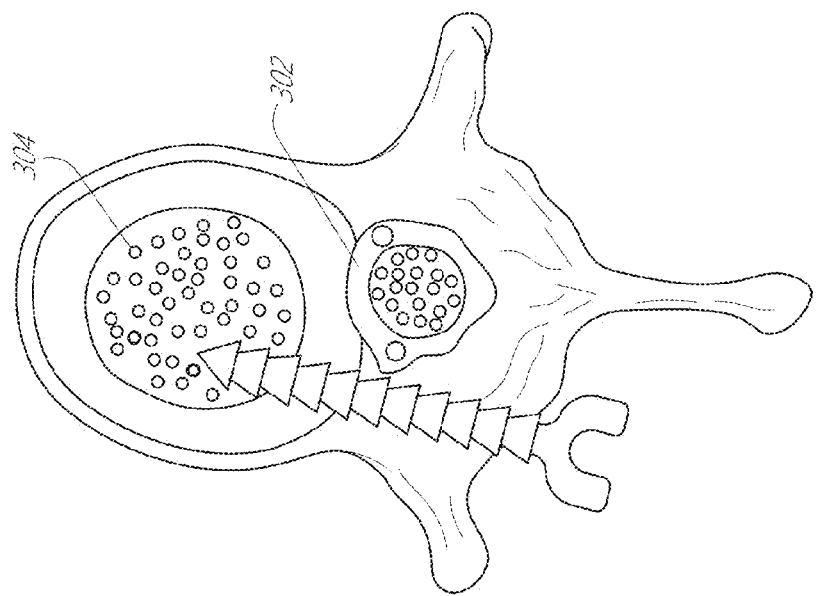
FIG. 53 illustrates a well-placed pedicle screw.
Figure 52:
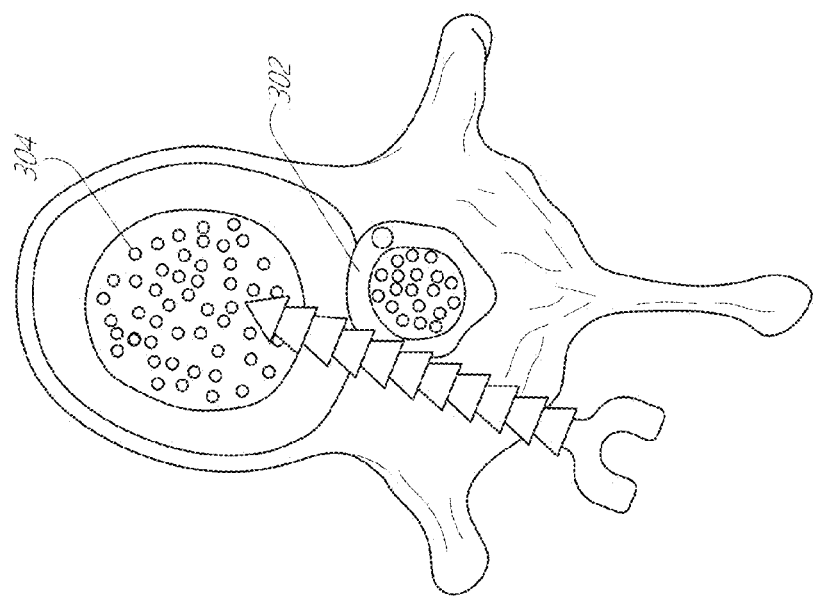
FIG. 52 illustrates a pedicle screw that has grazed cortical bone and/or the spinal column.

For a spinal fusion application, or other applications, some embodiments of the device can detect when a screw tip or screw body has impacted cortical bone (e.g., medially, laterally, or anteriorly). Certain embodiments are configured to detect when a screw tip or screw body has directly impacted cortical bone, such as when the tip of the screw is on a trajectory to penetrate into the spinal column. Some variants are configured to detect when a screw tip or screw body has grazed cortical bone 302, such is shown in FIG. 52. In some embodiments, the screwdriver 100 detects the impact from discrete current, voltage or torque measurements, or other data. In response to detection of the impact, the screwdriver 100 can signal the motor 12 to stop driving and/or can otherwise stop driving of the screw, thereby inhibiting or preventing a breach and/or significant damage to sensitive structures (e.g., nerves in the spinal cord). In some embodiments, the screwdriver 100 is configured to detect that the screw tip or screw body is on a proper insertion trajectory into cancellous bone 304, such as is shown in FIG. 53.

Cortical breaches of greater than 4 mm may be considered especially serious and may be associated with neurologic deficits. On the other hand, breaches of less than 4 mm range may be acceptable, such as for certain screws placed in vertebrate T10 through L4. Some breaches ranging from 2 mm medially and 4 mm laterally may be acceptable. In various embodiments, the powered device can be configured to stop driving of the screw within the acceptable breach depths. Certain breaches are graded (e.g., grade 0 for no breach, grade 1 for a breach distance of less than 2 mm, grade 2 for a breach distance of 2 mm to 4 mm, and grade 3 for breach distance less greater than 4 mm). Some embodiments of the screwdriver 100 are configured to stop driving of the screw at a grade of 2 or less.

In some embodiments, the screwdriver 100 can identify transition zones between materials with variable densities using discrete current, voltage, or torque values. In some embodiments, the device can be programmed to identify and characterize material types based on expected current, voltage or torque feedback preprogrammed to the controller. In some embodiments, the screwdriver 100 can identify when a screw has initially started driving (when the first threads have caught) based on current, voltage or torque readings. In some embodiments, the screwdriver 100 can identify when a screw is seating based on current, voltage or torque readings. In some embodiments, the screwdriver 100 can distinguish between a screw seating, a screw impacting a substrate of a higher or lower density, or a screw initiating its driving (initial threads catching) based on programming of a controller. Further, once a screw is fully seated, a user may try to further torque the screw after resetting any software in the screwdriver 100. Accordingly, the screwdriver software can include features that allow it to identify and differentiate the starting torque for an already seated screw from that of a screw that has just started driving by means of a higher initial torque value. This can prevent the screwdriver 100 from continuing to drive and potentially stripping an already seated screw.

In some embodiments, the screwdriver 100 can identify the substrate the screw tip is currently penetrating based on the readings of current and voltage and information programmed into the controller. In some embodiments, the device can compare voltage, current or torque readings while the screw is driving with preprogrammed expected values to identify the type of material the screw is currently in.

Various embodiments are configured to determine a status of the screw during the driving operation. For example, some embodiments are configured to determine when the screw is being seated (e.g., against a bone plate or other structure) in a tissue, such as in cancellous bone. Certain variants are configured to determine when the screw encounters (e.g., begins being driven into) another type of tissue, such as cortical bone. In some implementations, the screwdriver 100 can perform the determination based on parameters of a curve of the data input, such as torque curve. For example, the determination can be made based on the shape or slope of the curve. In some embodiments, the screwdriver 100 can automatically differentiate between different torque curves, such between as a potential damaging action (such as the tip of the screw hitting hard cortical bone) and the screw seating. Embodiments of the screwdriver 100 can then change operational parameters based on the torque curves (e.g., stopping or continuing motor operation). For example, the screwdriver 100 can be stopped at a torque value of X. X can be set by the user or can be included in the components of the screwdriver 100. Thus, the stop could be set electronically or mechanically. The torque values (nm, inch ounces, etc.) can be determined by converting a given current, voltage, and/or power, for example through the use of a lookup table or mathematical equation.

For example, FIGS. 54A and 54B illustrate torque curves where the tip of the screw encounters hard cortical bone (left) and where the screw is being seated (right), each figure showing different torque time values $t_1$, $t_2$, and $t_3$. As shown in FIG. 54A, when hard cortical bone is hit, the torque increases in a general linear fashion. However, during screw seating shown in FIG. 54B, the torque can increase in a non-linear and/or generally exponential fashion. Embodiments of the screwdriver 100 can differentiate between such torque changes. Various embodiments of the screwdriver 100 can differentiate between linear, non-linear (e.g., exponential), or other torque curves. In some embodiments, the rate of change of the torque is greater when hard cortical bone is encountered compared to when the screw is being seated. For example, the slope between $t_1$ and $t_3$ can be greater when hard cortical bone is encountered, than the slope between $t_1$ and $t_3$ when the screw is being seated.

In some embodiments, one or more operational parameters of the screwdriver 100 can change based on the determined type of torque curve, such whether the curve is linear or non-linear, as discussed above. For example, when the screw encounters a hard cortical bone (an example of which is shown in FIG. 54A) the screwdriver 100 can recognize that the curve is generally linear. In response, the screwdriver 100 can stop the driving of the screw, so as not to damage the bone. In contrast, for a screw seating operation (an example of which is shown in FIG. 54B), the screwdriver 100 can recognize that the curve is generally non-linear. In response, the screwdriver 100 can continue driving until torque-limiting criteria are met, such as disclosed herein.

The screwdriver can differentiate the different torque curves based on an algorithm. For example, if there are X consecutive increasing values and the torque values at $(t_2-t_1)/t_1 > Y\%$, where X and Y % can be selected and set by a user, the motor 12 can be depowered. In some embodiments, an impact with hard cortical bone will have a relatively sharp increase, so the Y % value will be larger than for screw seating, which will typically have a relatively gradual increase and thus will not satisfy both conditions for stopping the motor of the screwdriver such as shown in FIGS. 54A-B. In various embodiments, the algorithms and processes described in this disclosure can be implemented by a controller (e.g., a processor operably coupled with a memory) of the screwdriver 100.

Adaptive Torque Limiting

In some embodiments, the screwdriver 100 can incorporate adaptive torque limiting features. These features can be used with, for example, a screw or a drill bit, to perform density differentiation analysis. As mentioned above, the screwdriver 100 can be configured to drive a screw and/or a drill bit. For example, the screwdriver 100 can rotate the drill bit to drill into a bone to form a hole. The drill bit can be removed from the hole and a screw can be inserted.

Figure 55:
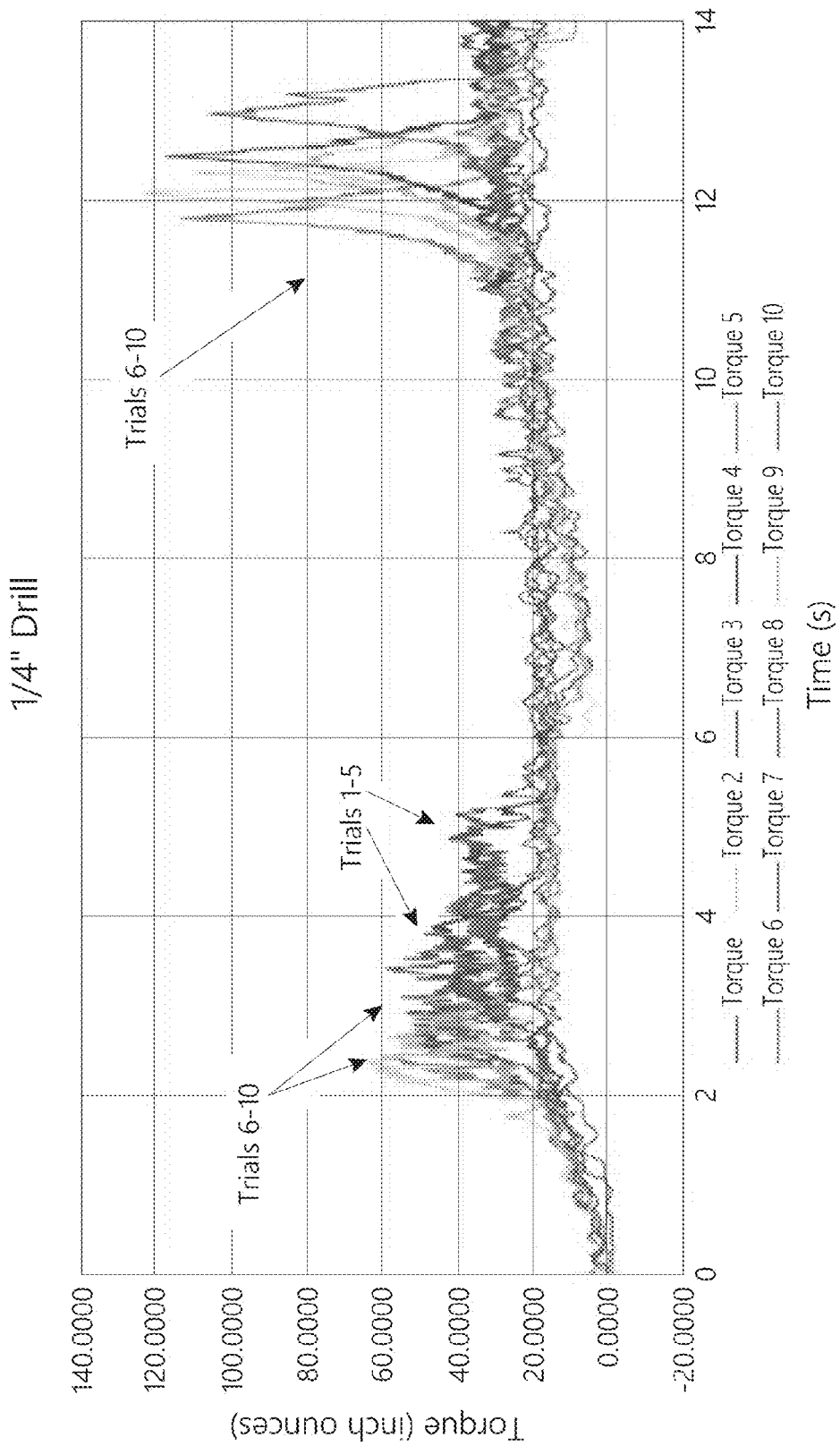
FIG. 55 illustrates torque curves during trial drilling operations through simulated vertebra.

FIG. 55 illustrates various example torque curves produced by drilling through a simulated vertebra. The values for trials 1-5 display an initial torque peak as they break through the outer cortical layer of the vertebra. As they transition through the less dense cancellous layer the torque decreases and levels off. Trials 1-5 represent a properly drilled hole. On the other hand, as shown in FIG. 15, the values for trials 6-10 display two torque peaks. The first peak generally aligns with peaks in trials 1-5, but the second peak comes later (trials 1-5 do not have this second peak). As shown in the figure, the torque value of this second peak is nearly twice the first. In some embodiments, the second peak could be one and a half times, double, triple, or other values above or in between the listed values as compared to the first peak. The particular size of the second peak is not limiting. This second peak represents breaking through a second cortical layer after traveling through cancellous bone, which is typically undesirable and to be avoided.

Figure 56:
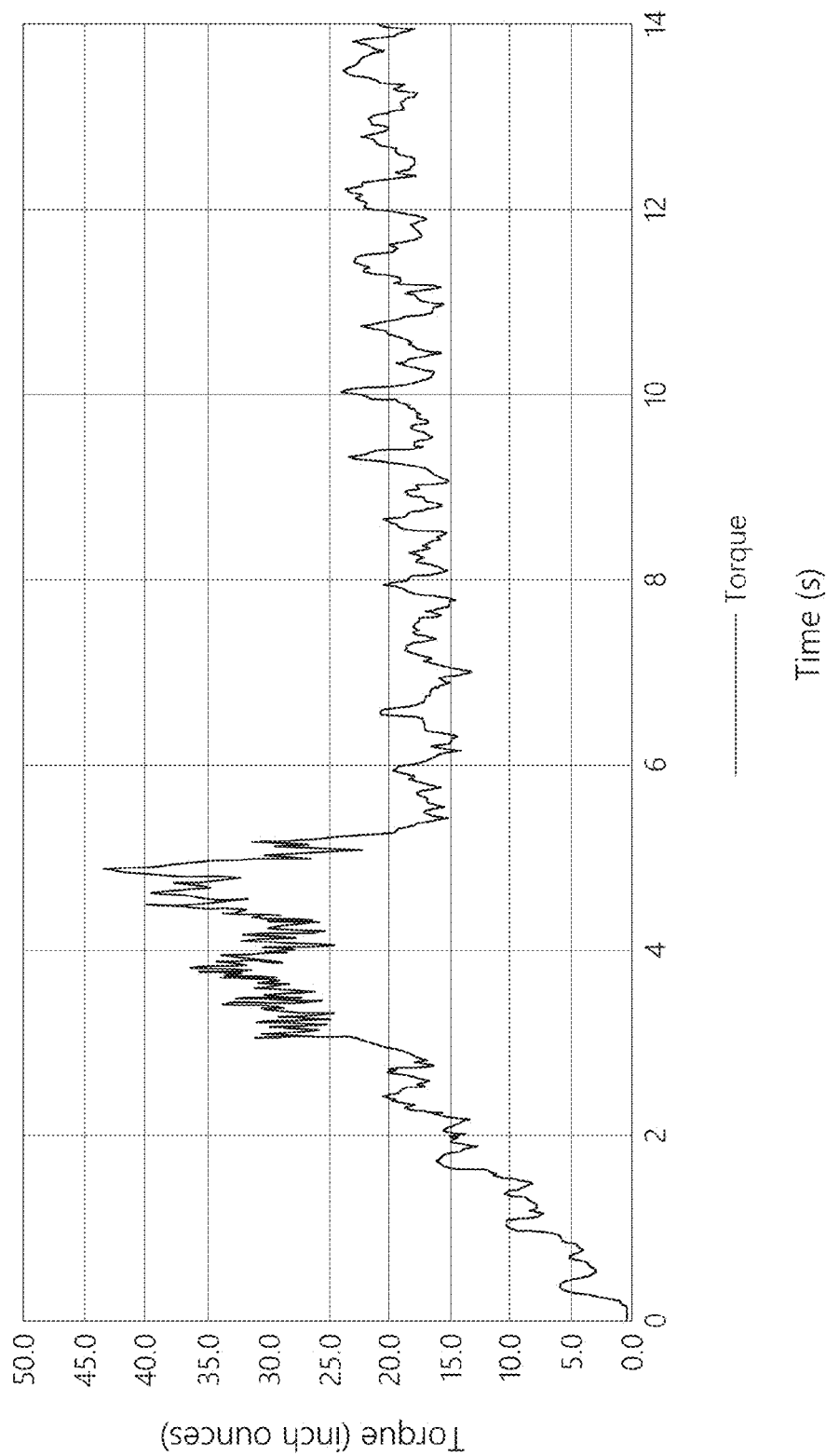
FIG. 56 illustrates a torque curve during a properly aligned drilling operation.

FIG. 56 illustrates the torque curve of a properly aligned drill bit. The drill travels through cortical layer as it reaches the torque peak and then drop-offs to a lower value as it passes through cancellous bone. As shown, there is no large secondary torque peak, indicating breaking through the second cortical layer. Thus, for the properly aligned drill bit, the driver would have no need to limit the torque, though certain torque-limiting features could still be used.

Figure 57:
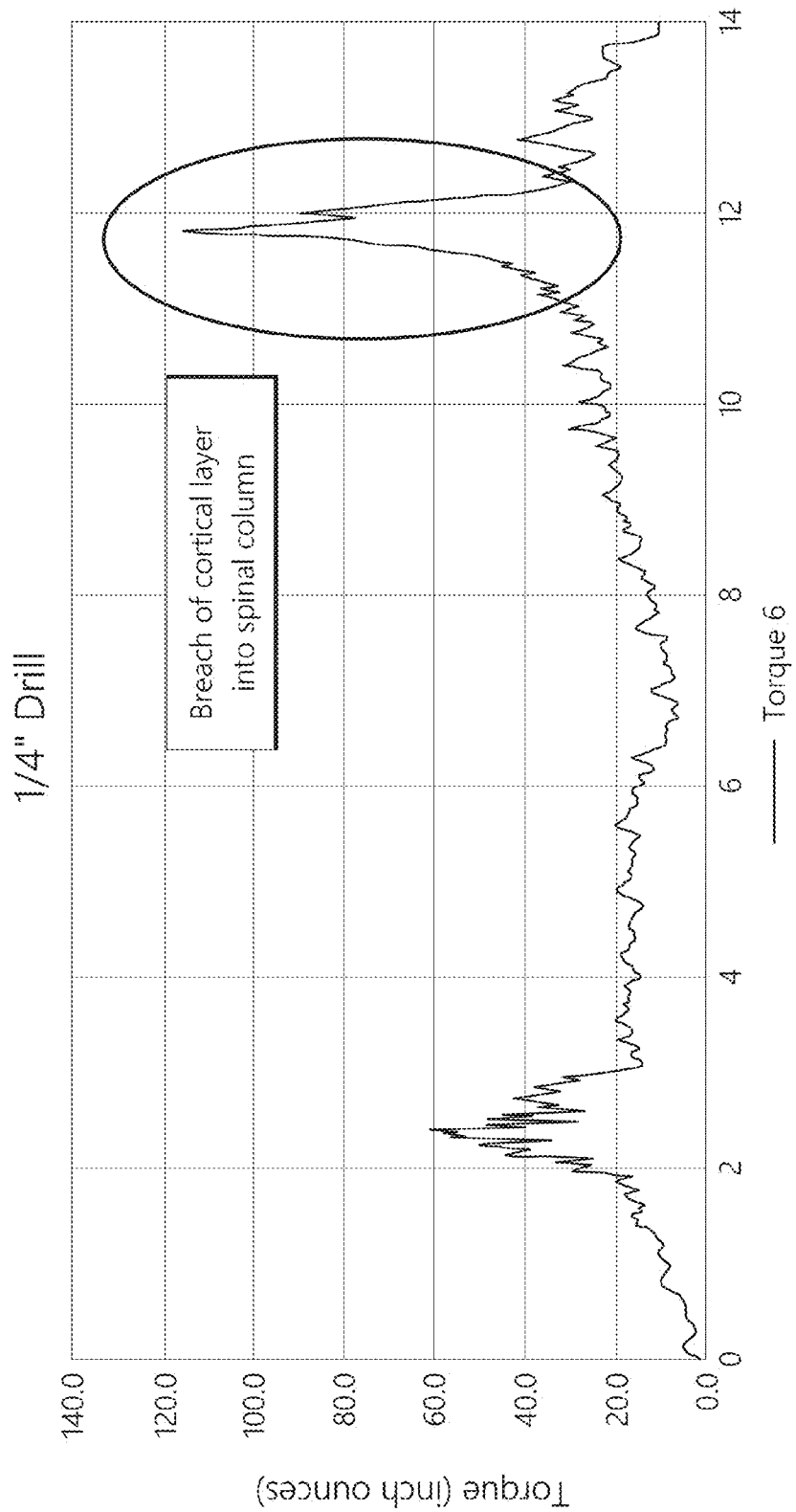
FIG. 57 illustrates a torque curve during a misaligned drilling operation.

FIG. 57 illustrates the torque curve of a misaligned drill bit. As shown, there are two torque peaks, with the second torque peak being substantially higher than the first peak indicating that the drill is breaking through the second cortical layer. As compared to FIG. 56, until the breach occurs the drill follows a similar path to the properly aligned drill.

Certain embodiments are configured to identify and/or capture the differences between a properly drilled hole and a hole that breaches the spinal column. Various embodiments are configured to take action in response to determining that the hole has or will breach the spinal column. For example, the driver can stop driving and/or drilling, issue an audible and/or visual alert, etc.

In some embodiments, a peak finder can be used with the screwdriver 100. The peak finder can work by locating the torque peak using, for example, running average, first derivative, and/or preset values. In the running average approach, the peak torque can be stored. Then, for every feedback cycle the running average would be evaluated against the torque peak. If the torque peak were higher than the stored value, the higher torque peak would replace the value. This would continue until the running average value decreases for a given number of feedback cycles (e.g., 1, 10, 20, 50, or 100), which can represent the backside of the initial peak. For the preset value approach, this would be catered to specific drill systems after extensive testing.

Adaptive torque limiting, such as where the motor shut-offs when a breach is detected, could be triggered by any of the following. In some embodiments, once the torque peak is established, if the torque hits a particular percentage of Y % of this value then the driver can shut off the motor of the screwdriver 100. The percentage can be, for example, 50, 60, 70, 80, 90, 95, 99, 100, 105, 110, and the particular percentage used is not limiting. In some embodiments, once the torque peak is established, if the rate of change (or derivative) in the moving average exceeds a particular value, then the driver can shut of the motor 12 of the screwdriver 100.

Figure 58:
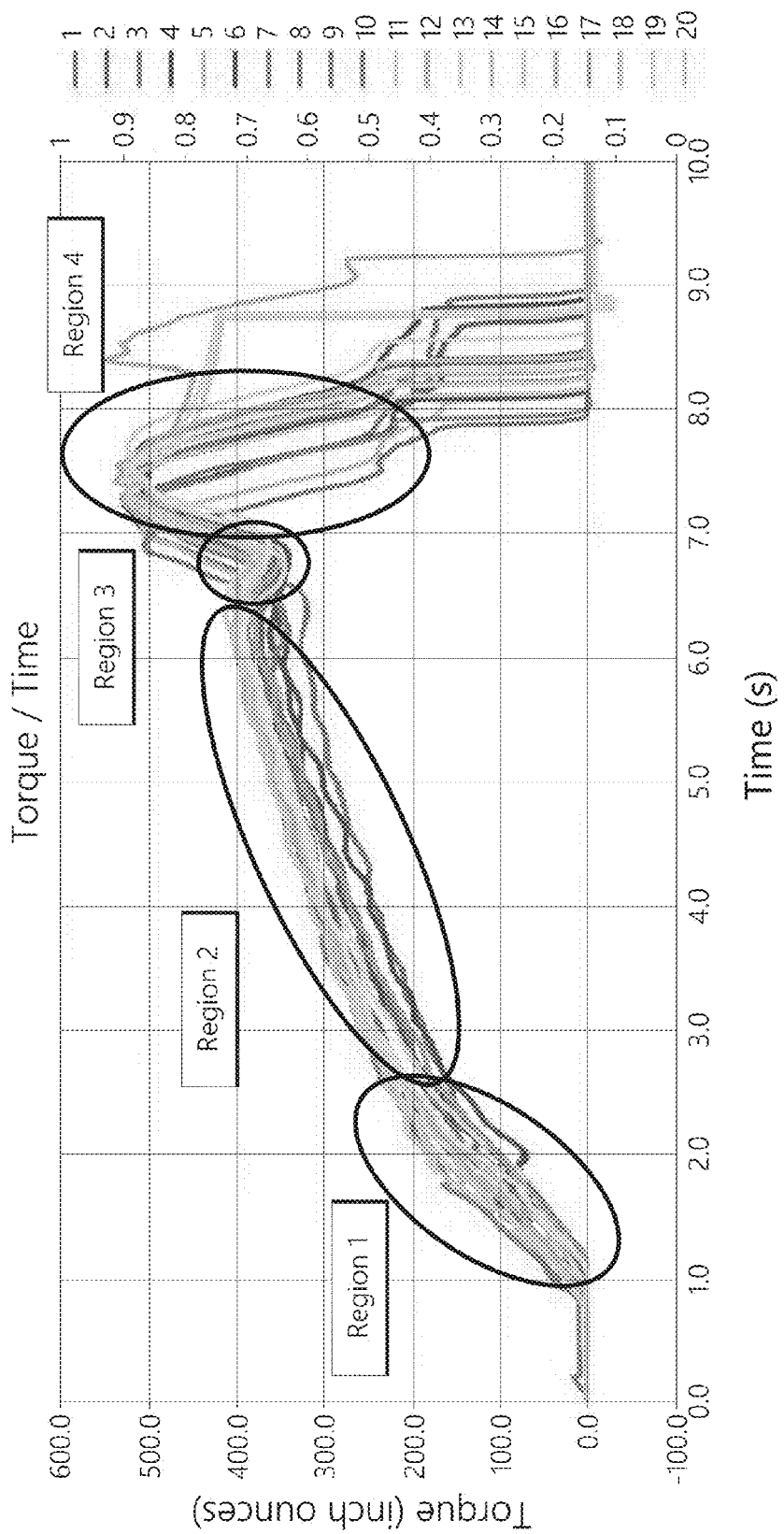
FIG. 58 illustrates torque curves of multiple screws being driven into vertebra without a breach occurring.

FIG. 58 illustrates the torque curve of a screw being driven into a vertebra without breaching the spinal column. As shown, the screw travels through the cortical layer in region 1, drives through the cancellous layer in region 2, the screw threads have all entered the bone in region 3, and the screw has been seated in region 4. In some embodiments, it can be advantageous for the driver to stop the screw prior to or just after seating (e.g., region 4). This is because the attachment on the screw head can utilize mobility to align the rods along the vertebrae as the screw itself is not threaded all the way to the head. The screws can be placed into pre-drilled holes which are governed by the drilling processes discussed above. Thus, in some embodiments, the screwdriver 100 can limit the motor 12 when all threads have entered the bone which occurs in region 3.

In some embodiments, the screwdriver 100 can utilize the following concepts for adaptive torque limiting. In some embodiments, the motor 12 can shut off after consecutive decreasing torque values (for example, 3, 4, 5, 10, 15, or 20 decreasing values). In some embodiments, rate of change/first derivative that indicates a decreasing slope can cause the driver to stop the motor. In some embodiments, a valley check algorithm can be used that mimics the peak finding algorithm discussed above.

In some embodiments, the drill/driver could interact with the drill bits and driver in the following ways. The collet of the driver can be configured to receive different geometries, one each for the drill bit and the driver blade. When a drill bit is inserted, a button, switch, or other mechanism can be triggered by a user such that a shut-off algorithm for the drill is activated. Thus, the algorithm may only be used by activation of the user. In some embodiments, the algorithm can be activated upon insertion of the driver blade or drill bit/screw. In some embodiments, the drill can operate to a certain depth. Without a predrilled path to follow after this depth, a sharp increase in torque would be seen in the screw seating. This depth could be known from the last drill blade to be inserted into the driver, or through the entry of additional values.

Robotic Features

Embodiments of the screwdriver 100 and hardware/software can be configured to be used and/or integrated with robotics, such as a robotic arm. The robotic arm can comprise an arm unit and a controller unit (e.g., a processor and a memory). In some embodiments, the robotics can be configured to use the screwdriver 100 to drive a screw into a patient's body. This motion can be performed automatically by the robotics, under a user's control, or a combination thereof.

In some embodiments, the screwdriver 100 can be removably attached to the robotics. In certain variants, the screwdriver 100 can include attachments to the proximal end or the distal end of the arm unit of the robotics, this could be in conjunction or alternatively to a handheld operation. In some implementations, the screwdriver can be fully integrated with the arm unit. Thus, in some embodiments a separate screwdriver may not be attached to the robotic arm and instead the robotic arm can include components of the screwdriver 100, including the sensing technology discussed in detail above. The robotic arm itself can drive a screw into a patient in some embodiments without an additional hand piece.

In some embodiments, the screwdriver 100 can be electrically connected with the robotics. For example, both can share a common power supply. In some embodiments, the screwdriver 100 can have a separate electric power source outside of the robotics. In certain implementations, the screwdriver and robotics can share software and/or data between one another.

Certain other features discussed herein, such as torque limiting, can be applied to the robotics. For example, the robotic arm can be configured to receive current feedback from the drive motor of the screwdriver 100. The robotics can be configured to decrease and/or stop the driving of a screw (or other motion) in response to the torque applied by the screwdriver 100 to the screw reaching or exceeding a certain threshold. In some embodiments, the robotics can identify when a screw is seated or a drill is plunging, such as based on current feedback from the screwdriver 100.

The robotics can be configured to receive force feedback from the motion of the screwdriver 100. In certain implementations, the robotic arm can modify its behavior based on the force feedback. For example, the robotic arm can execute torque limiting functionality. In certain embodiments, the robotic arm is configured to detect a seated screw in a similar manner that a human is capable of detecting a seated screw, such as by detecting that the forward progress of the screw has ceased, such as with force, vibration, acceleration, and/or motion sensors. For example, a sudden increase in resistance to the motion along a given axis could be indicative of a seated screw (or other torque), and the robotic arm could reduce or stop forward motion of the screw and/or take other actions (e.g., provide an alarm or announce to a user to reduce or stop forward motion).

In some implementations, the robotic arm can be used to drive screws (e.g., spinal pedicle screws) into a patient, which can be a tiresome, repetitive, relatively low risk, and/or commoditized procedure. Such a robotic arm could drive pedicle screws with extreme precision and mitigate risks of cortical breach, such as based on information received from the screwdriver 100. This could enable use of the screwdriver 100 to be fully automated and/or to not require any human control (or reducing or minimizing any human control). Thus, in some embodiments, the workload of surgeons, or other users, could be reduced or eliminated from the work of driving pedicle screws.

In some implementations, the screwdriver 100 can be used with a hybrid robot. The hybrid robot could have a number of different modes. For example, one mode could be to act as a surgical assistive tool. In certain modes, the robot could provide risk mitigation and/or territory violation prevention. For example, the robot could warn and/or inhibit a user (e.g., a surgeon) from moving into a certain space (e.g., a "no-fly zone"), and/or out of a certain space, when operating the screwdriver 100. In some modes, the robot can perform commoditized operations, such as driving screws with the screwdriver in a fully automated manner.

Depth Gauge Mechanism

Figure 59:
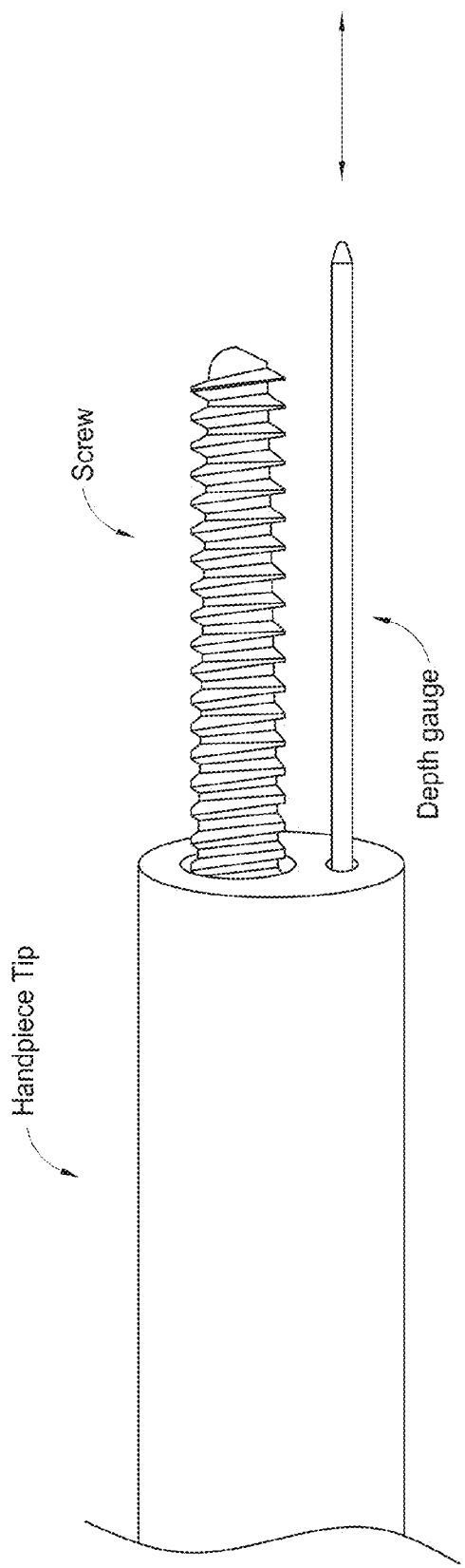
FIG. 59 illustrates an embodiment of a depth gauge for use on an embodiment of a screwdriver.

In some embodiments, the screwdriver 100 can further include a depth gauge as shown in FIG. 59. As shown, the gauge can generally extend from the screwdriver 100 and be used to determine the real time depth of a screw (or other tool such) for the purpose of identifying high probability impact zones, though the gauge can be used to determine other zones as well. The depth gauge can be integrally formed with the screwdriver 100 in some embodiments. In some embodiments, the depth gauge can be attachable and/or removable to the screwdriver 100, such as by insertion into an aperture in the screwdriver 100 as shown in FIG. 59. In some embodiments, the depth gauge can be moveable on the screwdriver, for example, pushing into the screwdriver 100 as depth is increased. In some embodiments, the depth gauge may be a laser. In some embodiments, the depth gauge can include markings indicating depth. In some embodiments, the depth gauge can provide depth information to the screwdriver 100 and the screwdriver 100 can provide the output to the user. In some embodiments, the depth gauge can provide a physical stop. In some embodiments, the depth gauge can provide visual or auditory indications of the depth of a screw. In some embodiments, once a particular depth is reached, for example, as set by a user, the screwdriver 100 can automatically shut off and/or slow down.

As an example, if the pedicle channel is 15 mm plus or minus 2 mm for 99% of the adult population, the depth gauge can be used to determine depths at which the breach is most likely to occur. Thus, the depth gauge, in combination with the torque measurements discussed herein, can be used to increase the accuracy and reliability of the screwdriver 100. In some embodiments, the depth gauge can be used to identify when a screw has seated in a particular location in a patient.

As another example, for a drill/driver combination, if the medical stand is to only drill a pilot hole that is 2 mm dep, embodiments of the gauge could determine the depth of the drill and stop the drilling function (e.g., stopping motor and/or switching to manual, providing a manual stop) when the depth was reached. In some embodiments, the depth gauge measurements can be overridden by a user, such as if a patient is outside the norm.

In some embodiments, a user can identify the type of screw to the screwdriver 100. The screwdriver 100 can then have access to a lookup table to find the insertion depth of that type of screw (such as the total length of the screw less the length of the head of the screw). The screwdriver 100 can then determine that the screw is seated (or in the proper position) once the depth gauge reaches that insertion depth value. In some embodiments, the lookup table, or other lookup methodology, may also include procedure information that could further adjust the depth gauge readings. In some embodiments, the user does not have to identify the type of screw and the screwdriver 100 will automatically identify it.

Summary

Various screwdriver devices, systems, and methods have been disclosed in the context of aspects of certain embodiments, examples, and variations. Nevertheless, the present disclosure extends beyond the specifically disclosed embodiments, examples, and variations to other alternative embodiments and/or uses of the invention, as well as obvious modifications and equivalents thereof. In addition, while a number of variations of the screwdriver have been shown and described in detail, other modifications, which are within the scope of this disclosure, will be readily apparent to those of skill in the art based upon this disclosure. Moreover, while certain examples have been discussed in the context of surgical screwdrivers, the various inventions disclosed herein are not limited to use in surgical screwdrivers. Indeed, the various inventions disclosed herein are contemplated for in use a variety of other types of devices and other environments.

Certain features have been described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Any of the steps and blocks can be adjusted or modified. Other or additional steps can be used. None of the steps or blocks described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

Conditional language used herein, such as, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. The term "and/or" means that "and" applies to some embodiments and "or" applies to some embodiments. Thus, A, B, and/or C is equivalent to A, B, and C written in one sentence and A, B, or C written in another sentence. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Terms relating to circular shapes as used herein, such as diameter or radius, should be understood not to require perfect circular structures, but rather should be applied to any suitable structure with a cross-sectional region that can be measured from side-to-side. Terms relating to shapes, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations. Likewise, shapes modified by the word "generally" (e.g., "generally cylindrical") can include reasonably close approximations of the stated shape.

Some embodiments have been described in connection with the accompanying drawings. The figures are drawn to scale, but such scale should not be limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

In summary, various embodiments and examples of torque-limiting screwdriver systems and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. Moreover, this disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

The following is claimed:

1. A torque-limiting screwdriver comprising:
  a body comprising a handle that is configured to be grasped by a user;
  a motor positioned in the body;
  a drive head configured to be rotated by the motor and to receive a bit that engages a screw;
  a battery positioned in the handle, the battery configured to provide electric power to the motor; and
  a processor positioned in the body;
  wherein, under the control of the processor, the torque-limiting screwdriver is configured to:
    apply torque to the screw;
    monitor current, voltage, or torque values of the motor;
    determine, from the current, voltage, or torque values, a plurality of torque values associated with the torque applied to the screw;
    determine a first average from the plurality of torque values;
    determine a second average from the plurality of torque values;
    compare the first average to the second average;
    determine that the first average is greater than the second average;
    determine that a peak in the torque comprising an inflection point in the torque has occurred; and
    limit the amount of torque applied to the screw in response to the peak in the torque.

2. The torque-limiting screwdriver of claim 1, wherein the torque-limiting screwdriver is configured to determine that the inflection point in the torque has occurred by detecting a number of consecutive increasing torque values, followed by one or more interim torque values, followed by a number of consecutive decreasing values.

3. The torque-limiting screwdriver of claim 1, wherein the torque-limiting screwdriver is configured to determine that the inflection point in the torque has occurred by detecting that a slope of the torque changes from positive to negative.

4. The torque-limiting screwdriver of claim 1, wherein the torque-limiting screwdriver is configured to determine that the inflection point in the torque has occurred by detecting that the torque is greater than or equal to a threshold torque value.

5. The torque-limiting screwdriver of claim 1, further comprising an input device configured to send a signal to the processor to change the operation by which the torque-limiting screwdriver determines that the inflection point in the torque has occurred.

6. The torque-limiting screwdriver of claim 1, wherein the torque-limiting screwdriver is further configured to limit the amount of torque after a time interval elapses from when the inflection point occurs.

7. The torque-limiting screwdriver of claim 1, further comprising an actuator configured to switch the screwdriver from a manual mode to a powered mode, wherein:
  in the manual mode, the motor does not rotate the drive head;
  in the powered mode, the motor rotates the drive head; and
  a default mode for the torque-limiting screwdriver is the manual mode.

8. The torque-limiting screwdriver of claim 1, wherein the processor is positioned in the handle of the body.

9. The torque-limiting screwdriver of claim 1, wherein the handle comprises a pistol grip.

10. A system comprising the torque-limiting screwdriver of claim 1 and an extension adaptor configured to removably attach to the screwdriver, the extension adaptor configured to enable insertion of the screw into a bone that is spaced at least 30 mm apart from the body of the screwdriver.

11. A robotic assembly for inserting screws, the robotic assembly comprising:
  a robotic arm; and
  a torque-limiting screwdriver mounted to the robotic arm, the screwdriver comprising:
    a body comprising a handle;
    a motor positioned in the body;
    a drive head, the drive head configured to receive a bit that engages a screw and to be rotated by the motor;
    wherein the screwdriver is configured to:
      monitor the current draw of the motor to detect a plurality of torque values associated with the torque applied to the screw;
      determine a first average from the plurality of torque values;
      determine a second average from the plurality of torque values;
      compare the first average to the second average;
      determine that an inflection point in the torque has occurred by determining that the first average is greater than the second average; and
      limit the amount of torque applied to the screw in response to a torque limiting condition being satisfied.

12. The robotic assembly of claim 11, wherein the screwdriver is further configured to stop the motor after the torque limiting condition has been satisfied.

13. The robotic assembly of claim 11, wherein the torque limiting condition comprises the screwdriver detecting an inflection point in the torque applied to the screw.

14. The robotic assembly of claim 13, wherein detecting the inflection point comprises detecting a number of consecutive increasing torque values, followed by one or more interim torque values, followed by a number of consecutive decreasing values.

15. The robotic assembly of claim 13, wherein detecting the inflection point comprises detecting that the torque is greater than or equal to a threshold torque value.

* * * * *

UNITED STATES PATENT AND TRADEMARK OFFICE
CERTIFICATE OF CORRECTION

PATENT NO. : 10,383,674 B2  
APPLICATION NO. : 15/615722  
DATED : August 20, 2019  
INVENTOR(S) : Benjamin J. Sexson It is certified that error appears in the above-identified patent and that said Letters Patent is hereby corrected as shown below:

In the Drawings

Sheet 32 of 61 (FIG. 29), Line 5, change "corical" to --cortical--.

Sheet 35 of 61 (FIG. 32), Line 1, change "Sandwitch" to --Sandwich--.

Sheet 36 of 61 (FIG. 33), Line 1, change "Sandwitch" to --Sandwich--.

In the Specification

Column 16, Line 40 (approx.), change "overtorqueing" to --overtorquing--.

Column 32, Line 31, change "values" to --values.--.

Column 37, Line 51, change "types," to --types.--.

Column 44, Line 49, change "average+/-standard" to --average +/- standard--.

Column 50, Line 28, change "dep," to --deep,--.

In the Claims

Column 54, Lines 51-52 (approx.), change "detecting an inflection point" to --detecting the inflection point--.

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*